US010526580B2

(12) United States Patent
Esmeraldo De Campos Vazão et al.

(10) Patent No.: US 10,526,580 B2
(45) Date of Patent: Jan. 7, 2020

(54) DIFFERENTIATED CELL POPULATION OF ENDOTHELIAL CELLS DERIVED FROM HUMAN PLURIPOTENT STEM CELLS, COMPOSITION, SYSTEM, KIT AND USES THEREOF

(71) Applicant: BIOCANT-ASSOCIAÇÃO DE TRANSFERÊNCIA DE TECNOLOGIA, Cantanhede (PT)

(72) Inventors: Helena Sofia Esmeraldo De Campos Vazão, Alcobaça (PT); Lino Da Silva Ferreira, Coimbra (PT); Hugo Agostinho Machado Fernandes, Joane (PT)

(73) Assignee: BIOCANT-ASSOCIAÇÃO DE TRANSFERÊNCIA DE TECNOLOGIA, Cantanhede (PT)

( * ) Notice: Subject to any disclaimer, the term of this patent is extended or adjusted under 35 U.S.C. 154(b) by 0 days.

(21) Appl. No.: 15/637,068

(22) Filed: Jun. 29, 2017

(65) Prior Publication Data
US 2018/0023051 A1 Jan. 25, 2018

Related U.S. Application Data

(62) Division of application No. 14/651,548, filed as application No. PCT/IB2013/061110 on Dec. 18, 2013, now abandoned.

(30) Foreign Application Priority Data

Dec. 18, 2012 (PT) .......................... 106699

(51) Int. Cl.
*C12N 5/071* (2010.01)
(52) U.S. Cl.
CPC ........ *C12N 5/069* (2013.01); *C12N 2501/165* (2013.01); *C12N 2501/40* (2013.01); *C12N 2501/42* (2013.01); *C12N 2501/50* (2013.01); *C12N 2501/727* (2013.01); *C12N 2501/999* (2013.01); *C12N 2503/02* (2013.01); *C12N 2506/02* (2013.01); *C12N 2506/45* (2013.01); *C12N 2521/00* (2013.01)

(58) Field of Classification Search
CPC .......... C12N 2501/165; C12N 2501/40; C12N 2501/42; C12N 2501/727; C12N 2501/999; C12N 2503/02; C12N 2506/02; C12N 2506/45; C12N 2521/00
See application file for complete search history.

(56) References Cited

U.S. PATENT DOCUMENTS

| | | |
|---|---|---|
| 7,071,199 B1 | 7/2006 | Hirst |
| 2009/0053752 A1 | 2/2009 | Blackman et al. |
| 2009/0104159 A1 | 4/2009 | Prosper et al. |
| 2011/0159522 A1 | 6/2011 | Kamm et al. |
| 2012/0211373 A1 | 8/2012 | El-Sayed et al. |
| 2012/0301443 A1 | 11/2012 | Raffi et al. |
| 2014/0306371 A1* | 10/2014 | Guenther ............... C12M 23/16 264/177.18 |

FOREIGN PATENT DOCUMENTS

WO 2011090684 A2 7/2011

OTHER PUBLICATIONS

Schulz et al., PNAS, E2665-E2674, published online Sep. 4, 2012.*
Chen et al., Cell Rep.,; 2(6): 1684-1696, Dec. 27, 2012; Published online Nov. 29, 2012.*
Estrada et al., Biomicrofluidics, 5, 032006: pp. 11, 2011.*
Ivashchenko et al., Ann J Physiol Heart Circ Physiol 298: H251-H258, 2010.*
Pullamsetti, S. et al. "Increased levels and reduced catabolism of asymmetric and symmetric dimethylarginines in pulmonary hypertension." FASEB J, (2005), vol. 19, pp. 1175-1177.
Schulz, M. M. P. et al. "Phenotype-based high-content chemical library screening identifies statins as inhibitors of in vivo lymphangiogenesis." Proc Natl Acad Sci USA, (2012), vol. 109, pp. E2665-2674.
Smart, N. et al. "Thymosin beta4 induces adult epicardial progenitor mobilization and neovascularization." Nature, (2007), vol. 445, doi:doi:10.1038/nature05383, pp. 177-182, XP002458083.
Sone, M. et al. "Pathway for differentiation of human embryonic stem cells to vascular cell components and their potential for vascular regeneration." Arteriosclerosis, Thrombosis, and Vascular Biology, (2007), vol. 27, pp. 2127-2134.
Suzuki et al. "Arterial shear stress augments the differentiation of endothelial progenitor cells adhered to VEGF-bound surfaces." Biochemical and Biophysical Research Communications, vol. 423, No. I, May 23, 2012 (May 23, 2012), pp. 91-97, XP028496500, ISSN: 0006-291X, DOI: 1.1016/J.BBRC.2012.05.088 [retrieved on May 23, 2012].
Swift, M. R. et al. "Arterial-venous specification during development." Circulation Research, (2009), vol. 104, pp. 576-588.
Tesfamariam, B. et al. "Endothelial injury in the initiation and progression of vascular disorders." Vascul Pharmacol, (2007), vol. 46, doi:doi:10.1016/j.vph.2006.11.005, pp. 229-237, XP005857777.
Thi, M. M. et al. "The role of the glycocalyx in reorganization of the actin cytoskeleton under fluid shear stress: a "bumper-car" model." Proc Natl Acad Sci USA, (2004), vol. 101, pp. 16483-16488.
Tideman, E. et al. "Cognitive function in young adults following intrauterine growth restriction with abnormal fetal aortic blood flow." Ultrasound Obstet Gynecol, (2007), vol. 29, pp. 614-618.

(Continued)

*Primary Examiner* — Thaian N Ton
(74) *Attorney, Agent, or Firm* — Leason Ellis LLP

(57) ABSTRACT

The present disclosure relates to a differentiated cell population of endothelial cells derived from human pluripotent stem cells. The present invention also relates to a composition, a system and a kit comprising those cells and uses thereof. The present disclosure also described the combination of arterial ECs derived from human pluripotent stem cells with a microfluidic system to create a vascular kit for high-throughput drug screening and/or toxicology analysis. This technology may find particular use for the identification of drugs that may have a fetal cytotoxic effect.

16 Claims, 50 Drawing Sheets

Specification includes a Sequence Listing.

(56) References Cited

OTHER PUBLICATIONS

Tsai, M. et al. "In vitro modeling of the microvascular occlusion and thrombosis that occur in hematologic diseases using microfluidic technology." J Clin Invest, (2012), vol. 122, pp. 408-418.
Tzima, E. et al. "A mechanosensory complex that mediates the endothelial cell response to fluid shear stress." Nature, (2005), vol. 437, pp. 426-431.
Vazao, H. et al. "Towards the maturation and characterization of smooth muscle cells derived from human embryonic stem cells." PLOS ONE, (2011), vol. 6, p. E17771.
Vodyanik, M.A. et al. "Leukosialin (CD43) defines hematopoietic progenitors in human embryonic stem cell differentiation cultures." Blood, (2006), vol. 108, pp. 2095-2105, XP007913346.
Wang, H. et al. "Molecular distinction and angiogenic interaction between embryonic arteries and veins revealed by ephrin-B2 and its receptor Eph-B4." Cell, (1998), vol. 93, doi:doi:10.1016/S0092-8674(00)81436-1, pp. 741-753, XP002120944.
Wang, L. et al. "Endothelial and Hematopoietic Cell Fate of Human Embryonic Stem Cells Originates from Primitive Endothelium with Hemangioblastic Properties." Immunity, (2004), vol. 21, doi:doi:10.1016/j.immuni.2004.06.006, pp. 31-41, XP002484358.
Wang, Z.Z. et al. "Endothelial cells derived from human embryonic stem cells form durable blood vessels in vivo." Nat Biotechnol, (2007), vol. 25, pp. 317-318.
Yurugi-Kobayashi, Takami et al. "Adrenomedullin/cyclic AMP pathway induces notch activation and differentiation of arterial endothelial cells from vascular progenitors." Arteriosclerosis Thrombosis and Vascular Biology, vol. 26, No. 9, Sep. 2006 (Sep. 2006), pp. 1977-1984, XP055118884.
Non Final Office Action of corresponding U.S. Appl. No. 14/651,548 dated Aug. 11, 2016.
"Endothelial Cell Markers," from Millipore, pp. 1-5, accessed from https://www.emdmillipore.com/US/en/product/Endothelial-Cell-Markers,MM_NF-C133595, Aug. 4, 2016.
Bochenek et al., J. of Cell Science, 123: 1235-1246, 2010.
Pahakis et al., Biochem. Biophys. Res. Commun., 355(1): 228-233, 2007.
International Search Report and Written Opinion for corresponding International Patent Application No. PCT/IB2013/061110 dated Nov. 19, 2014.
International Preliminary Report on Patentability for corresponding International Patent Application No. PCT/IB2013/061110 dated Jun. 23, 2015.
European Examination Report in corresponding European Patent Application No. 13826629.1 dated Dec. 9, 2016.
Agasse, F. et al. "Neuropeptide Y promotes neurogenesis in murine subventricular zone", Stem Cells, (2008), vol. 26, doi:doi:10.1634/STEMCELLS.2008-0056, pp. 1636-1645, XP002596209.
Aranguren et al. "In vitro and in vivo arterial differentiation of human multipotent adult progenitor cells", Blood, vol. 109, No. 6, Nov. 7, 2006 (Nov. 7, 2006), pp. 2634-2642, XP055086945, us ISSN: 0006-4971, DOI: 10.1182/blood-2006-06-030411.
Arnold, L. D. et al. "Pyrrolo[2,3-d]pyrimidines containing an extended 5-substituent as potent and selective inhibitors of lck." Bioorg Med Chem Lett, (2000), vol. 10, doi:doi:10.1016/S0960-894X(00)00441-8, pp. 2167-2170, XP004211995.
Beger, R. H. et al. "ADMA: an emerging cardiovascular risk factor", Vasc Med, (2005), vol. 10, No. 1, pp. 1-2.
Bernardino, L. et al. "Tumor necrosis factor-alpha modulates survival, proliferation, and neuronal differentiation in neonatal subventricular zone cell cultures", Stem Cells, (2008), vol. 26, pp. 2361-2371.
Breiteneder-Geleff, S. et al. "Angiosarcomas express mixed endothelial phenotypes of blood and lymphatic capillaries: podoplanin as a specific marker for lymphatic endothelium", Am J Pathol, (1999), vol. 154, pp. 385-394, XP002958898.
Chi, J. T. et al. "Endothelial cell diversity revealed by global expression profiling." Proc Natl Acad Sci USA, (2003), vol. 100, pp. 10623-10628.

Chin L. K. et al. "Production of reactive oxygen species in endothelial cells under different pulsatile shear stresses and glucose concentrations." Lab on a Chip, vol. 11, No. 11, 2011, pp. 1856-1863, XP055143586.
Cho, S. W. et al. "Improvement of postnatal neovascularization by human embryonic stem cell derived endothelial-like cell transplantation in a mouse model of hindlimb ischemia", Circulation, (2007), vol. 116, pp. 2409-2419.
D'Amato, R. J. et al. "Thalidomide is an inhibitor of angiogenesis." Proc Natl Acad Sci U S A, (1994), vol. 91, doi:doi:10.1073/pnas.91.9.4082, pp. 4082-4085, XP002638198.
Daylon, J. et al. "Expansion and maintenance of human embryonic stem cell-derived endothelial cells by TGF beta inhibition is ld1 dependent." Nature Biotechnology, [Online] vol. 28, No. 2, Jan. 17, 2010 (Jan. 17, 2010). pp. 161-166, 1, XP002682519, ISSN: 1087-0156, DOI: 10.1038/NBT.1605. Retrieved Jan. 17, 2010: http://www.nature.com/nbt/journal/v28/n2/full/nbt.1605.html>.
Ferreira, L.S. et al. "Vascular progenitor cells isolated from human embryonic stem cells give rise to endothelial and smooth muscle like cells and form vascular networks in vivo." Circulation Research, (2007), vol. 101, doi: doi:10.1161/CIRCRESAHA.107.150201, pp. 286-294, XP008157308.
Fiddes, L.K. et al. "A circular cross-section PDMS microfluidics system for replication of cardiovascular flow conditions." Biomaterials, (2010), vol. 31, doi:doi:10.1016/j.biomaterials.2010.01.082, pp. 3459-3464, XP026945980.
Florian, J.A. et al. "Heparan sulfate proteoglycan is a mechanosensor on endothelial cells." Circulation Research, (2003), vol. 93, pp. E136-142.
Furchgott, R. "Endothelium-derived relaxing factor: discovery, early studies, and identification as nitric oxide." Bioscience Reports, (1999).
Gao, Y et al. "Prostaglandins E2 and I2 cause greater relaxations in pulmonary veins than in arteries of newborn lambs." J Appl Physiol, (1996), vol. 81, pp. 2534-2539.
Gaucher, C. et al. "In vitro impact of physiological shear stress on endothelial cells gene expression profile." Clin Hemorheol Microcirc, (2007), vol. 37, pp. 99-107.
Gentile, C. et al. "VEGF-mediated phosphorylation of eNOS regulates angioblast and embryonic endothelial cell proliferation." Developmental Biology, (2013), vol. 373, pp. 163-175.
Ghaemmaghami et al. "Biomimetic tissues on a chip for drug discovery." Drug Discovery Today, vol. 17, No. 3-4, Feb. 1, 2012 (Feb. 1, 2012), pp. 173-181, XP055071196, ISSN: 1359-6446, DOI: 10.1016/j.drudis.2011.10.029.
Grynkiewicz, G et al. "A new generation of Ca2+ indicators with greatly improved fluorescence properties." J Biol Ahem, (1985), vol. 260, pp. 3440-3450.
Haase, A. et al. "Generation of induced pluripotent stem cells from human cord blood." Cell Stem Cell, (2009), vol. 5, doi:10.1016/j.stem.2009.08.021, pp. 434-441, XP008162338.
Ho, P et al. "Terbinafine inhibits endothelial cell migration through suppression of the Rho-mediated pathway." Molecular Cancer Therapeutics, (2006), vol. 12, pp. 3130-3138.
Ho, P et al. "Inhibition of human vascular endothelial cells proliferation by terbinafine." Int J Cancer, (2004), vol. 111, pp. 51-59.
Hoyme, H.E. et al. "Prenatal cocaine exposure and fetal vascular disruption." Pediatrics, (1990), vol. 85, pp. 743-747.
James, D. et al. "Expansion and maintenance of human embryonic stem cell-derived endothelial cells by TGFbeta inhibition is ld1 dependent." Nat Biotechnol, (2010), vol. 28, pp. 161-166.
Kadokawa, Yuzo et al. "Expression Pattern of E-and P-Cadherin in Mouse Embryos and Uteri during the Periimplantation Period." Develop, Growth & Differ., (1989), vol. 31, pp. 23-30.
Kalin, R. E. et al. "An in vivo chemical library screen in Xenopus tadpoles reveals novel pathways involved in angiogenesis and lymphangiogenesis." Blood, (2009), vol. 114, pp. 1110-1122.
Kleinstreuer, N. C. et al. "Environmental impact on vascular development predicted by high-throughput screening." Environ Health Perspect, (2011), vol. 119, pp. 1596-1603.
Koop, E. A. et al. "Receptor protein tyrosine phosphatase mu expression as a marker for endothelial cell heterogeneity; analysis

(56) References Cited

OTHER PUBLICATIONS of RPTPmu gene expression using LacZ knock-in mice." Int J Dev Biol, (2003), vol. 47, pp. 345-354.
Kraehenbuehl, T.P. et al. "Human embryonic stem cell-derived microvascular grafts for cardiac tissue preservation after myocardial infarction." Biomaterials, (2011), vol. 32, doi:doi:10.1016/j.biomaterials.2010.10.005, pp. 1102-1109, XP027514839.
Kubo, H. et al. "The bloody fate of endothelial stem cells." Genes Dev, (2003), vol. 17, pp. 322-329.
Kume, T. "Specification of arterial, venous, and lymphatic endothelial cells during embryonic development." Histol Histopathol, (2010), vol. 25, pp. 637-646.
Lamont, R. E. et al. "MAPping out arteries and veins." Science's STKE, (2006), p. E39.
Lee S. H. et al. "Use of directly molded poly(methyl methacrylate) channels for microfluidic applications." Lab Chip, (2010), vol. 10, pp. 3300-3306.
Lee, W. S. et al. "In vitro and in vivo studies of the anticancer action of terbinafine in human cancer cell lines: G0/G1 p53-associated cell cycle arrest." Int J Cancer, (2003), vol. 106, doi:doi:10.1002/ijc.11194, pp. 125-137, XP055041241.
Levenberg, S. et al. "Endothelial cells derived from human embryonic stem cells." Proc Natl Acad Sci USA, (2002), vol. 99, doi:doi:10.1073/pnas.032074999, pp. 4391-4396, XP002980825.
Levine, E. et al. "Selective disruption of E-cadherin function in early Xenopus embryos by a dominant negative mutant." Development, (1994), vol. 120, pp. 901-909.
Li, Z. et al. "Functional and transcriptional characterization of human embryonic stem cell-derived endothelial cells for treatment of myocardial infarction." PLOS ONE, (2009), vol. 4, p. E8443.
Louden, C. et al. "Biomarkers and mechanisms of drug-induced vascular injury in non-rodents." Toxicologic Pathology, (2006), vol. 34, pp. 19-26.
Lu, S. J. et al. "Generation of functional hemangioblasts from human embryonic stem cells." Nat Methods, (2007), vol. 4, doi:doi:10.1038/nmeth1041, pp. 501-509, XP008133153.
Maia, J. et al. "VEGF-Functionalized Dextran Has Longer Intracellular Bioactivity than VEGF in Endothelial Cells." Biomacromolecules, (2012), vol. 13, pp. 2906-2916.
Malek, A. M. et al. "Hemodynamic shear stress and its role in atherosclerosis." JAMA, (1999), vol. 282, pp. 2035-2042.
Metallo, Christian M. et al. "The response of human embryonic stem cell-derived endothelial cells to shear stress." Biotechnology and Bioengineering, vol. 100, No. 4, Jul. 2008 (Jul. 2008), pp. 830-837, XP055143814.
Nikmanesh, M. et al. "Heparan sulfate proteoglycan mediates shear stress-induced endothelial gene expression in mouse embryonic stem cell-derived endothelial cells." Biotechnol Bioeng, (2012), vol. 109, pp. 583-594.
Nourse, M.B. et al. "VEGF Induces Differentiation of Functional Endothelium From Human Embryonic Stem Cells: Implications for Tissue Engineering." Arterioscler Thromb Vasc Biol, (2010), vol. 30, doi:doi:10.1161/ATVBAHA.109.194233, pp. 80-89, XP055163817.
Obi S. et al. "Shear stress induces arterial differentiation of bone marrow-derived endothelial progenitor cells." Micro-Nanomechatronics and Human Science, 2009. MHS 2009. International Symposium on, IEEE, Piscataway, NJ, USA, Nov. 9, 2009 (Nov. 9, 2009), pp. 650-655, XP031579353, ISBN: 978-1-4244-5094-7.
O'Connor, M.D. et al. "Alkaline phosphatase-positive colony formation is a sensitive, specific, and quantitative indicator of undifferentiated human embryonic stem cells." Stem Cells, (2008), vol. 26, pp. 1109-1116.
Olsson, A. K. et al. "VEGF receptor signalling—in control of vascular function." Nat Rev Mol Cell Biol, (2006), vol. 7, pp. 359-371.
Persson, B. et al. "Endotoxin Induces Differentiated Contractile Responses in Porcine Pulmonary Arteries and Veins." Journal of Vascular Research, (2010), vol. 48, pp. 206-211.
Potter, D. R. et al. "The hydrodynamically relevant endothelial cell glycocalyx observed in vivo is absent in vitro." Circulation Research, (2008), vol. 102, pp. 770-776.

* cited by examiner

| Compound | Structure | Class |
|---|---|---|
| Danazol | 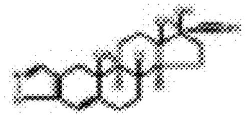 | Hormone |
| Chlorpromazine hydrochloride | 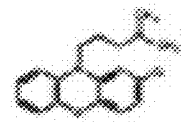 | Dopamine |
| 7-cyclopentyl-5-(4-phenoxy) phenyl-7H-pyrrolo [2, 3-d] pyrimidin-4-ylamine | 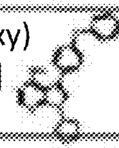 | Phosphorilation |
| Fluphenzine dihydrochloride | 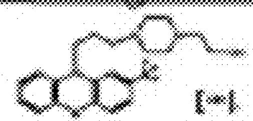 | Dopamine |
| 3'4'-dichlorobenzamil | 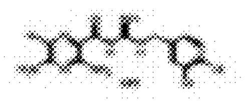 | Ion pump |
| Ellipticine | 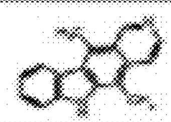 | Cell cycle |

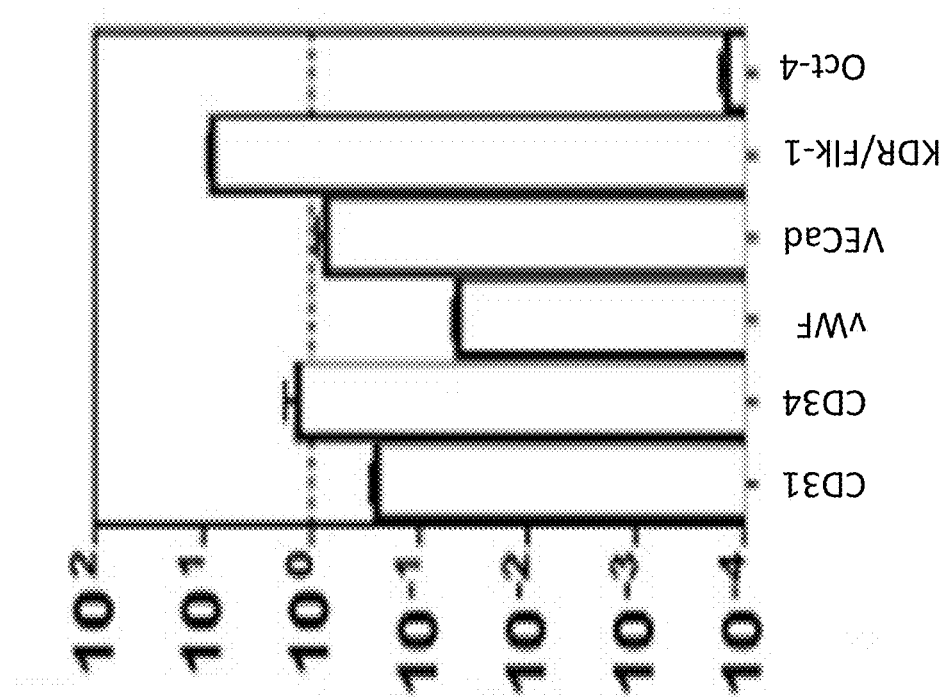

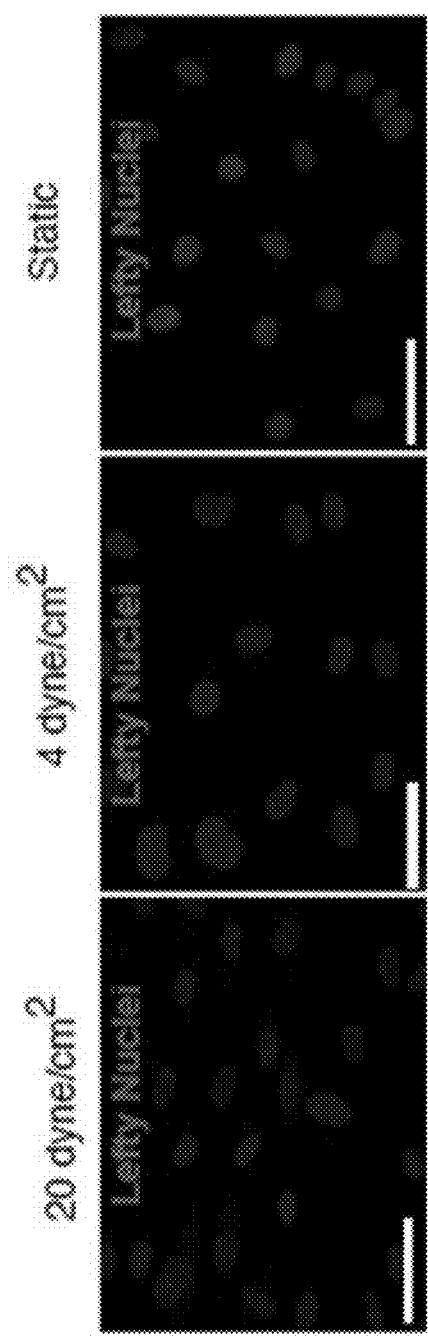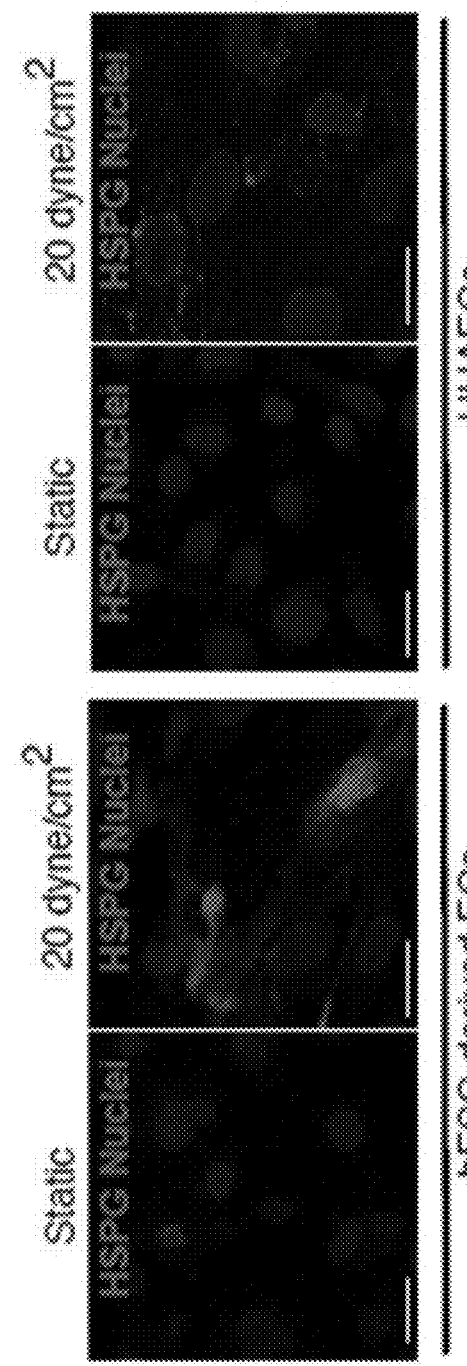
FIG. 13A
FIG. 13B

DIFFERENTIATED CELL POPULATION OF ENDOTHELIAL CELLS DERIVED FROM HUMAN PLURIPOTENT STEM CELLS, COMPOSITION, SYSTEM, KIT AND USES THEREOF

CROSS-REFERENCE TO RELATED PATENT APPLICATIONS

This application is a divisional application of U.S. application Ser. No. 14/651,548, filed Jun. 11, 2015, which is a U.S. National Phase Application under 35 U.S.C. § 371 of International Patent Application No. PCT//IB2013/061110, filed Dec. 18, 2013, and claims the priority of PT 106699, filed Dec. 18, 2012, all of which are incorporated by reference in their entireties. The International Application was published on Jun. 26, 2014 as International Publication No. WO 2014/097192 A2.

TECHNICAL FILED

The present disclosure relates to a differentiated cell population of endothelial cells derived from human pluripotent stem cells. The present invention also relates to a composition, a system and a kit comprising those cells and uses thereof.

BACKGROUND

The development of new technologies and tools for the rapid toxicological profiling of chemical/pharmaceutical substances, at cellular levels, are of great need to reduce and refine the use of animals in research. Vascular cells control the permeability of blood vessels, inflammation and immunity, cell growth, among other key functions, which have an important impact in the homeostasis of the human being.

Vascular cells derived from human pluripotent stem cells (hPSCs) represent a potential cell source for vascular kits[1, 2]. The use of "embryonic" ECs may represent an opportunity to screen toxicity of compounds that affect embryonic vasculature. ECs have been derived from human embryonic stem cells (hESCs) using several methodologies such as embryoid bodies (EBs) which recapitulates in vivo embryogenesis[3, 4], a mixture of EBs with 2D or 3D culture systems[1, 5-7] and co-culture with cell lines[8-10].

However, there is no report showing the specification of hESC-derived ECs into arterial, venous or lymphatic sub-phenotypes either in vitro or after transplantation in animal models. This is important for the development of vascular kits to assess vascular toxicity and to target specific vascular vessels for therapeutic use. During embryonic development, specification into arterial-, venous- or lymphatic-derived ECs is defined at gene level and is mediated by several signaling pathways including VEGF, Notch and ephrin before circulation begins[11, 12]. Studies in mouse have shown that ephrin B2 and its receptor ephB4 are differentially expressed in arterial and venous ECs, respectively, before the onset of circulation in the developing embryo[13]. After the onset of the circulation, the distinct hemodynamic forces found in arteries and veins, such as blood flow rate, direction and pressure, can be a major driver in the specification and maturation of the ECs[11, 12]. Indeed, hemodynamic forces as shear stress have the capacity to program or redirect the specification of blood vessel type during development[11, 12].

The development of vascular kits requires the development of microfluidic platforms to screen multiple compounds in a high-throughput while the cells are exposed to shear stress forces typically found in vivo. Only recently, researchers have replicated the circular cross-section of blood vessels in microfluidic devices[14-16]. However, so far, these tools have not been used in the context of drug screening/toxicology assessment.

SUMMARY

The present disclosure relates to a differentiated cell population of endothelial cells derived from human pluripotent stem cells wherein a portion of the said endothelial cells express ephrin B2. These differentiated cell population is particular useful in the screening embryonic vascular toxicity or therapeutic compounds.

The pluripotent stem cells used in the present disclosure are obtained without having to recur to a method necessarily involving the destruction of human embryos, namely with the use of iPS cells.

Better results could be achieved when the portion of differentiated cell population of endothelial cells derived from human pluripotent stem cells has at least 20% of ephrin B2, preferably at least 25%, 35%, 40%, 45%, 50%, 55%, 60%, 65%, 70%, 75%, 85%, 90%, 95%, 100%, more preferably 50% to 75% of the cells express ephrin B2. These cells may have the ability to form cord-like structures when cultured in the basement membrane Martrigel.

In order to optimize the useful in the screening embryonic vascular toxicity or therapeutic compounds, the cell population of endothelial cells may further express the following marker Ac-LDL.

In order to optimize the useful in the screening embryonic vascular toxicity or therapeutic compounds, the cell population of endothelial cells may further express one of the following markers: vWF, CD31, CD34, vascular endothelial cadherin, Flk-1/KDR.

In order to optimize the useful in the screening embryonic vascular toxicity or therapeutic compounds, the cell population of endothelial cells may has a high expression of one of the following arterial endothelial cell genes: jagged 1—JAG1, jagged 2—JAG2, ephrin B1, Hey-2.

In order to optimize the useful in the screening embryonic vascular toxicity or therapeutic compounds, the cell population of endothelial cells may has a high expression of one of the following arterial endothelial cell genes: receptor protein tyrosine phosphatase, T-cell acute lymphocyte leukemia, N-cadherin, angiopoietin 1, DNA-binding protein inhibitor ID-1.

In order to optimize the useful in the screening embryonic vascular toxicity or therapeutic compounds, the cell population of endothelial cells may has a low expression of venous genes such as EphB4, lefty-A and lefty-B.

Other aspect of the present disclosure is related with a differentiated cell population of endothelial cells derived from human pluripotent stem cells wherein a portion of the said endothelial cells express: receptor protein tyrosine phosphatase, T-cell acute lymphocyte leukemia, N-cadherin, angiopoietin 1, DNA-binding protein inhibitor ID-1. These differentiated cell population is particular useful in the screening embryonic vascular toxicity or therapeutic compounds.

Another aspect of the present disclosure is differentiated cell population of endothelial cells derived from human pluripotent stem cells wherein a portion of the said endothelial cells express at least one of the following markers: vWF, CD31, CD34, vascular endothelial cadherin (VE-CAD), Flk-1/KDR for the use in the screening embryonic vascular toxicity or therapeutic compounds.

Better results could be achieved when the portion of differentiated cell population of endothelial cells derived from human pluripotent stem cells has at least 20% of the said cells express at least one of the following markers: vWF, CD31, CD34, vascular endothelial cadherin (VE-CAD), Flk-1/KDR, preferably at least 25%, 35%, 40%, 45%, 50%, 55%, 60%, 65%, 70%, 75%, 85%, 90%, 95%, 100%. These cells may have the ability to form cord-like structures when cultured in the basement membrane Martrigel.

Other aspect is the use in medicine of the differentiated cell population of endothelial cells derived from human pluripotent stem cells. Namely, using the cell population in the screening embryonic vascular toxicity or therapeutic compounds.

Other aspect is a composition comprising the cell population above described, namely a pharmaceutical composition.

Other aspect is a kit for use in screening vascular toxicity or therapeutic compounds comprising the cell population above described.

Other aspect is a fluidic system for use in screening therapeutic drugs or embryonic vascular toxicity, comprising a channel with a millimeter or micrometer dimension and a differentiated cell population of endothelial cells as described in the present disclosure.

In an embodiment of the system, the cells cultured under physiological shear stress are cells seeded and exposed to the media flow, and may produce glycocalyx. In another embodiment the media flow of the system may be above 1 dyne/cm2, preferably is above 4 dyne/cm2, preferably 20 dyne/cm2.

In an embodiment of the system, the channel may comprises poly(dimethylsiloxane).

In other preferred embodiment of the system channel may has:
a length of 0.1-1.0 cm, preferably 0.5 cm;
and an inner diameter higher than 200 µm, more preferably 200-900 µm, more preferably 400-600 µm.

In another embodiment the system may further comprises plasma such as argon. Preferably, the system may further comprises gelatin, collagen, or fibronectin, or fibrin, or matrigel or mixtures thereof.

In another embodiment the media flow of the system is above 1 dyne/cm2, preferably is above 4 dyne/cm2, preferably 20 dyne/cm2.

In another embodiment, the cells of the system above described may be the cell population above described.

Other aspect is a device for use in screening vascular toxicity or therapeutic compounds comprising: endothelial cells derived from human pluripotent stem cells as above described; and a fluidic system as above described. The device could be use in screening embryonic vascular toxicity or therapeutic compounds, or in screening embryonic arterial endothelial cell toxicity or therapeutic compounds or in screening embryonic arterial endothelial cell toxicity or therapeutic compounds in conditions that mimic the in vivo conditions, or use in the screening of antitumor or anticancer drugs.

In an embodiment, the compounds of the device may be selected from the following group: danazol, chlorpromazine hydrochloride, ellipticine, 3',4'-dichlorobenzamil, fluphenazine dihydrochloride, 7-cyclopentyl-5-(4-phenoxy) phenyl-7H-pyrrolo[2,3-d]pyrimidin-4-ylamine, among others.

Other aspect is a method of promoting the viability of arterial endothelial cells comprising differentiation from human pluripotent stem cells with the following steps:
culturing embryoid bodies in suspension for 4 days in differentiation medium comprising VEGF165;
seeding the said embryoid bodies in a cell culture and sequentially exposing the cells to VEGF plus thymosin β4 for 3 days and VEGF plus thymosin β for 4 days and SB431542 for 11 days;
isolating CD31+ cells and culturing these cells in endothelial cell medium containing SB431542.

The reported methodology applies where the pluripotent stem cells are induced pluripotent cells that do not require the death of the embryo.

In an embodiment, of the method the human pluripotent stem cells were differentiated in conditions that Shh and Notch signaling is activated.

In other embodiment, of the method the human pluripotent stem cells were differentiated in the presence of DLL4 and purmorphamine preferably, 100 ng/mL of DLL4, and 1 µM of purmorphamine.

In other embodiment, of the method the predetermined conditions comprise a seeding density of 15,000 cells per cm2 in a gelatin-coated dish.

In other embodiment, of the method further comprising adding to the cell population of CD31+, SB431542 with a concentration higher than 1 µM, preferably 5 µM-10 µM.

In other embodiment, of the method further comprising adding to the cell population of CD31+ miRNAs by a transfection agent. Preferably the said agent may be a nanoparticle. In other embodiment, of the method the said endothelial cell medium for culturing CD31+ cells has at least one of the following growth factors: VEGF, PDGF, angiopoietin (Ang), ephrin (Eph), fibroblast growth factor (FGF), placental growth factor (PlGF), transforming growth factor β-1 [(TGF)-β-1], cytokines, erythropoietin, thrombopoietin, transferring, insulin, stem cell factor (SCF), granulocyte colony-stimulating factor (G-CSF), granulocyte-macrophage colony stimulating factor (GM-CSF) and their mixtures.

In other embodiment, of the method further comprising co-culturing CD31+ cells with arterial endothelial cells.

All the embodiments described are obviously combinable.

The present disclosure also described the combination of arterial ECs derived from human pluripotent stem cells with a microfluidic system to create a vascular kit for high-throughput drug screening and/or toxicology analysis. This technology may find particular use for the identification of drugs that may have a fetal cytotoxic effect.

DESCRIPTION OF THE DRAWINGS

The following figures provide preferred embodiments for illustrating the description and should not be seen as limiting the scope of invention.

FIG. 1A: EC marker expression and functionality of hESC-derived ECs. In all figures bar corresponds to 50 µm. FIG. 1B: Microarray analysis showing that hESC-derived ECs share many arterial genes as shown in hUAECs and hAECs. The list of genes correlates with the heat map. FIG. 1C: qRT-PCR analysis for arterial and venous markers in hESC-derived ECs at passage 4. The expression of the same genes for hUAECs and hAECs is displayed. Results are mean±SEM (n=4). FIG. 1D: Expression of venous and arterial genes in CD31$^+$ cells differentiated in basal media or media containing both Shh and Notch activators (purmorphamine, 1 μM and DLL4, 100 ng/mL). Results are mean±SEM (n=4). FIG. 1E: Expression of Notch and Shh genes in CD31$^+$ cells after isolation. Results are mean±SEM (n=4). FIG. 1F: Expression of arterial marker EphB2 in CD31+ cells after treatment with chemical activators and inhibitors of Shh and Notch signaling pathways. Shh inhibitor is cyclopamine (5 μM) and Shh activator is purmorphamine (1 μM). Notch inhibitor is L685458 (1 μM) and Notch activator is DLL4 (100 ng/mL). FIG. 1G: qRT-PCR analysis for embryonic endothelial markers in hESC-derived ECs at passage 4, hUAECs, mouse embryonic ECs at day 12.5 (mAEC E12.5) and postnatal day 1 (p1). FIG. 1H: Microarray analysis showing that hESC-derived ECs express embryonic genes not present in fetal hUAECs or adult hAECs. The list of genes correlates with the heat map. FIG. 1I: Variation of intracellular $Ca^{2+}$ in FURA-2-loaded cultured hESC-derived ECs, HUAECs or HUVECs in response to several agonists. Traces are representative of 6 independent experiments for each condition. In FIGS. 1C-1F, gene expression was normalized by the expression of GAPDH. In all figures, *$P<0.05$, $P<0.01$, *$P<0.001$.

FIG. 2A: Cell alignment and expression of endothelial (VECad) and arterial (EphB2) markers in hESC-derived ECs. Bar corresponds to 50 μm. FIG. 2B: Flow cytometry analysis of hESC-derived ECs cultured for 7 days in static and flow (20 dyne/cm2) conditions. Percentages of positive cells were calculated based in the isotype controls (grey plot) and are shown in each histogram plot. EphB2 expression on HUAECs cultured under static or flow conditions are also shown for reference. FIG. 2C: qRT-PCR analysis for venous and arterial markers in hESC-derived ECs (data was normalized by the housekeeping gene GAPDH) cultured for 7 days in static or flow (4 or 20 dyne/cm2) conditions. Results are mean±SEM (n=4). FIG. 2D: Expression of HSPG in hESC-derived ECs and HUAECs in static and flow conditions for 7 days at 20 dyne/cm2. Bar corresponds to 50 μm.

FIG. 3A: Expression and localization of VECad in hESC-derived cells and HUAECs cultured in medium supplemented with terbinafine. Cells were cultured under flow (20 dyne/cm2), in medium without terbinafine, for 7 days, after which the cells were cultured in medium supplemented with terbinafine (0.1 or 1 μM) for 24 h, under flow. Bar corresponds to 50 μm. FIG. 3B: Expression of genes involved in inflammation (ICAM-1; E-selectin), oxidative stress (HO-1), vascular modulation (eNOS) and vascular injury (DDAH1 and DDAH2; genes that encode for enzymes that degrade ADMA) in hESC-derived ECs and HUAECs cultured in medium supplemented with terbinafine. Results are mean±SEM (n=4). *$P<0.05$, $P<0.01$, *$P<0.001$. FIG. 3C: Quantification of ADMA and vWF-pp:vWF by ELISA in hESC-derived ECs and HUAECs.

FIG. 4A: Schematic representation of the HTS assay. FIG. 4B: Small molecules identified after the analysis of the primary screen. The hits have higher cytotoxicity against hESC-derived ECs than HUAECs. FIG. 4C: Dose-response curve for HUAECs and hESC-derived ECs exposed to 7-Cyclo. Results are mean±SEM (n=4).

FIG. 5A: Macroscopic view of the PDMS microfluidic system (the microchannels have a diameter of 900 μm and an average length of 0.5 cm) and fluorescent images of microchannel cross-sections showing that ECs can populate the inner surface of the microfluidic channel after 48 h and be stable for at least 7 days at 20 dyne/cm2. Scale bars are 50 μm. FIG. 5B: Cell organization and morphology of hESC-derived ECs and HUAECs before and after incubation with 7-Cylo for 24 h in a microfluidic system. Bar corresponds to 50 μm. FIG. 5C: Expression of genes involved in inflammation (ICAM-1; E-selectin), oxidative stress sensing (HO-1), vascular modulation (eNOS) and vascular injury sensing (DDAH1 and DDAH2) in hESC-derived ECs and HUAECs after 24 h incubation with 0 or 1 μM of 7-Cyclo. Results are mean±SEM (n=4). *$P<0.05$, *$P<0.001$, **$P<0.0001$. FIG. 5D: Quantification of ADMA and vWFpp:vWF by ELISA in hESC-derived ECs and HUAECs after 24 h incubation with 1 μM of 7-Cylo. Results are mean±SEM (n=6). *$P<0.05$, $P<0.01$, **$P<0.0001$.

FIG. 6A: Expression of genes involved in inflammation (ICAM-1; E-selectin), oxidative stress sensing (HO-1), vascular modulation (eNOS) and vascular injury sensing (DDAH2) in mouse aortic endothelial cells (mAEC) at E12.5 and p.1 (post-natal day1) after 24 h incubation with 0 or 1 μM of 7-Cyclo. Results are mean±SEM (n=4). $P<0.01$, *$P<0.001$. FIG. 6B: Microarray analysis showing the expression of tyrosine kinases in hESC-derived ECs, hUAECs and hAECs. Some of the tyrosine kinases are higher expressed in hESC-derived ECs than in hUAECs or hAECs (zoom of the microarray). FIG. 6C: Validation of the expression of tyrosine kinases by qRT-PCR. Gene expression was normalized by the expression of GAPDH. Results are mean±SEM (n=4). *$P<0.05$. FIG. 6D: Kinase activity on hESC-derived ECs and HUAECs after incubation with variable doses of 7-Cyclo. Luminescence is inversely related to kinase activity. Results are mean±SEM (n=6). $P<0.01$, *$P<0.001$.

FIG. 7A-7E: Induction of endothelial differentiation on hPSCs. FIG. 7A: Scheme showing the differentiation protocol. FIG. 7B: Expression of CD31 marker, as quantified by FACS, in hESCs differentiated for 18 days in media supplemented with VEGF165, Tβ4 and SB431542 at different times, or only media without supplements. Values indicate mean±SEM from 3 independent experiments. FIG. 7C: Gene expression on hESCs during the induction of endothelial differentiation. Gene expression was evaluated by qRT-PCR and the values normalized by the corresponding gene expression observed in HUVECs, with the exception of Oct-4, which was normalized by the corresponding gene expression in undifferentiated hESCs. Results are mean±SEM (n=4). FIG. 7D: Gene expression on hESC-derived ECs. hESC-derived ECs were obtained from CD31+ cells isolated by MACS and differentiated for 3 passages (approximately 22 days after cell seeding). Gene expression was normalized as in FIG. 7C. FIG. 7E: Flow cytometry analysis of hESC-derived ECs. Percentages of positive cells were calculated based in the isotype controls (grey plot) and are shown in each histogram plot.

FIG. 8A: Scheme summarizing the differentiation protocols (Prot1-Prot7). FIG. 8B: Expression of CD31 marker in hESCs differentiated for 18 days. Values indicate mean±SEM from 3 independent experiments. FIG. 8C: Gene expression in hESC-derived EC cells differentiated by some protocols, as evaluated by qRT-PCR. Gene expression in each experimental group was normalized by the corresponding gene expression observed in HUVECs. Results are mean±SEM (n=3-4).

FIG. 9A: Time-course proliferation of hESC-derived ECs. FIG. 9B: hESC-derived ECs (Prot7, passage 3, approximately 22 days after CD31+ cell seeding) have cobblestone morphology and do not express α-SMA, a smooth muscle cell marker. FIG. 9C: Expression of arterial (EphB2) and venous (Lefty) markers in HUVECs and HUAECs. Bar corresponds to 50 μm.

FIG. 10A: Flow cytometry analysis of hIPS-derived ECs. Percentages of positive cells were calculated based in the isotype controls (grey plot) and are shown in each histogram plot. FIG. 10B: EC marker expression and functionality of hESC-derived ECs. In all figures bar corresponds to 50 μm. FIG. 10C: qRT-PCR analysis for EC markers. Vascular gene expression in each experimental group was normalized by the corresponding gene expression observed in HUVECs, with the exception of Oct-4, which was normalized by the corresponding gene expression in undifferentiated hIPS. In the graphs corresponding to vein and arterial gene expression the genes were normalized by the expression of GAPDH. Results are mean±SEM (n=4). *$P<0.05$, $P<0.01$, *$P<0.001$.

FIG. 11A: Scheme summarizing the inductive and spontaneous differentiation protocols. FIG. 11B-11C: Expression of arterial and venous markers in hESCs differentiated for 18 days using the inductive (FIG. 11B) or spontaneous (FIG. 11C) differentiation protocols. Values indicate mean±SEM, n=4. FIG. 11D: Effect of activation and inhibition of Shh and Notch signaling pathways in the expression of EphB2 in CD31+ cells. Shh inhibitor is cyclopamine (5 μM) and Shh activator is purmorphamine (1 μM). Notch inhibitor is L685458 (1 μM) and Notch activator is DLL4 (100 ng/mL).

In FIG. 12A, bar corresponds to 50 μm. In FIG. 12B, results are Mean±SEM (n=3-4).

FIGS. 13A-13B: Effect of physiological shear stress in the subphenotype of hESC-derived ECs. FIG. 13A: Cells cultured under static or flow conditions for 7 days do not express the venous EC marker Lefty. Bar corresponds to 50 μm. FIG. 13B: hESC-derived ECs and HUAECs cultured under static conditions do not express heparan sulfate proteoglycan (HSPG), while both cells express HSPG under flow conditions. Bar corresponds to 50 μm.

DETAILED DESCRIPTION

Figure 1A:
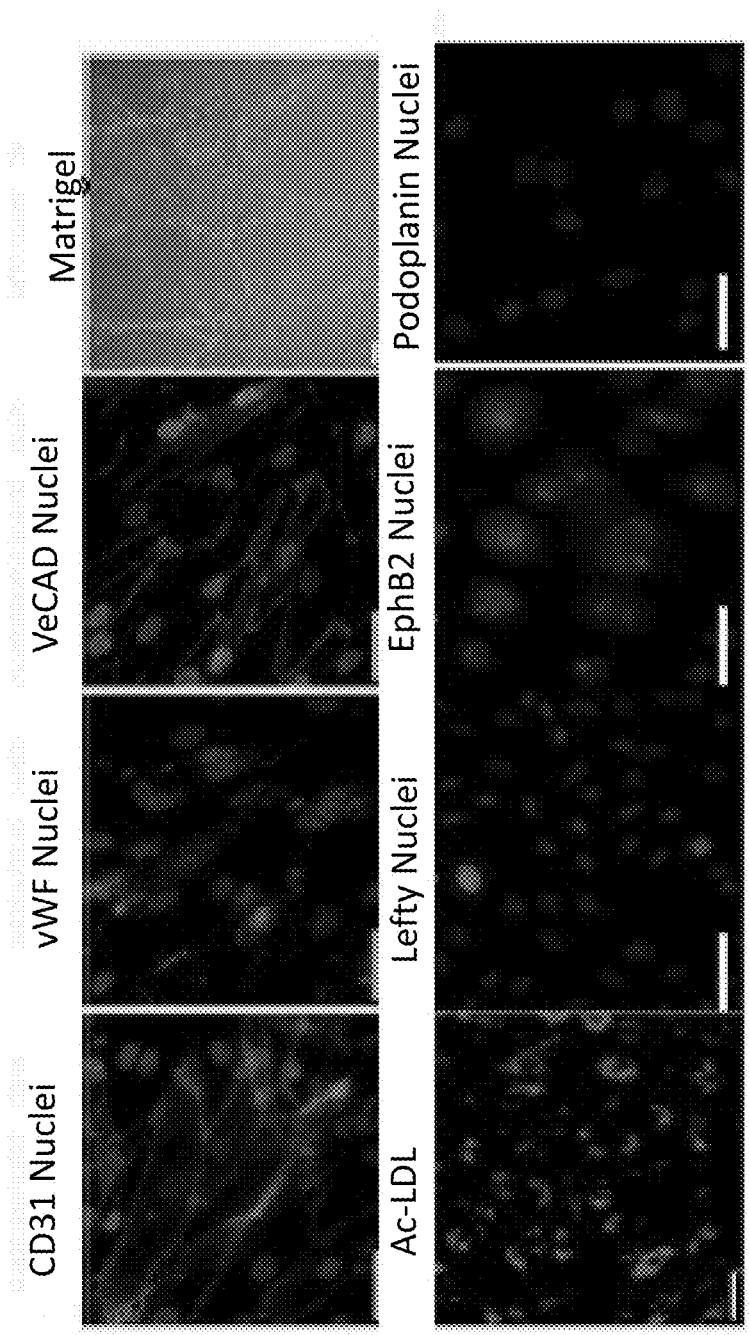
FIGS. 1A-1I: Specification of hPSC-derived ECs into arterial phenotype.

The present disclosure relates to differentiated cell population of endothelial cells derived from human pluripotent stem cells.

The said pluripotent stem cells used in the present invention are obtained without having to recur to a method necessarily involving the destruction of human embryos.

In the present disclosure is presented a platform for the high-throughput screening of compounds that might interfere with embryonic vascular development. Initially, conditions were screened for the differentiation of hPSCs (human pluripotent stem cells) into embryonic arterial ECs followed by their maturation under flow shear stress. In static conditions, arterial ECs express arterial genes such as JAG1, ephrin B1 and Hey-2 and the arterial ephrin receptor B2 (EphB2).

In flow conditions, the cells align in the direction of the flow and further up-regulate the expression of arterial genes. The process is likely mediated by heparan sulfate proteoglycan (HSPG), a component of glycocalyx, which is activated by fluidic shear stress. The utility of embryonic arterial ECs cultured under flow conditions for toxicological assessment was then demonstrated. The higher sensitivity to cytotoxic compounds such as terbinafine of hESC-derived ECs cultured under physiological shear stress than cells cultured in static conditions was shown. Additionally, using a high-throughput assay in combination with in vivo data, was identified the 7-cyclopentyl-5-(4-phenoxy)phenyl-7H-pyrrolo[2,3-d]pyrimidin-4-ylamine (7-Cyclo) as a cytotoxic compound of embryonic ECs.

The disclosed platform is a powerful platform for drug screening and to study embryonic vascular biology under physiologic conditions.

In the disclosed subject matter is described the combination of arterial ECs derived from human pluripotent stem cells with a microfluidic system to create a vascular kit for high-throughput drug screening and toxicology analysis. This technology may find particular use for the identification of drugs that may have a fetal cytotoxic effect. Furthermore, the principles defined in this work may be applied to iPSCs in order to create personalized kits for drug screening.

hPSCs can differentiate into arterial ECs. The ECs were characterized at protein level by the expression of EphB2 and the absence of venous Lefty 1/2 and lymphatic podoplanin markers. At gene level, the cells express most of arterial markers shown by HUAECs and HAECs. The arterial specification is mediated in part by Shh and Notch signaling pathways. Results show that the activation of both pathways is required to enhance arterial specification, as previously shown[47,48,12]. The activation of both Shh and Notch signaling pathways from the very beginning of the differentiation procedure (from day 0 up to day 18; before the isolation of CD31+ cells) increased significantly the percentage of cells (from 18% to 36%) already committed into an arterial sub-phenotype. Furthermore, the specification of hPSCs into arterial ECs largely occurs after the isolation and differentiation of CD31+ cells. The arterial ECs differentiated in this study have an "embryonic" phenotype. Although, a defined set of embryonic EC markers have not been identified so far, in the present disclosure was also identified receptor protein tyrosine phosphatase μ (PT-PRu)[24], T-cell acute lymphocyte leukemia 1 (Tal1)[25,26], and some cadherins[27,28], among others, as putative markers of embryonic ECs, based in gene microarray analyses on human ECs as well as gene expression results in mouse embryonic ECs.

The present disclosure also show that fluidic shear stress enhanced the maturation of arterial ECs, and preferably in the maturation of arterial ECs and in the induction of HSPG (shown by the up regulation in the expression of ephrins (1 and 2), notch receptors (1 to 4), and notch ligands (Jagged1 and delta-like ligand 3) and the induction of HSPG. Previous studies have supported the idea that hemodynamic forces have the capacity to program or redirect the specification of blood vessel type during development[11, 12]. ECs not only have the ability to sense hemodynamic forces, but they have the ability to discriminate between different types of biomechanical stimuli. In other embodiment of the present disclosure, was shown that hESC-derived ECs cultured in flow conditions (20 dyne/cm2) aligned in the direction of the flow and express significantly higher levels of arterial markers. Although not demonstrated, HSPGs may mediate this maturation effect. Recent data demonstrated that HSPG is a mechanosensor mediating shear stress-induced EC differentiation from mouse embryonic stem cell-derived ECs49. HSPG is a part of the endothelial glycocalyx, which is only expressed in flow conditions and absent in static conditions[33]. It is conceivable that HSPGs are physically displaced when exposed to shear and the displacement transmitted to the intracellular machinery. It has been suggested that HSPGs are physically activated (direct or not) to actin and nitric oxide synthase mediating the mechanotransduction process[31]. These intracellular processes may contribute for the maturation of the cells under shear stress.

The results further show that hESC-derived ECs cultured under flow conditions can be used to assess vascular toxicity while showing higher sensitivity to vascular toxic compounds.

For proof of concept was used terbinafine an antifungal drug with anti-angiogenesis and anti-tumoral activity[34, 50]. Terbinafine inhibits endothelial cell migration by inhibiting kinases in the Rho-kinase pathway[34]. Results show that hESC-derived ECs cultured under flow respond to very low concentrations of terbinafine (0.1 µM). This was correlated with an up-regulation of oxidative-sensing and inflammatory genes, down-regulation of genes (DDAH1 and DDAH2) encoding enzymes that degrade an inhibitor (ADMA) of nitric oxide synthase, an increase in the secretion of ADMA and vWF pro-peptide, markers of EC injury.

In this present disclosure was identified an embryonic arterial EC inhibitor, 7-Cyclo, by high-throughput screening, which was further validated by a dose-response study and cell culture under flow conditions. 7-Cyclo is a Src family tyrosine kinase inhibitor. 7-Cyclo (20 µM) has been reported to interfere with angiogenic sprouting and disrupt blood vessel formation in Xenopus embryos, although it was unclear whether such effect was related to the embryonic stage of the vasculature or if any vasculature could have the same consequences[51]. Furthermore, in vitro, 7-Cyclo (1 µM) inhibits HUVECs and lymphatic EC tube formation[51], and it is an inhibitor of lymphangiogenesis[52]. Results indicate that hESC-derived ECs exposed to medium supplemented with 7-Cyclo (1 µM) for 24 h under flow conditions show significant alterations in cell morphology, up-regulation of inflammatory genes, and secretion of vascular injury markers. This effect is higher on hESC-derived ECs than HUAECs. Similar results were obtained for mouse embryonic ECs and post-natal ECs, i.e., mouse embryonic ECs were sensitive to the toxicity of 7-Cyclo while post-natal ECs show no measurable effect against the same compound. Therefore, the microfluidic system formed by hESC-derived arterial ECs is a sensitive platform for embryonic vascular toxicological assessment.

The inhibitory mechanism of 7-Cyclo against embryonic arterial cells involves the inhibition of tyrosine kinases highly expressed in embryonic ECs than in fetal or adult ECs. Results show that embryonic ECs (both human or mouse) express higher levels of tyrosine kinase genes that are susceptible to the inhibitory effect of 7-Cyclo. This might explain the enhanced susceptibility of hESC-derived ECs to the effect of 7-Cyclo. In conclusion, the platform described here is promising for the identification of compounds with embryonic toxicity as well as to study embryonic vascular biology under physiologic conditions.

Methods and Results hESC culture and differentiation. Undifferentiated hESCs (passages 33-36; H9, WiCell, Wisconsin) or hiPSCs K2 (passages 32-35; cord blood derived iPSCs kindly donated by Ulrich Martin) were grown on an inactivated mouse embryonic fibroblast (MEF) feeder layer, as previously described 1, 2. To induce the formation of EBs, the undifferentiated hESCs were treated with 2 mg/mL type IV collagenase (Invitrogen) for 2 h and then transferred (2:1) to low attachment plates (Corning) containing 10 mL of differentiation medium [80% KO-DMEM, 20% fetal bovine serum (FBS, Invitrogen), 0.5% L-glutamine, 0.2% β-mercaptoethanol, 1% nonessential amino acids]. The differentiation medium was supplemented with VEGF165 (50 ng/mL, Prepotech), Tβ4 (100 ng/mL, Caslo) and SB431542 (10 µM, Tocris) according to the following timeline: [(VEGF165)days0-18+(Tβ4)days4-18+(SB431542)days7-18]. After 4 days in suspension, EBs were plated onto 1% gelatin-coated dishes and grown for 14 additional days. Medium was changed every 2-3 days. To evaluate the contribution of Shh and Notch signaling pathways, the differentiation medium was supplemented with one or two of the following agents: 1 µM purmorphamine (Shh activator; Cayman Chemical), 5 µM cyclopamine (Shh inhibitor; Sigma), 100 ng/ml DLL-4 (Notch activator; Prepotech), or 1 µM Y⁻-secretase inhibitor L685458 (Notch inhibitor; Tocris Biosciences) 47.

Isolation of CD31+ cells. CD31+ cells were isolated from differentiated hESCs at day 18 using MACS (Miltenyi Biotec). Isolated cells were grown on petri dishes (1.5×104 cells/cm2) coated with 0.1% gelatin and containing EGM-2 (Lonza) supplemented with SB431542 (10 µM). Cell characterization at gene, protein and functional levels can be found in Supplementary Information. HUVECS and HUAECs (both from Lonza) were used as controls for the differentiation studies. Cells were cultured in EGM-2 media or EGM-MV media (both from Lonza; until passage 5) and the medium changed every 2 days.

Immunofluorescence analysis. Cells were transferred to gelatin-coated slides containing differentiation medium, allowed to attach overnight, and then fixed with 4% paraformaldehyde (Electron Microscopy Sciences) for 15 min at room temperature, or cold methanol (5 min). In some cases cells were directly fixed in IBIDI slides. Cells were blocked with 1% (w/v) BSA and stained for 1 h with anti-human primary antibodies for CD34 (Dako; clone QBend10; 1:20), CD31 (Dako; clone JC70A; 1:20), vWf (Dako; clone F8/86; 1:50), VECad (Santa Cruz Biotech; clone F-8; 1:50), α-SMA (Dako; clone 1A4; 1:50), EphB2 (Santa Cruz Biotech; clone H-83; 1:50), Lefty (Santa Cruz Biotech; clone D-6m; 1:50), Podoplanin (Santa Cruz Biotech; clone E-1; 1:50) and HSPG (US Biological; clone 10E4; 1:100). In each immunofluorescence experiment, an isotype-matched IgG control was used. Binding of primary antibodies to specific cells was detected with anti-mouse IgG Cy3 conjugate (Sigma, 1:50), anti-rabbit Cy3 (Jackson Labs, 1:100)

or anti-goat (alexa488, Molecular Probes, 1:200). If necessary, permeabilization with 0.1% TritonX-100 in PBS was performed. For phalloidin staining, cells were stained with 50 µg/mL FITC-phalloidin (Sigma). Cell nuclei were stained with 4',6'-diamidino-2-phenylindole (DAPI) (Sigma) and the slides examined with either a Zeiss fluorescence microscope or Zeiss LSM 50 confocal microscope. For uptake of Dil-labeled acetylated low-density lipoprotein (Dil-Ac-LDL), cells were incubated with Dil-labeled Ac-LDL (10 µg/mL, Biomedical Technologies) for 4 h at 37° C. After incubation, cells were washed three times in EGM-2, fixed with 4% (w/v) paraformaldehyde for 30 min and visualized in a fluorescent microscope.

Gene and intracellular $Ca^{2+}$ analyses. A detailed methodology for both analyses can be found in the online supplementary information. Preferably, HUVEC, HUAEC or hESC-derived ECs were loaded with Fura-2 calcium fluorescent indicator by incubation with 5 µM of the membrane permeable acetoxymethyl (AM) derivative FURA-2/AM (1 mM in DMSO, Molecular Probes) and 0.06% (w/v) Pluronic F-127 (Sigma), using basal medium (M199, Sigma) as a vehicle (35 µL/well, not supplemented with serum nor antibiotics), for 1 h at 37° C. in 5% $CO_2$ and 90% humidity. Cells were then stimulated with histamine (100 µM, Sigma), $VEGF_{165}$ (100 ng, Prepotech), prostaglandin H2-analogue U46619 (10 µM, Cayman) or thrombin (2U, Sigma). A detailed methodology for the fluorescence acquisition can be found on the online data supplement.

Fluidic shear stress experiments. HESC-derived ECs ($2.6 \times 10^6$ cells/mL), HUAECs, HUVECs were seeded on flow chamber untreated-slides (µ-slide 0.4, luer, IBIDI) and grown until confluence. Using a programmed IBIDI pump with positive pressure, the cell monolayer was perfused with EGM-2 medium for 7 days, at flow rate of 15.1 mL/min (corresponding to shear stress of 20 dyne/cm2), or 3.02 mL/min (corresponding to shear stress of 4 dyne/cm2). After 7 days the flow was stopped, the cells imaged, and then stained or collected for posterior gene analysis. Medium was collected for ELISA assays. In some experiments, cells were cultured in medium supplemented with terbinafine (0.1 µM or 1 µM) (Sigma) for a maximum of 24 h, under shear stress. Static controls were performed in the chamber coated-slides but without flow. The IBIDI slides allow a laminar perfusion in rectangular flow geometry.

For the 7-cyclo studies the flow experiments were carried out in a microfluidic system developed by us. The microfluidic device was obtained using a cylindrical mold of 20 Gauge. Polydimethylsiloxane (PDMS) (Sylgard 184 Silicone elastomere base) was mixed at a 10:1 ratio (w/w) with curing agent (Sylgard 184 Silicon Elastomer Curing Agent) and the solution was poured onto a mold (20 gauge needle laid on a plastic dish) and cured at 80° C. for about 3 h. The microchannel was cut to 0.5 cm length (900 µm inner diameter) and treated with Plasma Clean (Electronic Diener Femto Plasma Surface Technology version 5) for 2 min with argon gas (2 mBar) before immersing it in a solution of 0.1% gelatin. HESC-derived ECs ($20 \times 10^6$ cells/mL) or HUAECs were seeded on PDMS microchannels (3.18 µL cell suspension per channel) devices and grown until confluence. Using a programmed IBIDI pump with positive pressure, the cell monolayer was perfused with EGM-2 medium for 7 days; shear stress of 20 dyne/cm2 (. After 7 days the flow was stopped, the cells imaged, and then stained or collected for posterior gene analysis. Medium was collected for ELISA assays. In some experiments, cells were cultured in medium supplemented with 1 µM 7-cyclo (Sigma) for an additional time of 24 h, under shear stress. Static controls were carried out in the microfluidic system but without flow.

Evaluation of the levels of vascular injury by specific markers. ELISA kits analyzed supernatants collected from the shear stress experiments for vWF and vWFpp (Gen-Probe GTI Diagnostic) and ADMA (Enzo Life Sciences), according to manufacturer's recommendations.

High-throughput screening (HTS). HUAECS (Lonza) and hESC-derived ECs were cultured in EGM-2 medium while human anterior cruciate ligament cells (ACL cells) were cultured in Dulbecco's modified Eagle's medium (DMEM; PAA) supplemented with 10% FBS, 0.2 mM ascorbic acid 2-phosphate magnesium salt (Sigma Aldrich), 100 µM/mL streptomycin and 100 U/mL penicillin (Life Technologies). ACL cells were isolated from patients that have signed an informed consent form, in compliance with the Dutch legislation. The ethical committee of Medisch Spectrum Twente Hospital approved the collection.

The LOPAC library (Sigma-Aldrich) was used to screen embryonic endothelial-specific cytotoxic compounds. The compounds were solubilized in DMSO. The final compound concentration used in the screen was 4.5 µM in a final volume of 200 µL per well (96-well plate). HUAECs, hESC-derived EC and ACL cells were seeded at 16,000 cells/well (HUAECs and hESC-derived ECs) and 5,000 cells/well (ACL cells) and allowed to reach near confluence (approximately two days). After two days, medium was exchanged and test compounds and controls were added to the 96-well plates (all wells contained 0.25% (v/v) DMSO). After 4 days of incubation, cell viability was assessed using a PrestoBlue (Invitrogen) assay. This assay is based on a resazurin-based solution that indicates the reducing power of living cells and therefore measures indirectly their number. For each measurement, cell medium was removed and the PrestoBlue solution (10%) was added for 3 h at 37° C. upon which the absorbance was measured at 560-590 nm. Initially a list of compounds were selected based on their higher cytotoxic to HUAECs (more than 50%) than ACL cells. Then, a list of compounds was selected based on their higher cytotoxicity to hESC-derived ECs (more than 20%) than HUAECs.

The hit compounds obtained from the primary screen were then re-evaluated at eight different concentrations in order to find a dose-response curve. hESC-derived ECs and HUAECs were seeded at 16,000 cells/well (96 well plate), in EGM-2, and allowed to reach sub-confluency. The compounds were serially diluted in DMSO in logarithmic steps, ranging from 0.01 µM to 100 µM and added to the cell culture medium (200 µL per well; EGM-2 medium). Untreated cells were used as control. Cell viability was assessed as described before for the LOPAC library using the PrestoBlue assay.

Statistical analysis. An unpaired t test or one-way ANOVA analysis of variance with Newman-Keuls post-test was performed for statistical tests using software GraphPad Prism™. Results were considered significant when $P<0.05$.

Results:

Derivation of Arterial ECs From hPSCs

Figure 7A:
Figure 7C:
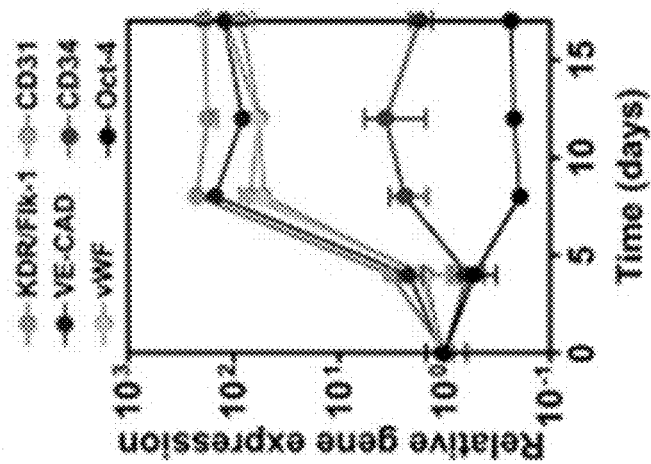
Figure 7B:
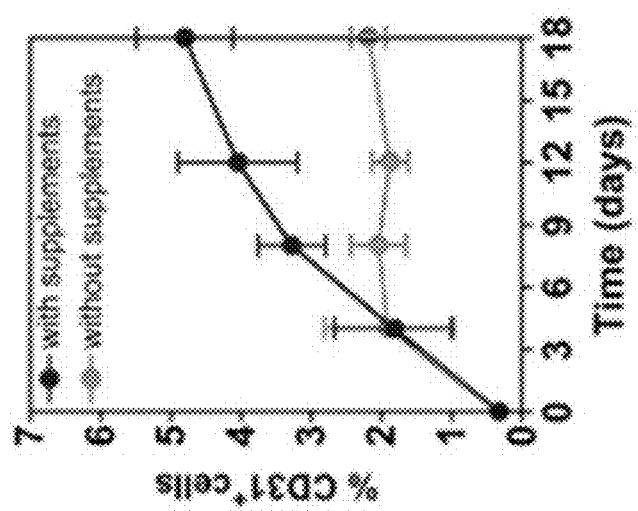
Figure 8A:
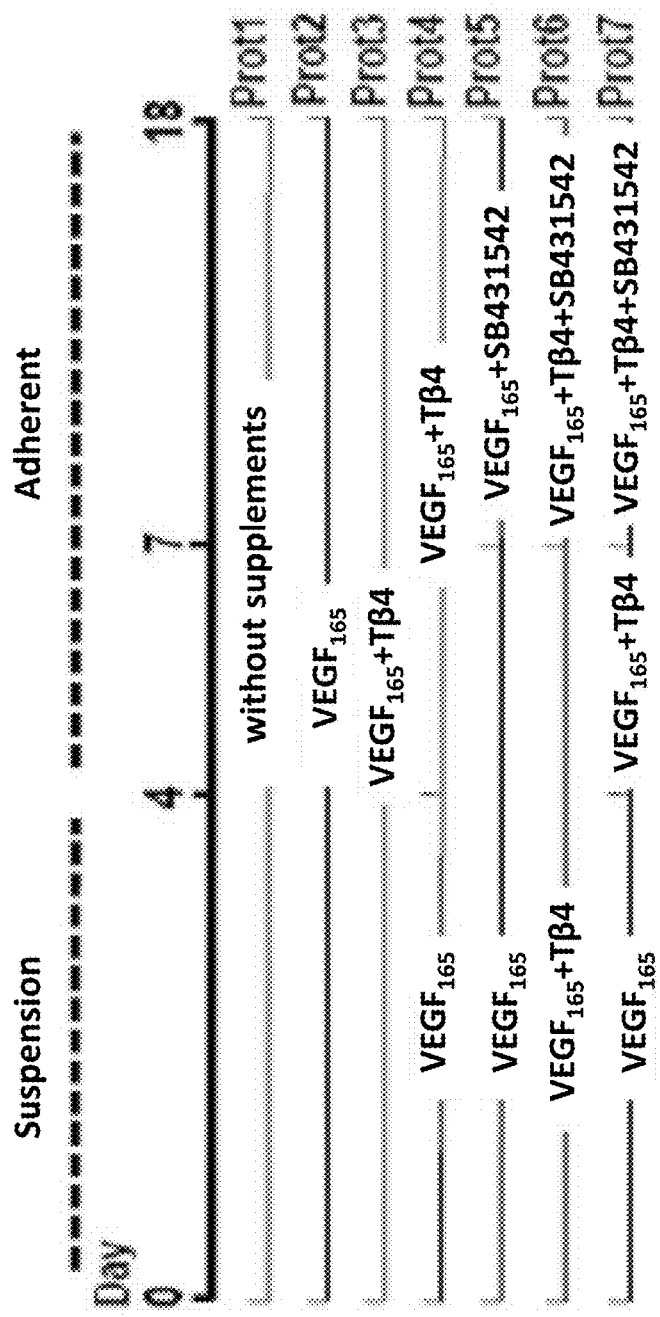
FIGS. 8A-8C: Induction of vascular differentiation on hESCs.
Figure 8B:
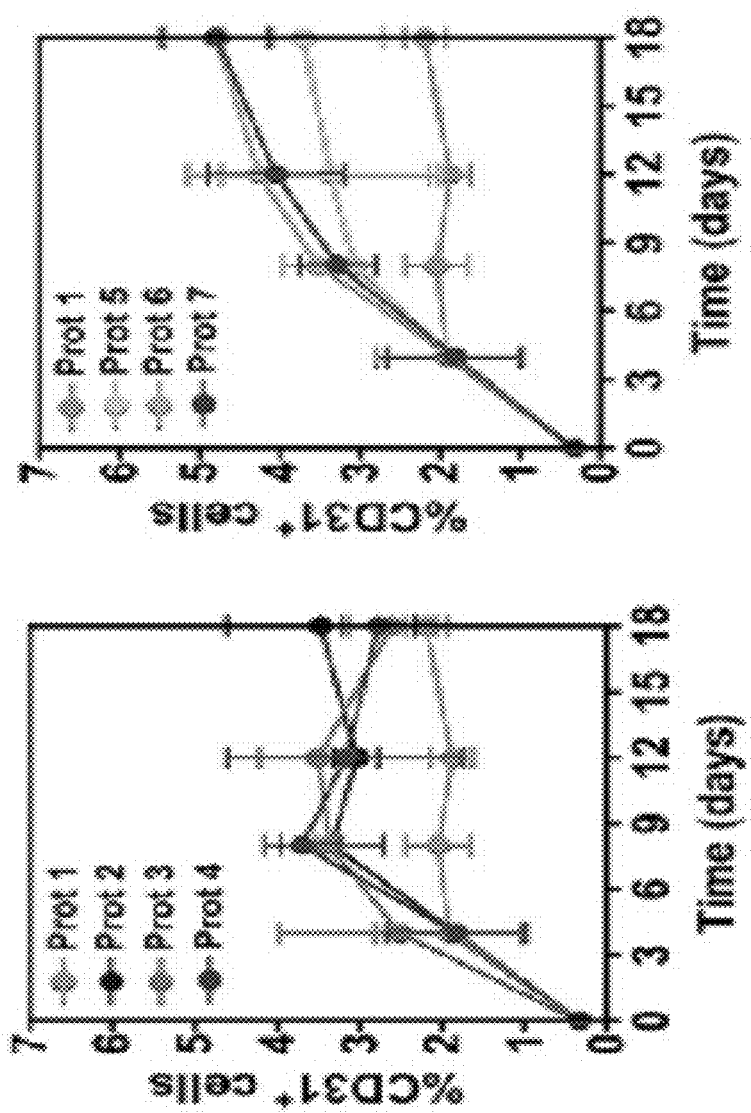

To differentiate hPSCs into arterial ECs several protocols using $VEGF_{165}$[1, 17], thymosin β4 (Tβ4) were screened[18, 19] and TGF-β inhibitor (SB431542)[20] as inductive agents of EC differentiation (FIGS. 7A and 8A). To determine their inductive effect the expression of CD31 marker was examined, which has been previously used to identify embryonic ECs[1], by flow cytometry (FIGS. 7B and 8B). Using the inductive protocol (Prot 7) was possible to obtain approximately 5% of $CD31^+$ at the end of 18 days of differentiation.

Figure 8C:
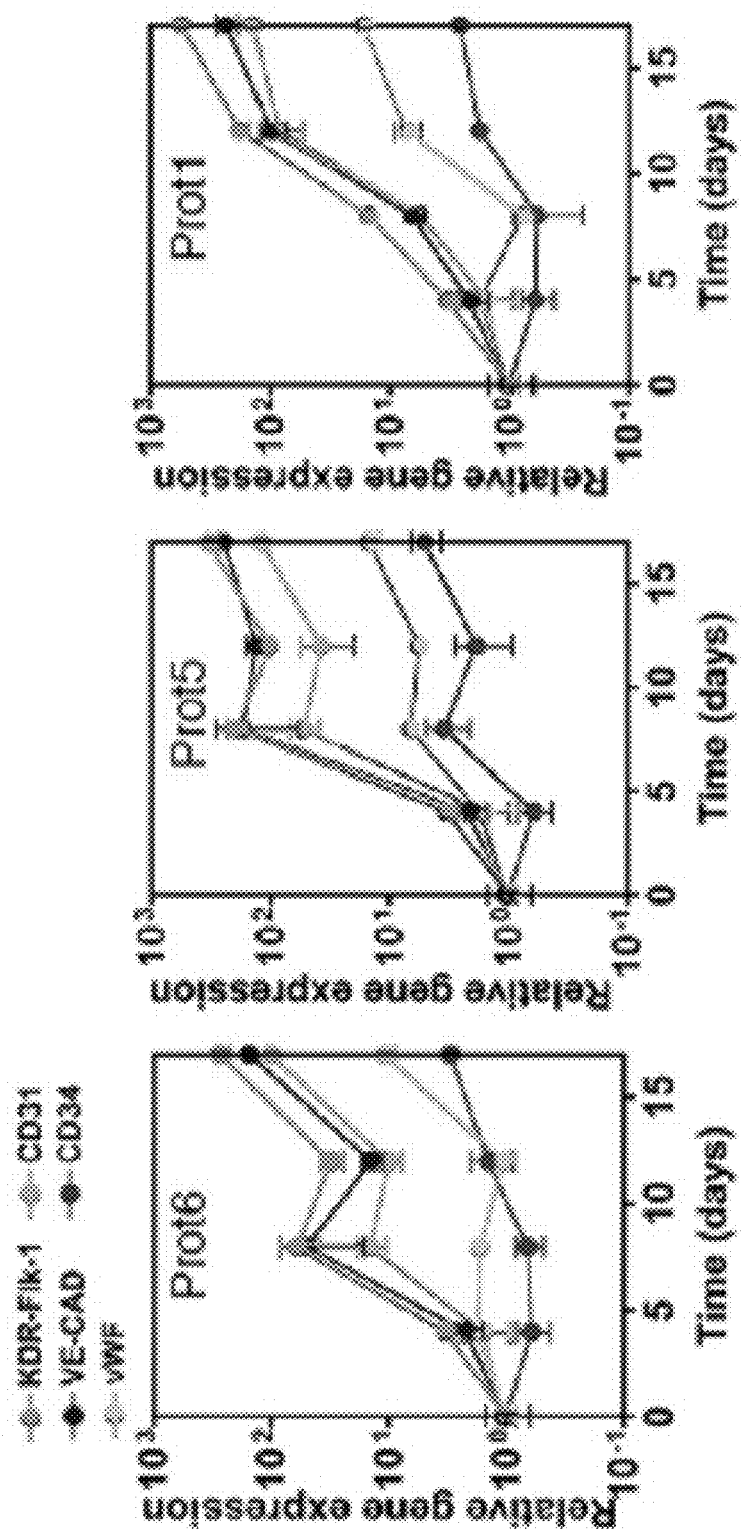

This percentage is two fold higher (P<0.05, n=3) than the one obtained for the spontaneous differentiation of the cells (Prot 1) using classical EB medium (≈2%). The phenotypic analyses were complemented by gene expression analyses by qRT-PCR (FIGS. 7C and 8C).

Figure 7E:
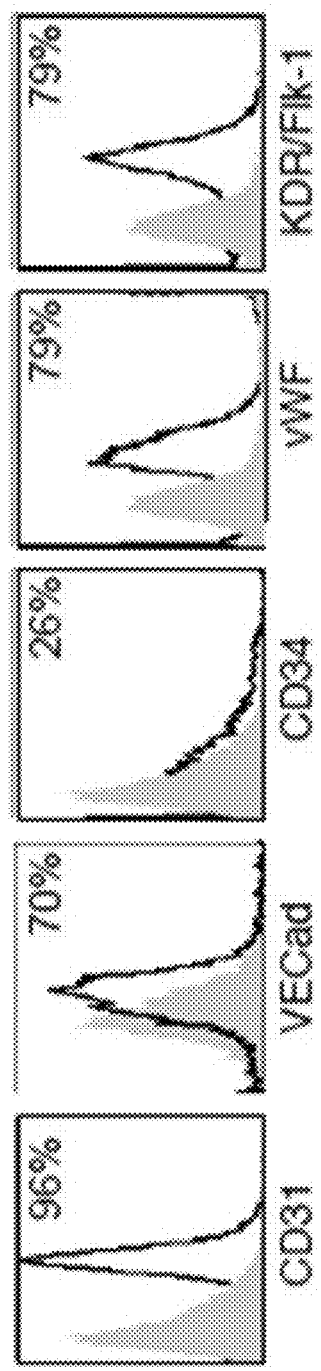
Figure 9A:
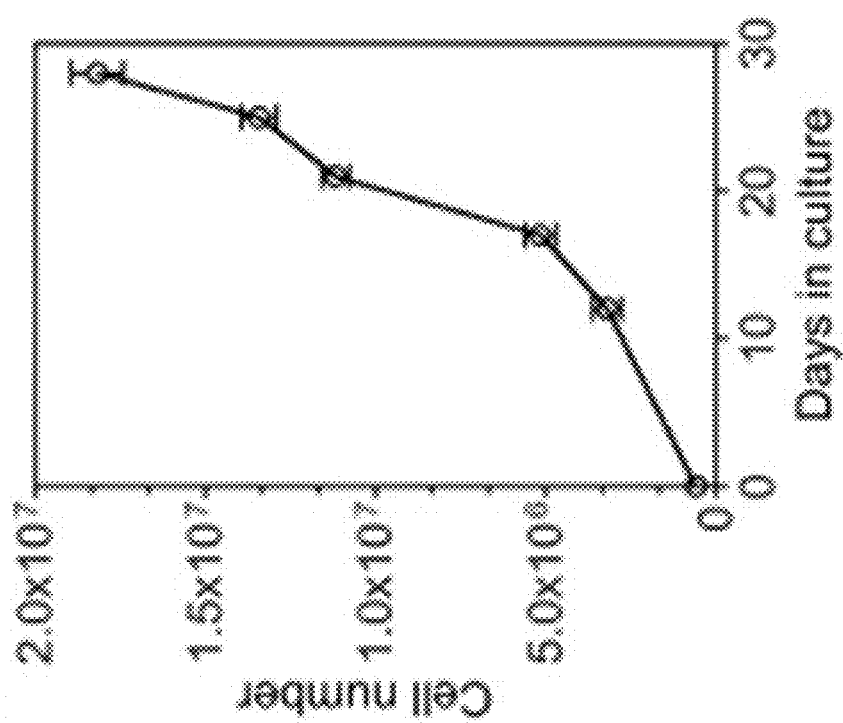
FIGS. 9A-9C: Characterization of hESC-derived ECs, HUVECs and HUAECs.
Figure 9B:
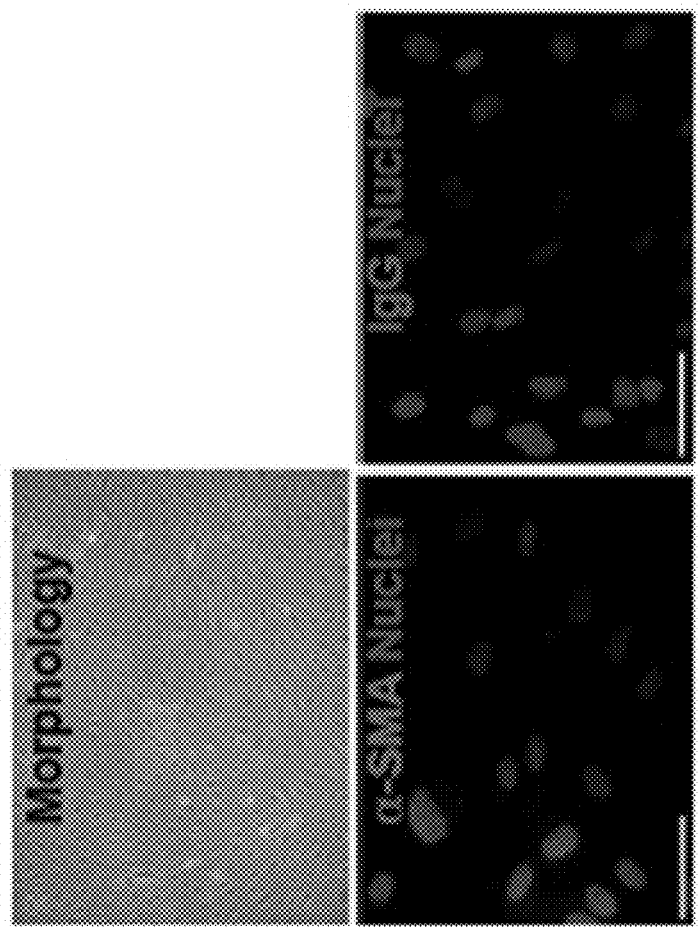

To determine whether CD31+ cells could give rise to ECs, CD31+ cells were isolated by magnetic activated cell sorting (MACS) and cultured in EGM-2 medium supplemented with SB431542 (10 µM) (FIG. 9A). Gene expression analysis in cells differentiated for 3 passages (between 18 and 22 days after cell seeding) indicate that they express CD34, VE-Cad and Flk-1/KDR at the same or higher level as the one found in HUVECs, albeit have lower expression of vWF and CD31 which may indicate different levels of maturation (FIG. 7D). Furthermore, the differentiated cells had low expression of Oct-4 confirming their differentiated state. Flow cytometry and immunocytochemistry analyses show that CD31+ cells cultured for 3 passages expressed high levels of EC markers (FIG. 7E and FIG. 7A). Differentiated CD31+ cells stained positively for VE-Cad at cell-cell adherent junctions and produced vWF (FIG. 1A). In addition, they do not express markers of other mesoderm-derived cell lineages such as the smooth muscle cell marker α-SMA (FIG. 9B). Overall, the results indicate that CD31+ cells give rise to ECs.

Figure 1B:
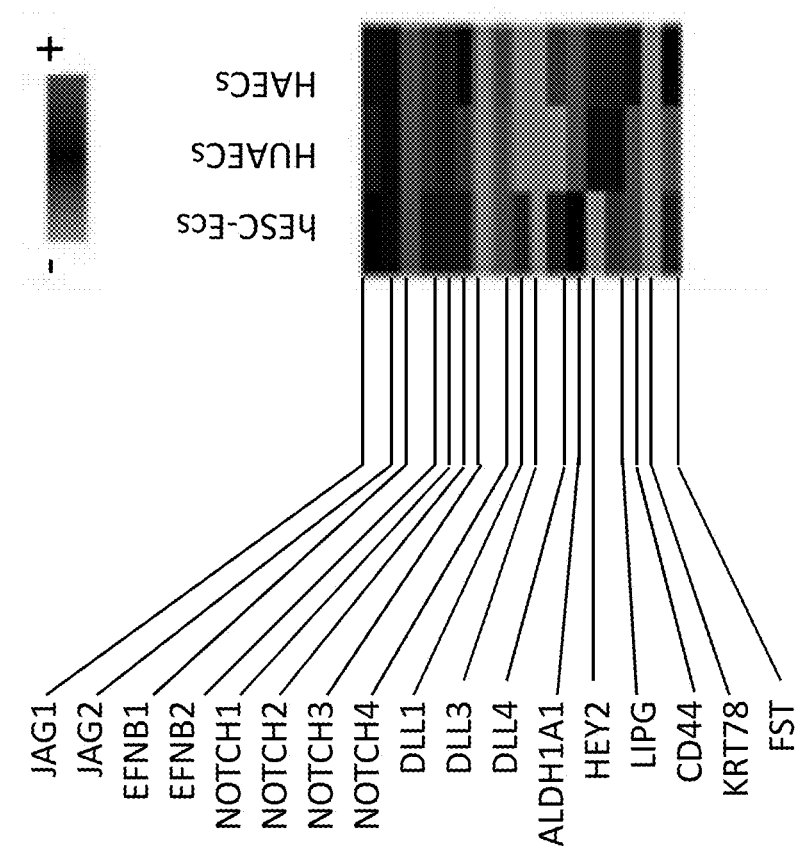
Figure 1C:
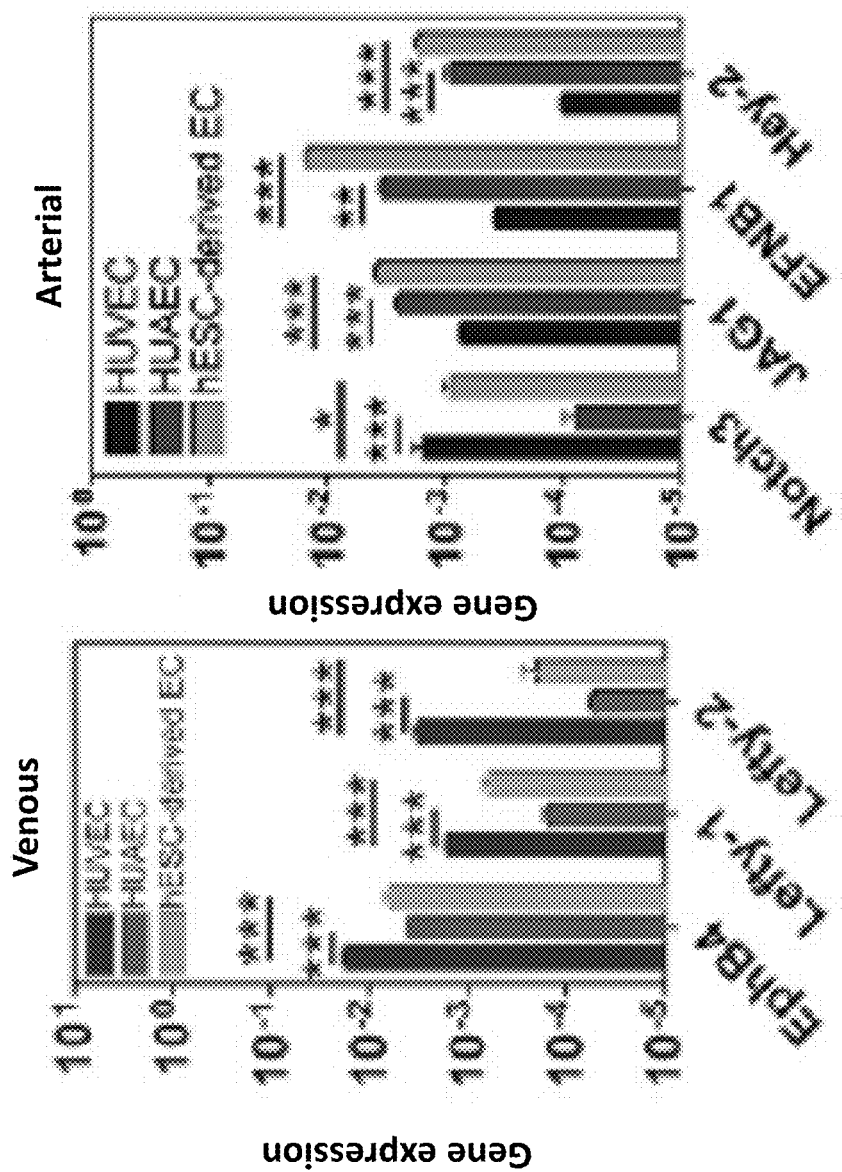
Figure 9C:
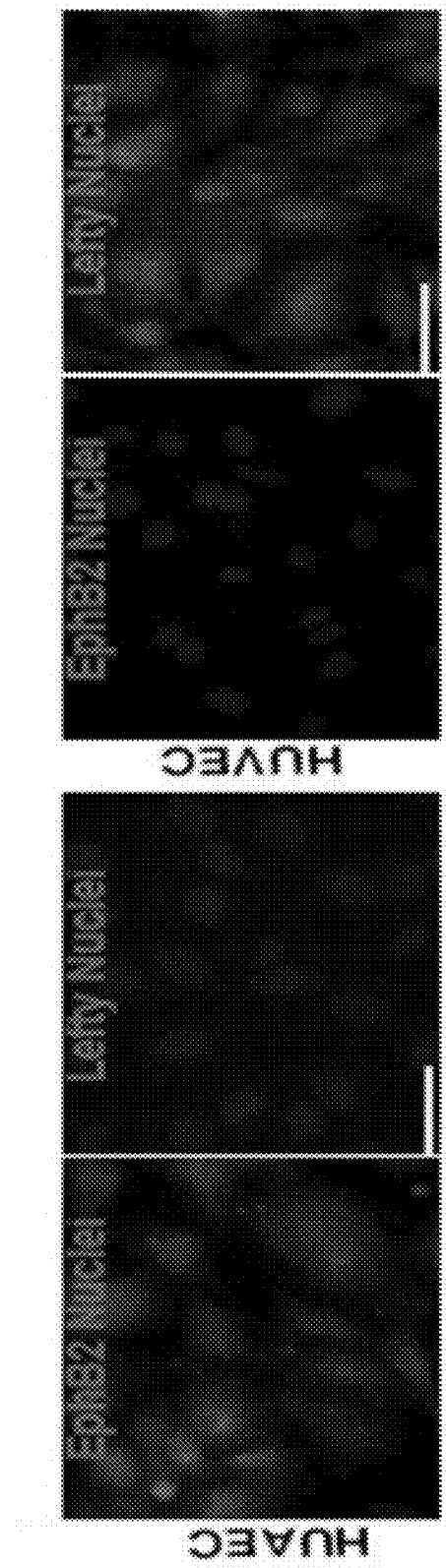
Figure 10A:
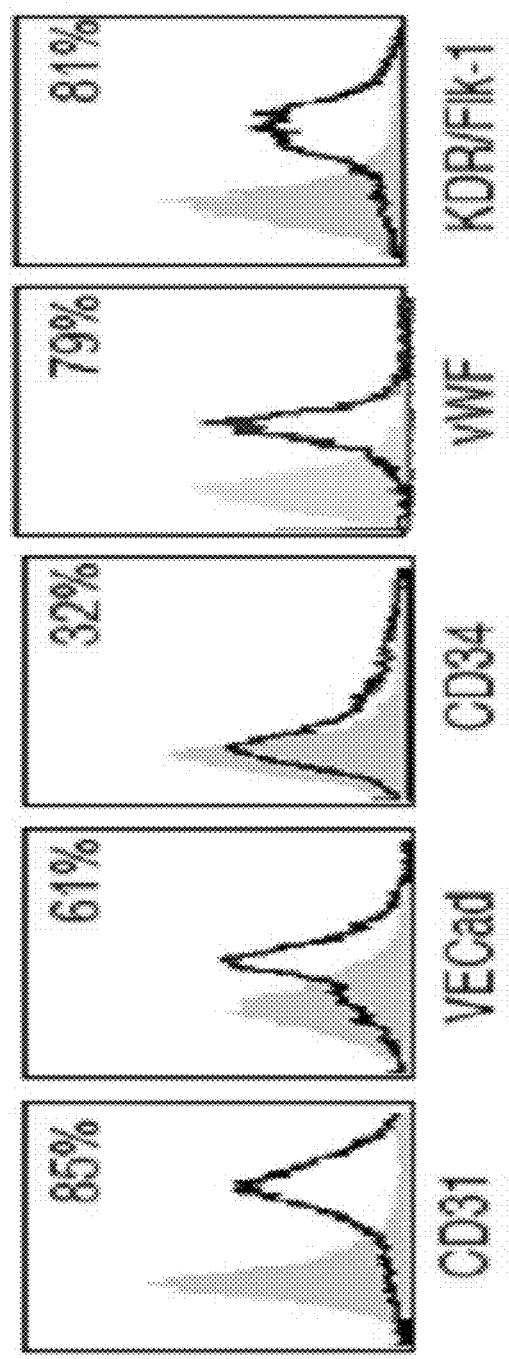
FIGS. 10A-10C: Characterization of hIPS-derived ECs (hIPSC—Human Induced Pluripotent Stem Cell). CD31+ cells isolated by MACS were plated and differentiated for 4 passages (approximately 17 days after cell seeding) using the differentiation protocol previously used for hESCs.
Figure 10B:
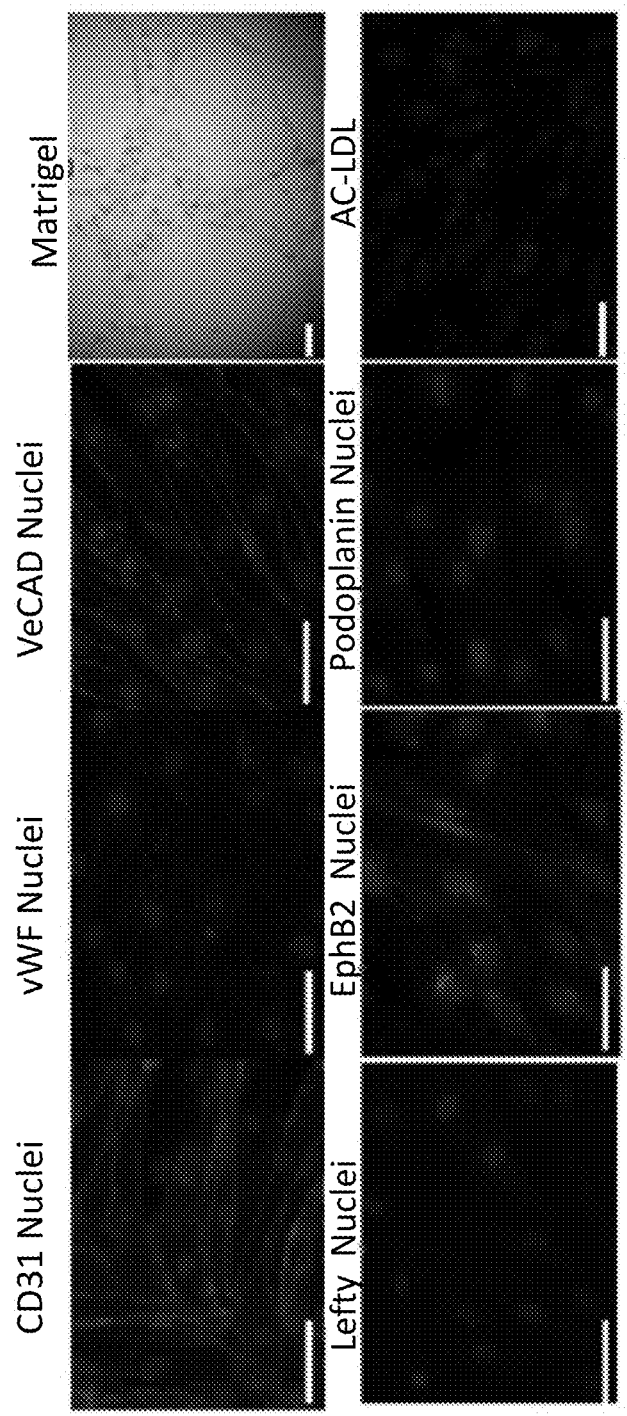
Figure 10C:
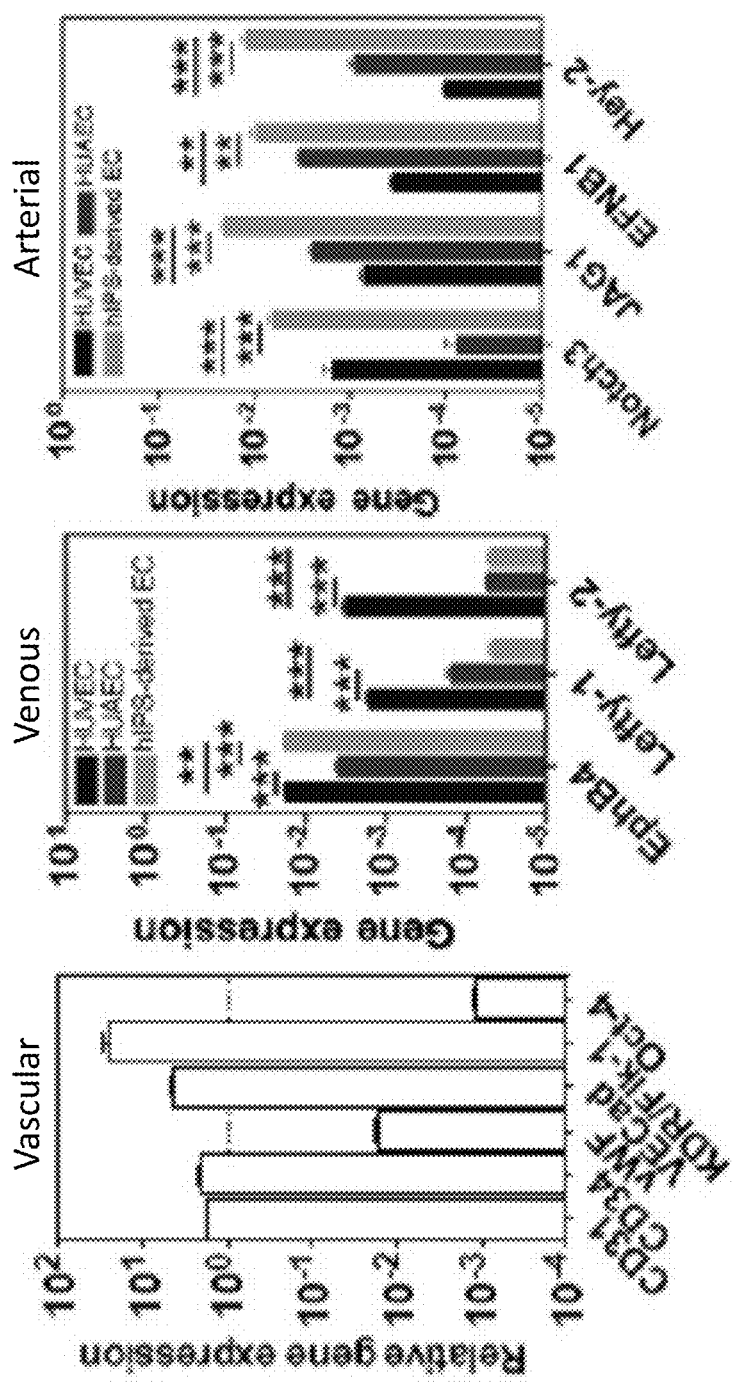

Next, the sub-phenotype of hESC-derived ECs was determined, i.e., whether the ECs have been committed to arterial, venous or lymphatic lineages. Was used podoplanin (podocyte membrane mucroprotein21), EphB2 (a transmembrane ligand13) and Lefty 1/222 as lymphatic, arterial and venous markers, respectively. As expected, human umbilical arterial ECs (HUAECs) express EphB2 but do not express Lefty 1/2 while HUVECs express Lefty 1/2 but do not express EphB2 (FIG. 9C). HESC-derived ECs stain positive for arterial marker EphB2 but not for the venous marker Lefty 1/2 or the lymphatic marker podoplanin (FIG. 1A). Gene microarrays were also performed to confirm arterial sub-phenotype. HESC-derived ECs express most of arterial markers shown by HUAECs or human aortic arterial endothelial cells (HAECs) such as JAG1, JAG2, EFNB1, EFNB2, NOTCH1, NOTCH2, NOTCH3, NOTCH4, DLL1, DLL3, DLL4, ALDHA1, HEY2, LIPG, CD44, KRT78, FSTl)[22] (FIG. 1B and Table 1). These results were further confirmed by qRT-PCR. hESC-derived ECs have high expression of arterial genes such as JAG1, EFNB1 and Hey-2 and low expression of venous genes such as EphB4, Lefty-1 and Lefty-2 (FIG. 1C). Together, the results indicate that hESC-derived ECs have been coaxed into arterial ECs. The strategy was initially tested with H9 hESC line; however, the protocol robustness was subsequently validated on a hiPSC line (K2) generated from cord blood[23] (FIG. 10).

Figure 11A:
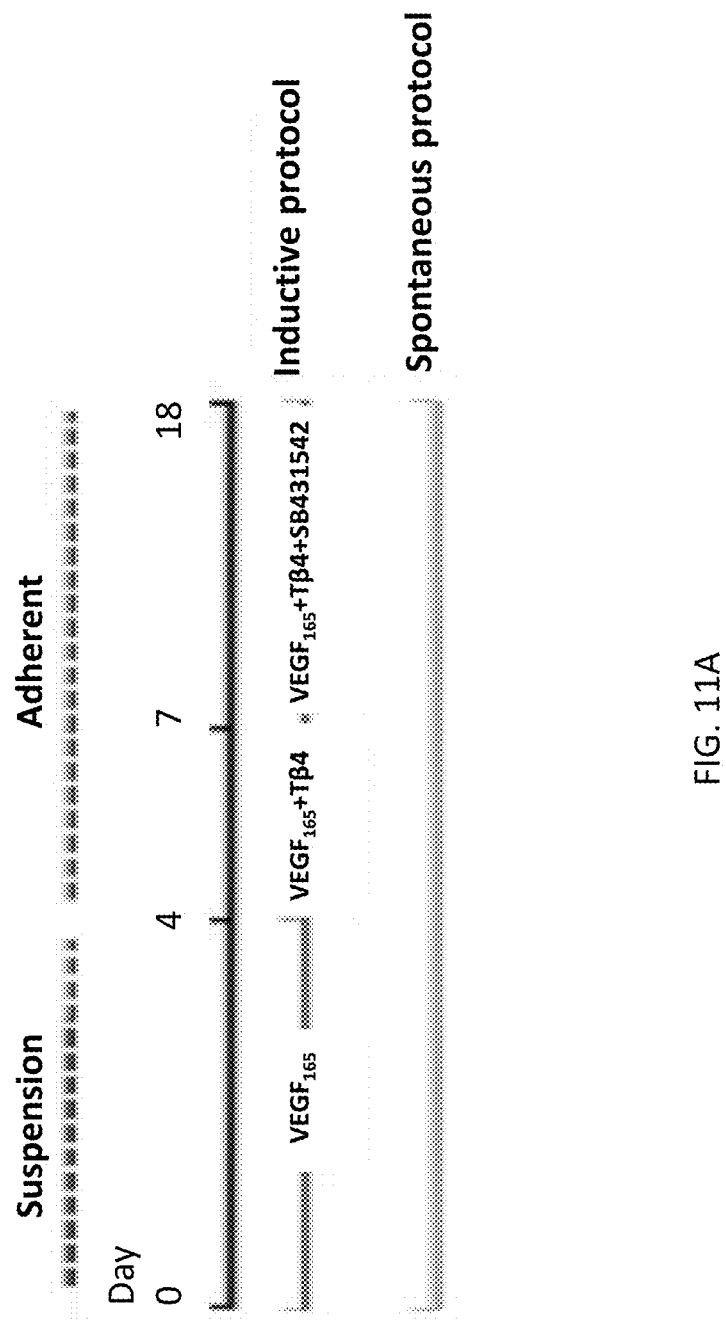
FIGS. 11A-11D: Expression of arterial and venous genes during the inductive and spontaneous differentiation protocol.
Figure 11B:
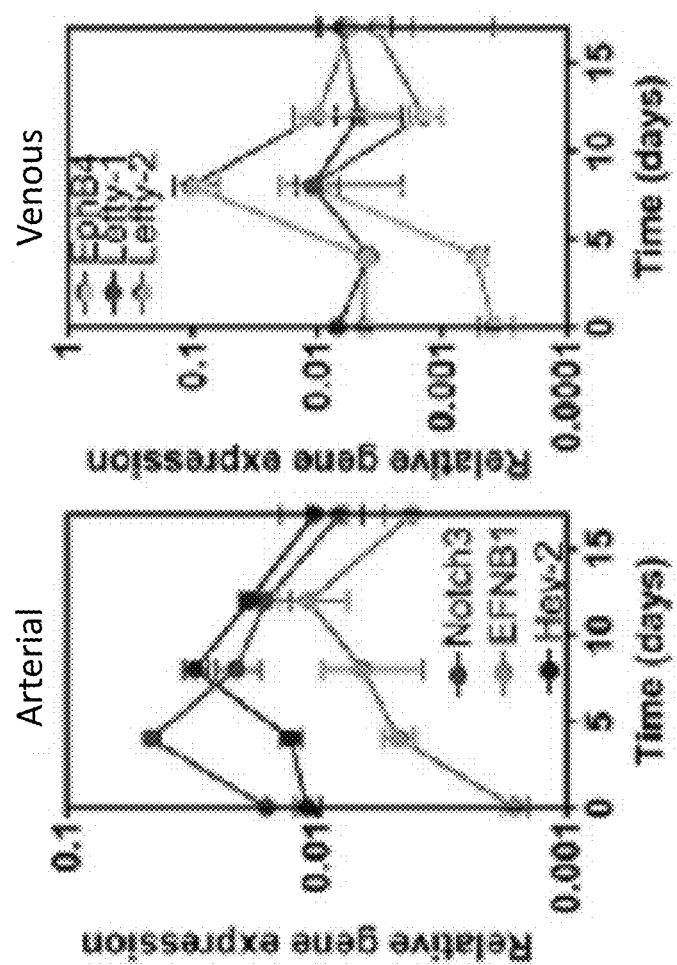
Figure 11C:
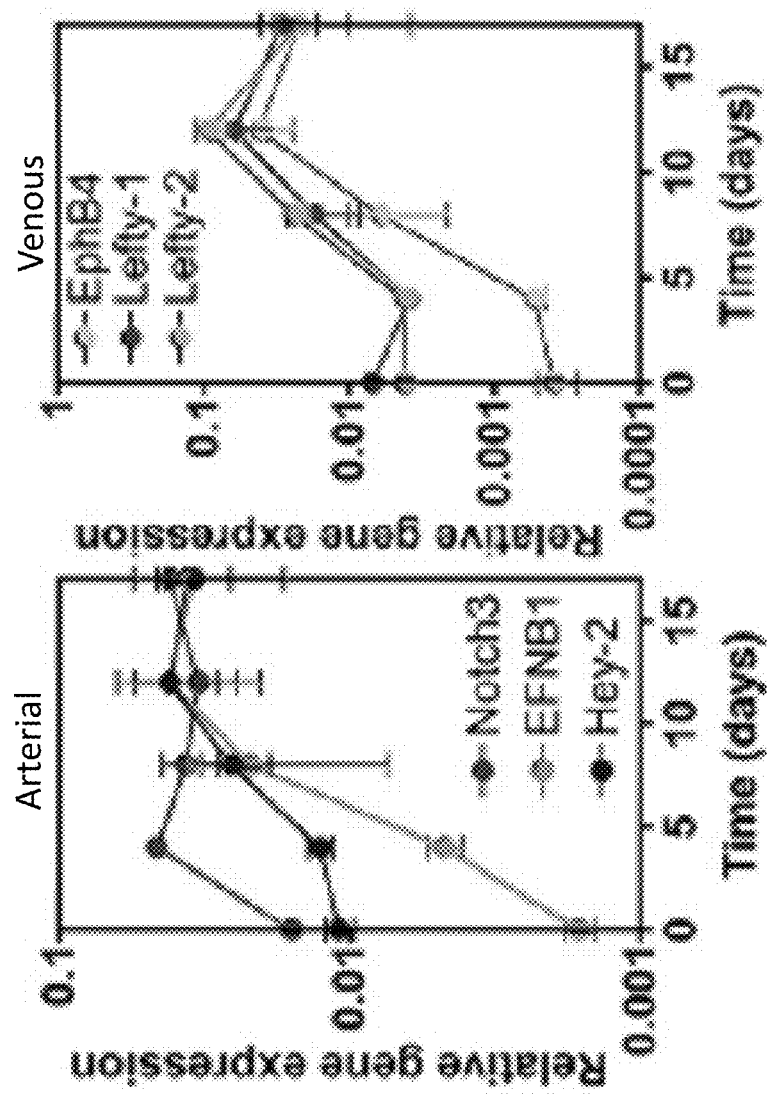
Figure 11D:
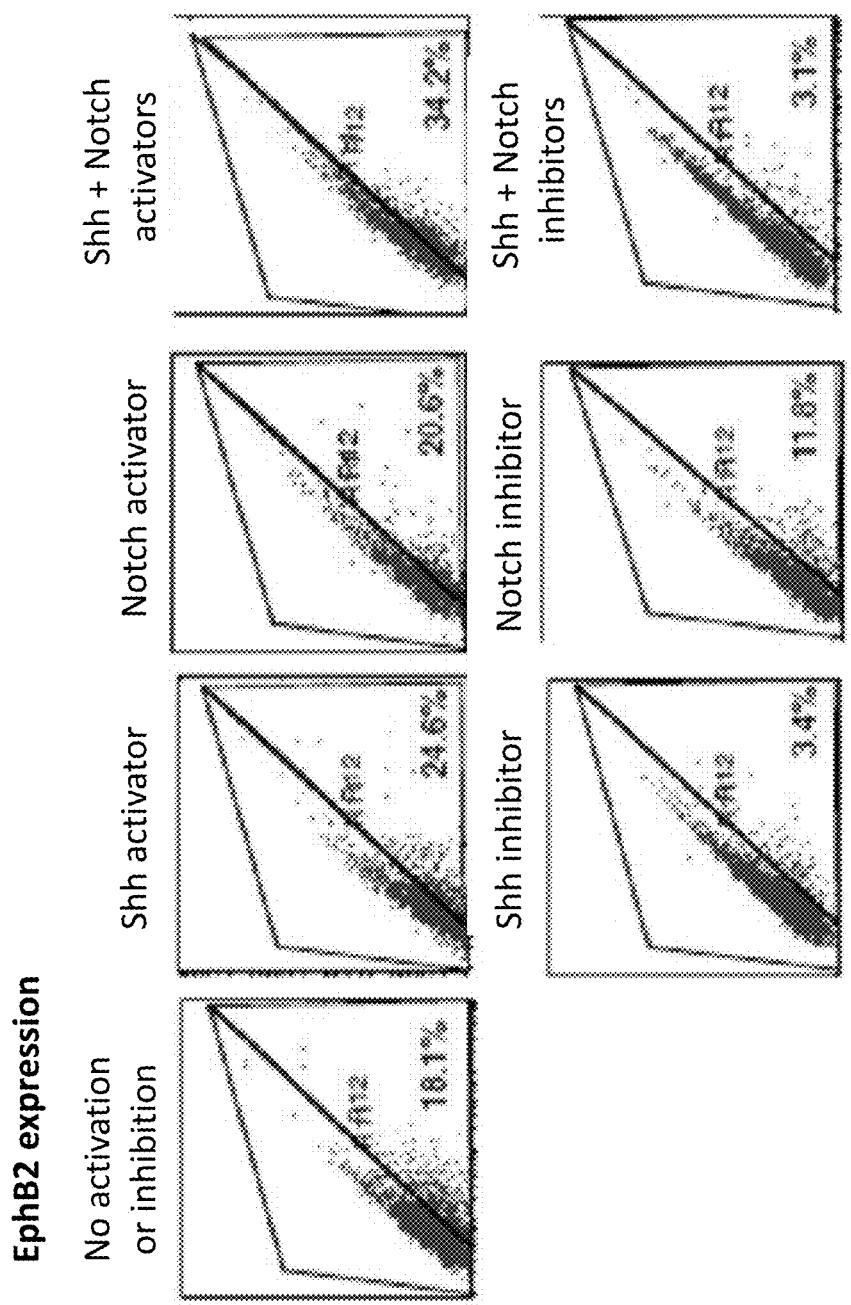

Next, we asked whether the ECs have been committed to arterial phenotype at the isolation of CD31+ cells or after their differentiation. Both arterial and venous genes are expressed during the inductive and spontaneous differentiation protocols (FIG. 5A), and the inductive protocol does not seem to increase the expression of arterial genes as compared to the spontaneous protocol (FIGS. 11B and 11C).

Figure 1D:
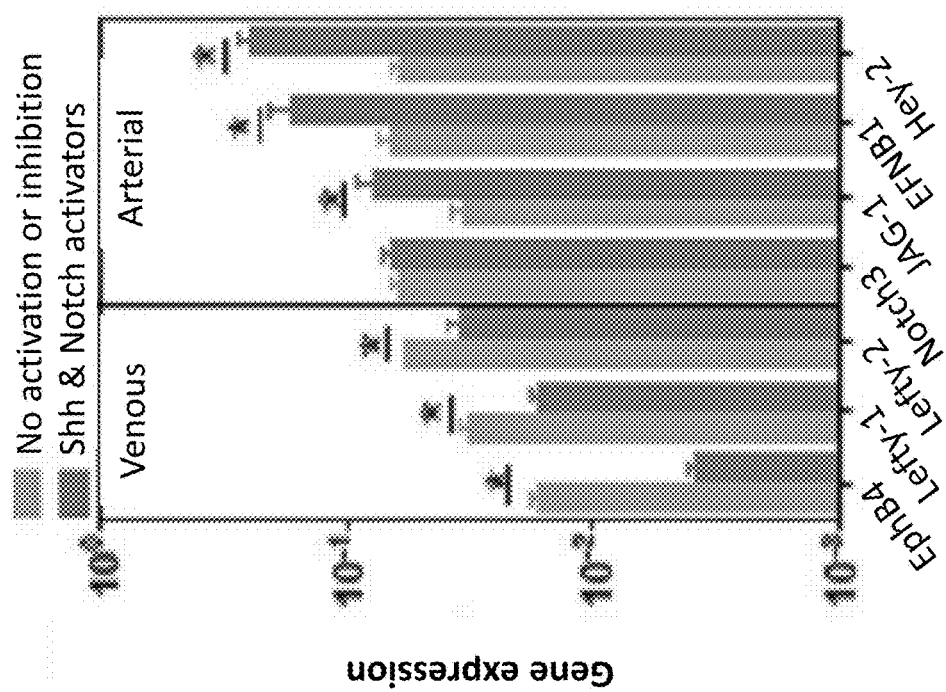
Figure 1E:
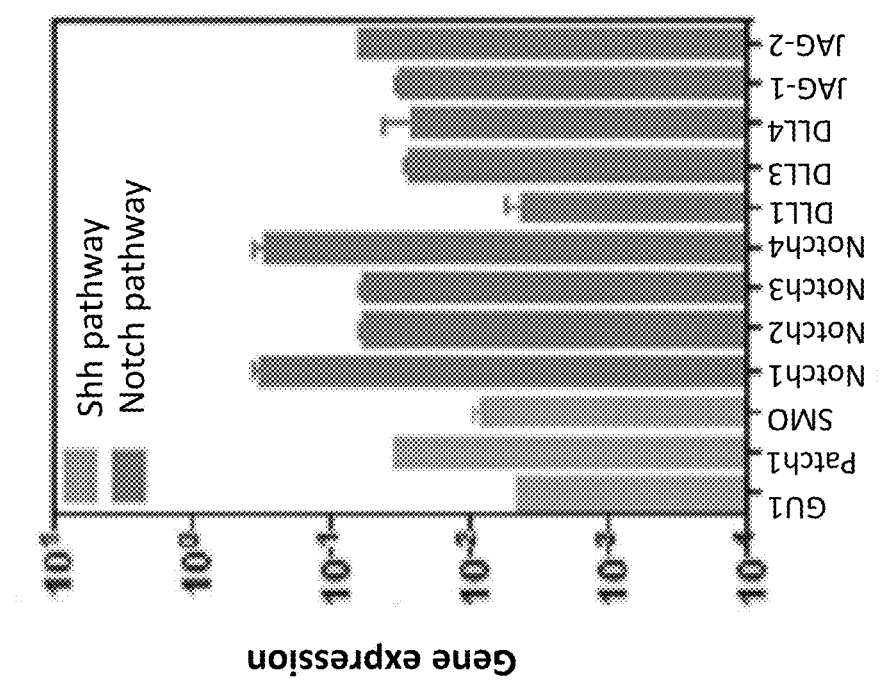
Figure 1F:
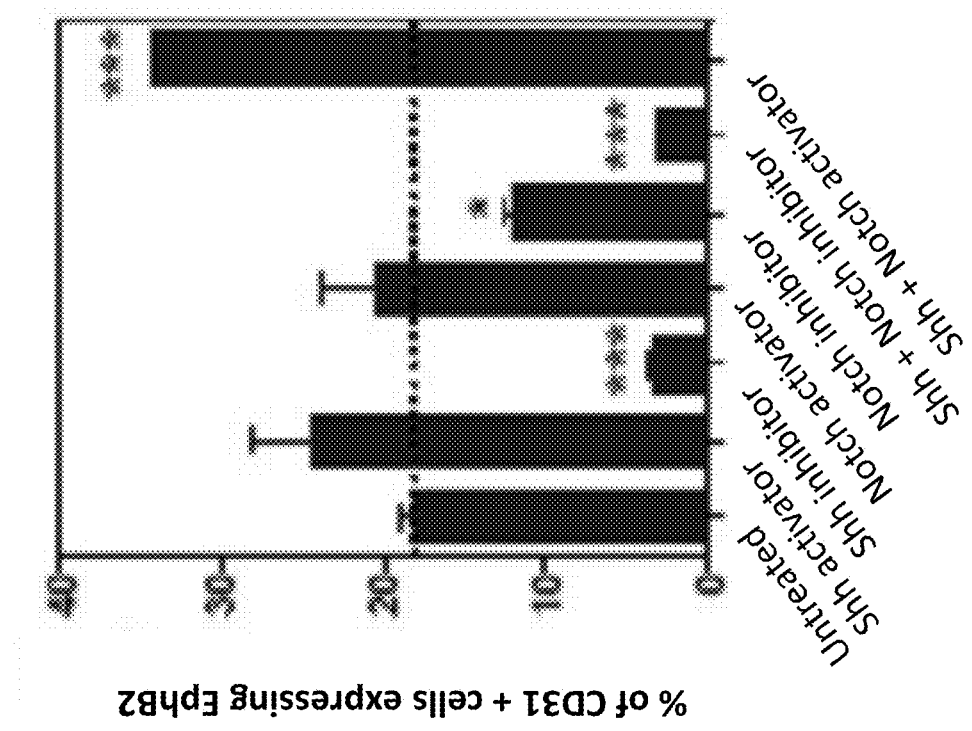

Arterial and venous gene expression was analyzed in CD31+ cells at the time of their isolation. Both venous and arterial markers were expressed at similar magnitude (FIG. 10, orange columns), which suggests that sub-phenotype is not defined at the isolation of CD31+ cells but only after their differentiation. Because arterial/vein specification during mouse embryogenesis is in large part mediated by Notch and Sonic Hedgehog (Shh), the expression of Notch (Notch1, Notch2, Notch3, Notch4) and Shh (patched 1) receptors as well as Notch (DLL1, DLL3, DLL4, JAG-1, JAG-2) and Shh transcription factors (GLI1 and SMO) in CD31+ cells was assessed (FIG. 1E). The results show that CD31+ cells after isolation express both Notch and Shh ligands and receptors. Was also studied the involvement of Notch and Shh signaling pathways in the gene expression of arterial and venous markers in cells after CD31+ cell isolation. The independent activation of each signaling pathway has little impact in the expression of arterial marker EphB2 (FIG. 1F).

However, the simultaneous activation of Shh and Notch signaling by purmorphamine and DLL4, respectively, significantly increased the expression of arterial EC markers such as EphB2 (protein level), HEY-2, JAG-1 and EFNB1 (gene level), and simultaneously decreased the expression of venous EC markers such as Lefty-1 and Lefty-2 (FIG. 1D), as compared to cells cultured without these activators. By other hand, inhibiting both Shh and Notch signaling by cyclopamine and an inhibitor of p-secretase, respectively, significantly decreased the expression of arterial marker EphB2 (FIG. 1F). Taken together, these results indicate that arterial specification mainly occurs after the isolation of CD31+ cells, and Shh and Notch signaling pathways mediate at least in part the specification of hPSCs into the arterial phenotype.

Figure 1G:
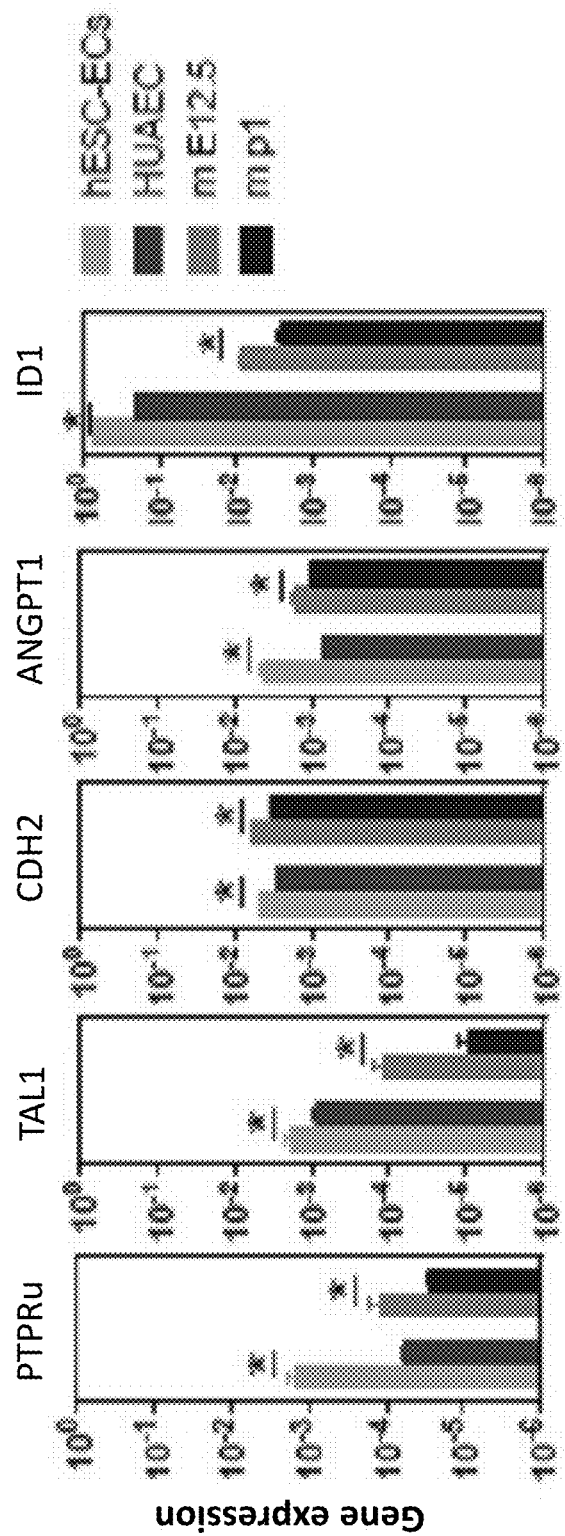
Figure 1H:
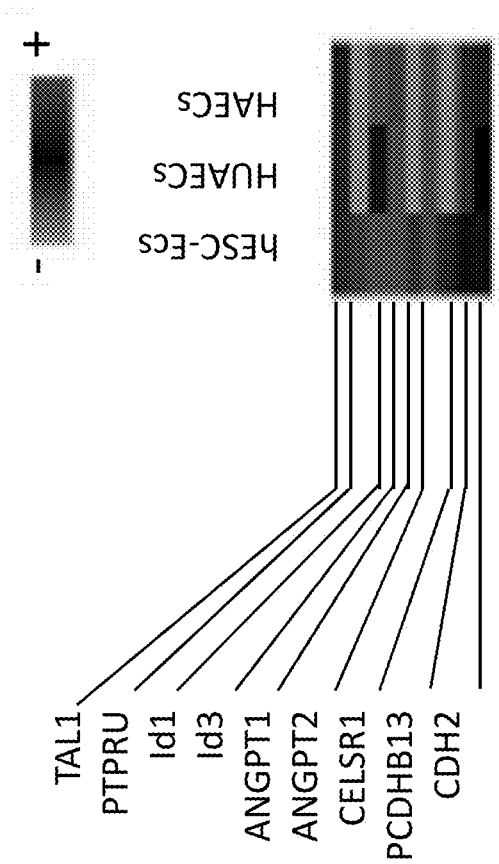
Figure 1I:
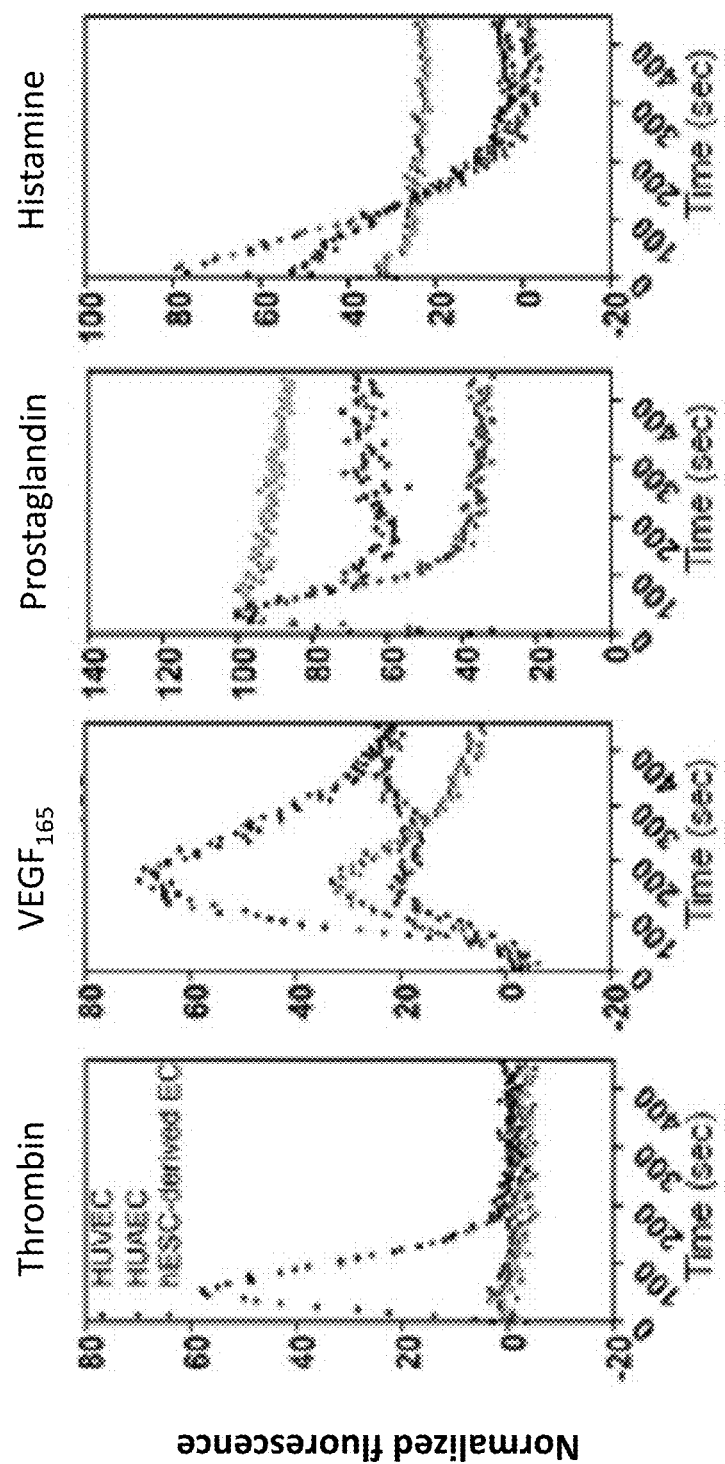

To determine whether the cells had an embryonic or adult arterial phenotype gene microarrays for hESC-derived ECs, HUAECs (fetal phenotype) and HAECs (adult phenotype) were performed. Comparing the expression of hESC-derived-EC and HUAEC we found a 67 up-regulated genes and 141 down-regulated genes (P<0.001 and cutoff of three times up- or down-regulated). Embryonic gene candidates were identified from gene expression on ECs isolated from mouse at day E12.5 and P1 (after birth). The receptor protein tyrosine phosphatase µ (PTPRu), the T-cell acute lymphocyte leukemia 1 (TAL1), N-cadherin (CDH2), angiopoietin 1 (ANGPT1) and DNA-binding protein inhibitor ID-1 (ID1), are up-regulated in mouse ECs E12.5 as compared to mouse ECs P1 (FIG. 1G). Similarly, those genes are up-regulated in hESC-derived ECs as compared to HUAECs. The receptor protein tyrosine phosphatase µ (PTPRu) has been reported as present in the aorta of mouse embryos, but not in the adult mice[24]. The T-cell acute lymphocyte leukemia 1 (Tal1), also known as ScI, is a transcription factor (basic helix-loop-helix) several times associated with newly formed vessels and absent in quiescent endothelium[25, 26]. In addition, major cadherins expressed in early embryos of Xenopus laevis are E-cadherin, N-cadherin and a maternal cadherin known as either C-cadherin or EP-cadherin[27, 28]. Microarray analyses showed also that the previous embryonic genes as well as others are higher expressed in hESC-derived ECs than in hUAECs or hAECs (FIG. 1H and Table 2). Overall, results indicate that the hESC-derived ECs have an embryonic arterial phenotype.

To determine whether the ECs were functional was evaluated their ability to uptake Dil-labeled acetylated low-density lipoprotein (Dil-Ac-LDL), to form cord-like structures and to respond to vasoactive agonists. FIG. 1A confirm that hESC-derived ECs are able to take up Dil-Ac-LDL and to form cord-like structures when cultured in the basement membrane Matrigel. Furthermore, the hESC-derived ECs respond to the vasoactive agonists as normal ECs by increasing the intracellular levels of $Ca^{2+}$ (FIG. 11). Cells were loaded with FURA-2, a $Ca^{2+}$ sensitive dye, and their response to known concentrations of vasoactive agonists histamine, $VEGF_{165}$, prostaglandin H2-analogue U46619 and thrombin was monitored by fluorescence. The response profile was compared to the one observed for HUVECs and HUAECs. HESC-derived ECs share a similar response profile to thrombin as HUAECs but different response profiles to $VEGF_{165}$, prostaglandin H2-analogue and histamine. No similarity was found in the response profiles of hESC-derived ECs and HUVECs. Together, results show that hESC-derived ECs are functional however showing different response profiles to vasoactive agonists as compared to HUAECs and HUVECs. The differences found between hESC-derived ECs and somatic arterial ECs (i.e. HUAECs) are likely ascribed to their embryonic and adult phenotypes.

Figure 2A:
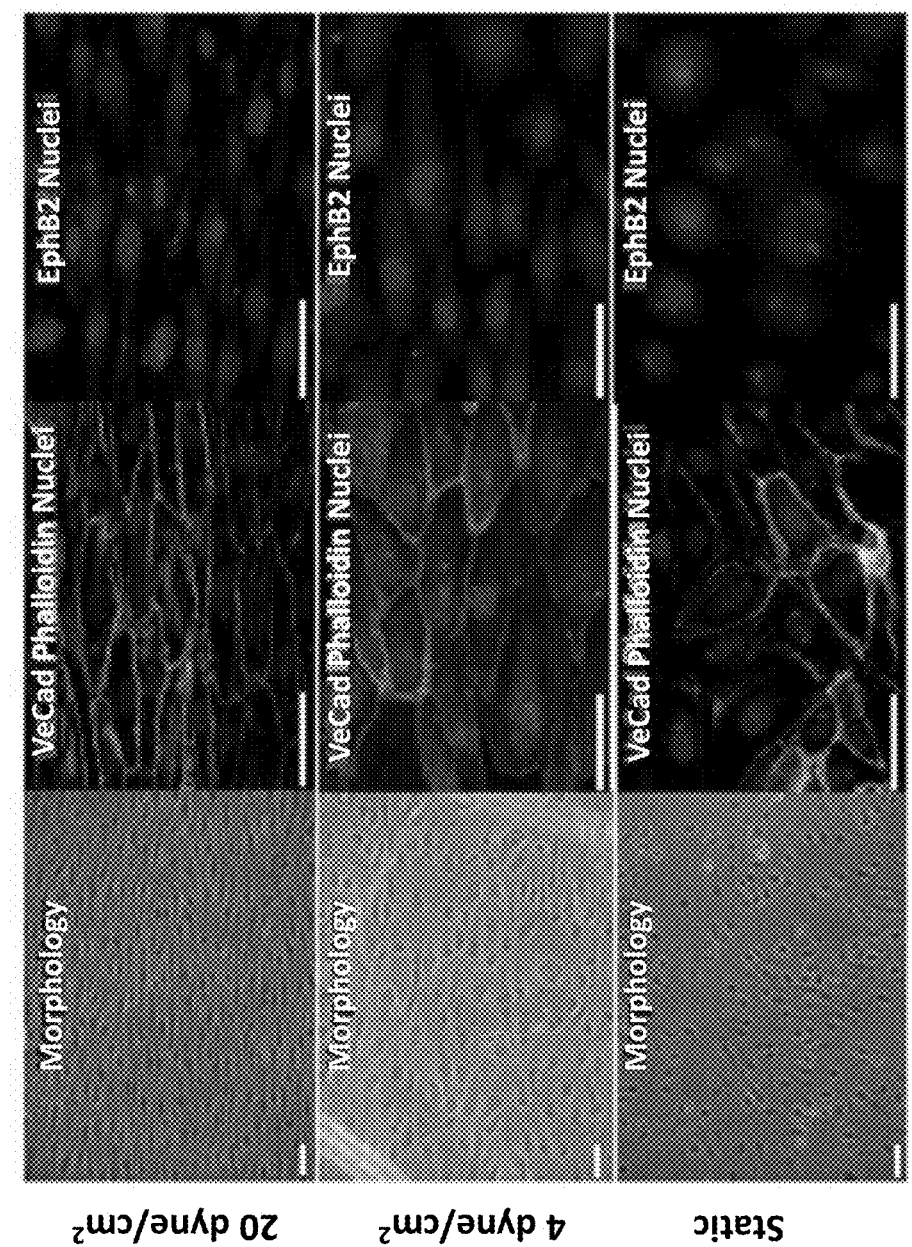
FIGS. 2A-2D: Effect of fluidic shear stress on hPSC-derived ECs.
Figure 2B:
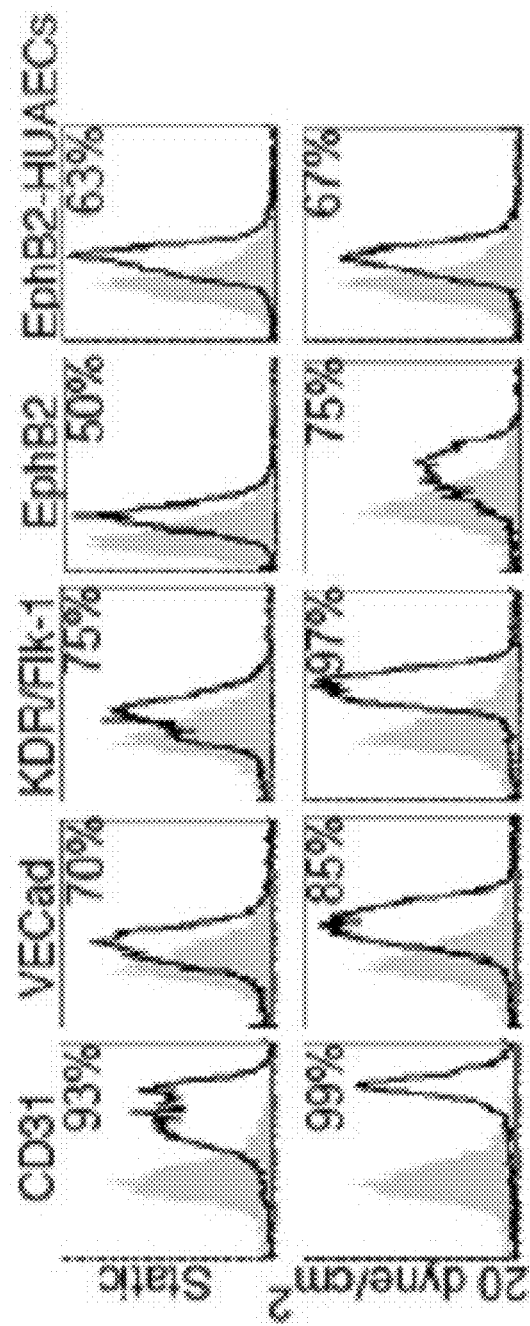
Figure 2C:
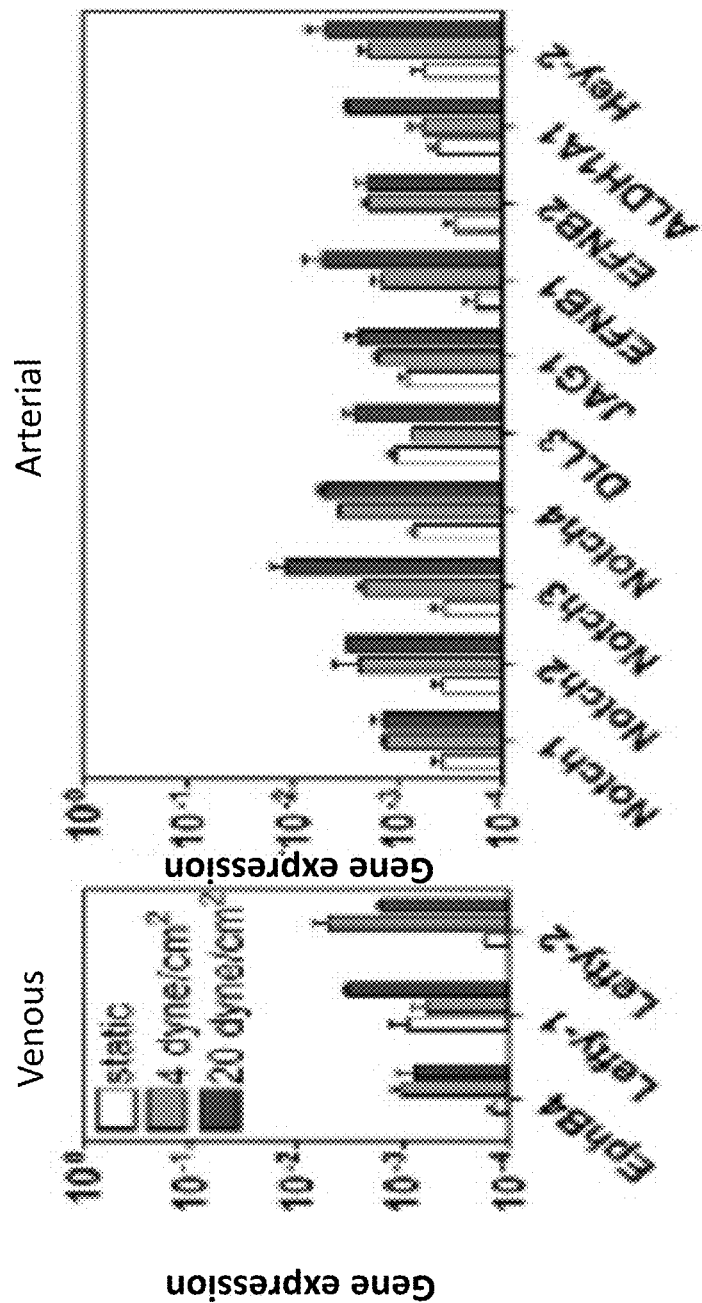
Figure 12A:
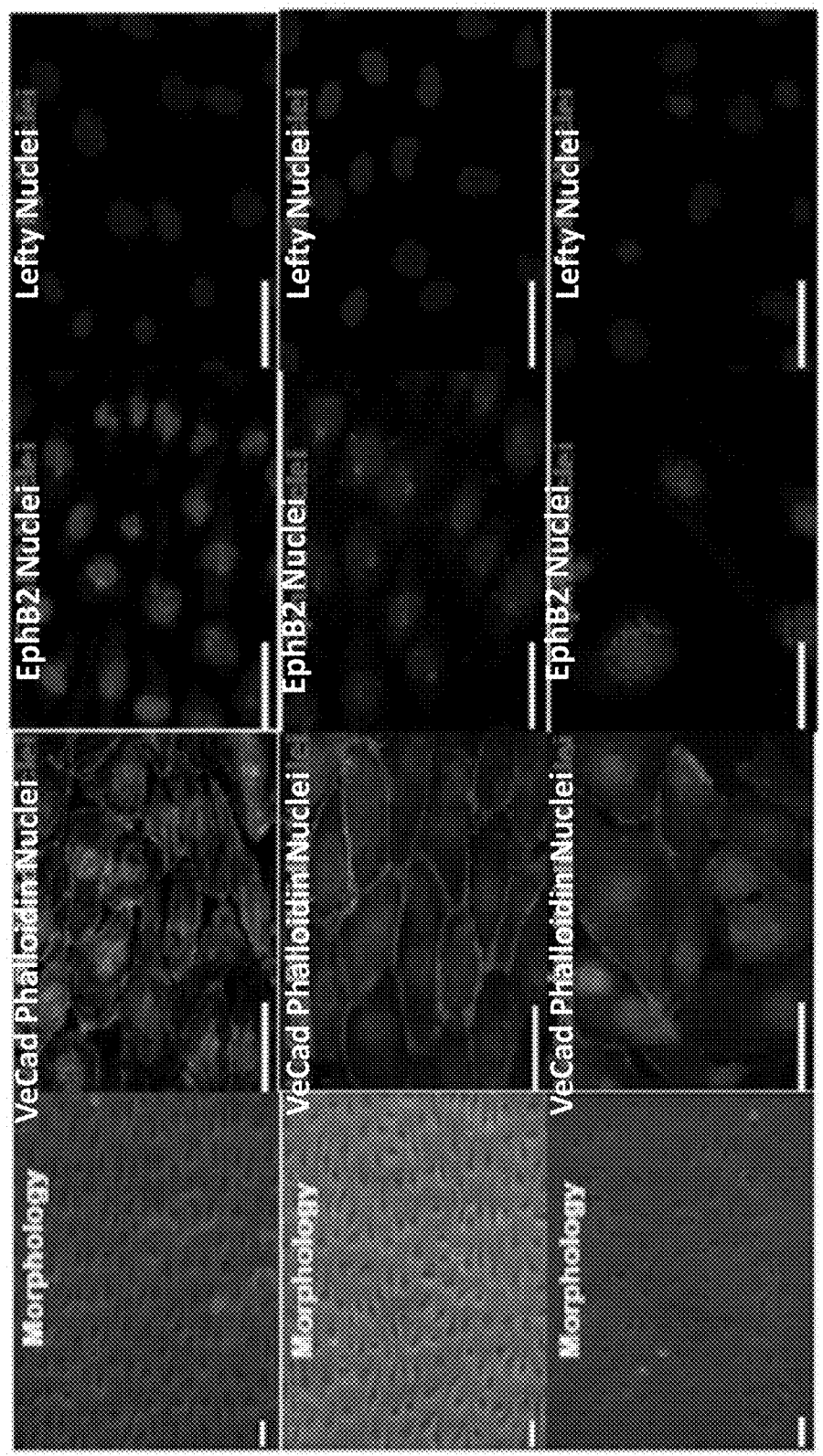
FIG. 12A-12B: Expression of arterial and venous EC markers in HUAECs cultured on static and flow conditions (7 days), as evaluated by immunocytochemistry (FIG. 12A) and qRT-PCR analysis (FIG. 12B).
Figure 12B:
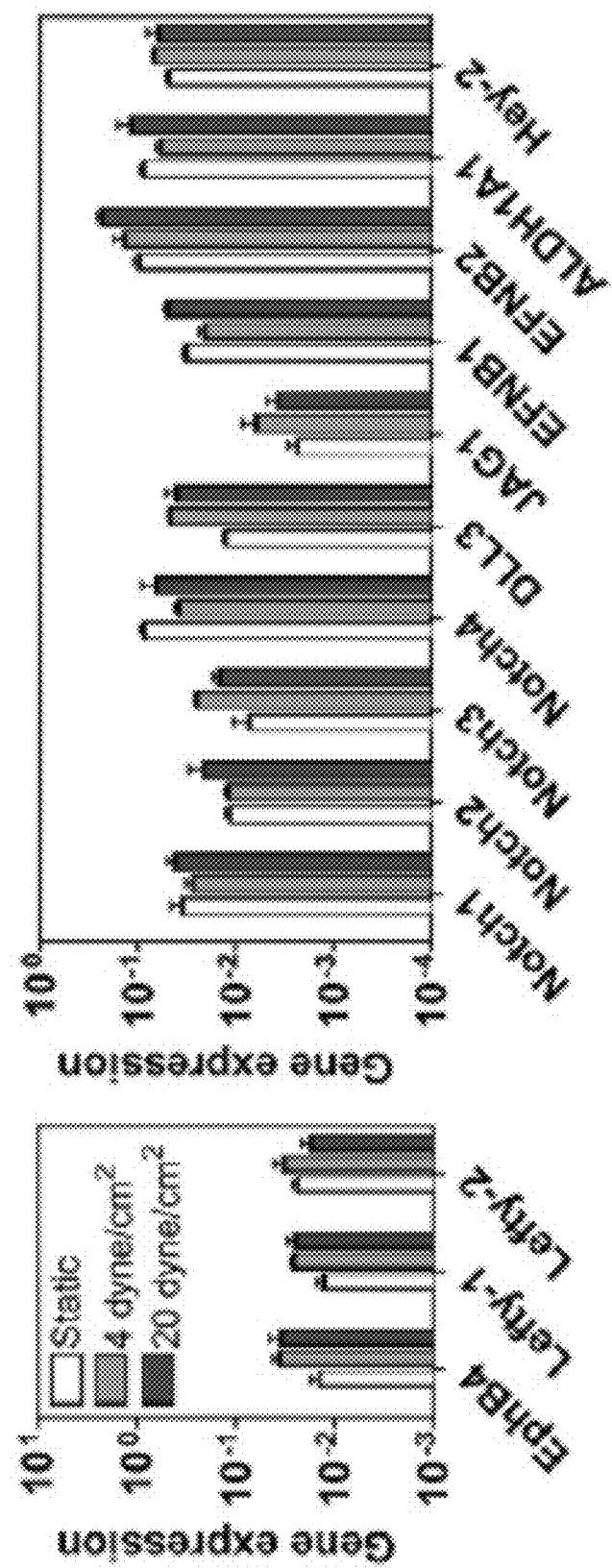

Influence of Shear Stress in EC Morphology, Modulation of Arterial Sub-Phenotype and Glycocalix Expression Having demonstrated the differentiation of hESCs into arterial ECs was studied how the differentiated cells responded to arterial (20 dyne/cm$^2$) and venous (4 dyne/cm$^2$) shear stress[29]. It has been shown that a mechanosensory complex formed by CD31, VE-Cad and VEGFR-2 mediates the responsiveness of ECs to shear stress[16,30]. The activation of this complex leads to integrin activation and alignment which triggers the activation of VEGFR-2 tyrosine kinases, extracellular signal-regulated kinases (ERKs), c-Jun amino-terminal kinases (JNKs), p38 mitogen-activated protein kinase and AKT serine/threonine kinases and transcription factors such as NF-kB. To study the influence of shear stress, hESC-derived ECs (or HUAECs as control) were cultured for 7 days in flow conditions. HESC-derived ECs cultured in arterial flow (20 dyne/cm$^2$) conditions align morphologically in the direction of the flow and show alignment of the proteins VE-Cad and actin (stained with phalloidin) (FIG. 2A). Similar results have been obtained for HUAECs (FIG. 12). The alignment of the cells is dependent on the magnitude of the shear stress since cells cultured in low (4 dyne/cm$^2$) or no flow (static conditions) show low or no alignment, respectively. Importantly, cells cultured in flow or static conditions express EphB2 but not lefty A/B (FIG. 2A and FIG. 12). The expression of EphB2 is higher in flow than in static conditions, since 75% and 50% of the cells express EphB2 in flow and in static conditions, respectively (FIG. 2B). In addition, the expression of CD31, VE-Cad and VEGFR-2 (KDR/FIK-1) is also up-regulated in flow conditions (FIG. 2B). The up-regulation of these proteins is in agreement with previous data showing that their involvement on a mechanosensory complex that mediates the EC response to fluid shear stress[30]. The maturation of hESC-derived ECs into arterial cells was also observed at gene level (FIG. 2C). Cells cultured under arterial or venous flow conditions express higher levels of arterial genes such as Notch receptors (1,2,3 and 4), Notch ligands (DLL3 and Jagged-1), Notch transcription factor Hey-2, aldehyde dehydrogenase 1 (ALDH1A1), and ephrin-B1 (EFNB1) and ephrin-B2 (EFNB2), which are ligands of ephrin receptors. Gene expression increased with an increase with flow. An upregulation of venous genes such as EphB4 and Lefty was also observed when the cells were cultured under flow conditions; however, no lefty protein was observed under these conditions (FIG. 2C and FIG. 12A). Interestingly, HUAECs cultured under static or flow conditions have the same gene expression profile (FIG. 12B), and therefore it suggests that hESC-derived ECs are more prone to respond to shear stress than mature somatic cells. Overall, the results indicate that hESC-derived ECs respond to arterial flow by the alignment of VECAD and actin fibers, up-regulation of the mechanosensory complex VECad, CD31 and VEGFR2, and by the up-regulation of arterial marker EphB2.

Figure 2D:
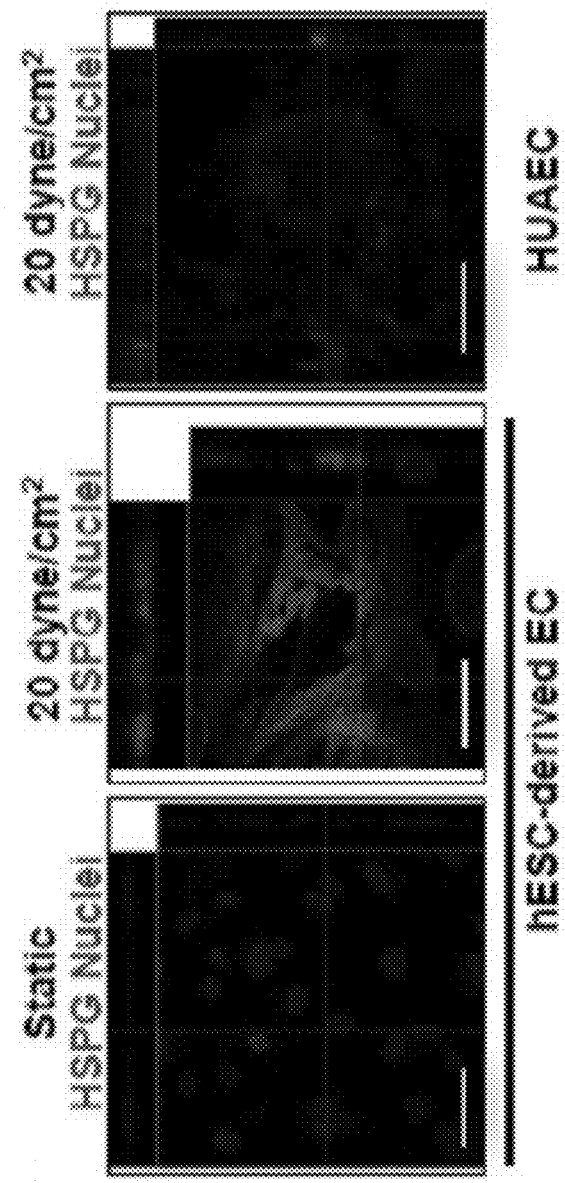

Heparan sulfate proteoglycan (HSPG), a component of glycocalyx layer of ECs, has been reported to be a fluid stress sensor on ECs[31, 32]. A class of HSPG, syndecans, is known to associate with cytoskeletal elements including actin, either directly or through associated actin-binding proteins[31]. Importantly, HSPG is absent on ECs grown and maintained under standard cell culture conditions in vitro, i.e. without flow[33]. Therefore was investigated whether hESC-derived ECs express HSPG under flow culture conditions (20 dyne/cm$^2$). Confocal microscopy analysis show that the surface of hESC-derived ECs or control HUAECs cultured under flow conditions is abundantly decorated with HSPG while no expression of HSPG is observed in static conditions (FIG. 2D). The HSPG is detected in the apical region of ECs (XZ view) exposed to flow. These results show that hESC-derived ECs can respond to flow by producing HSPG, as it is observed in vivo conditions.

Vascular Toxicity Assessed in hESC-Derived ECs Cultured Under Flow Conditions

Figure 3A:
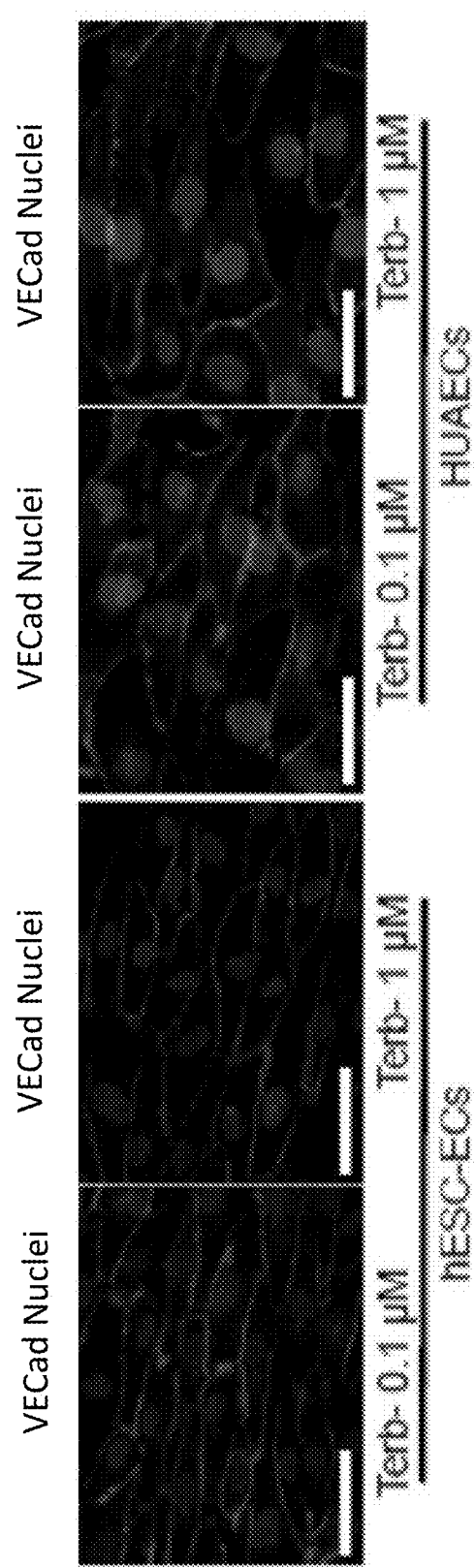
FIGS. 3A-3C: hPSC-derived ECs as a model to evaluate vascular toxicity.
Figure 3B:
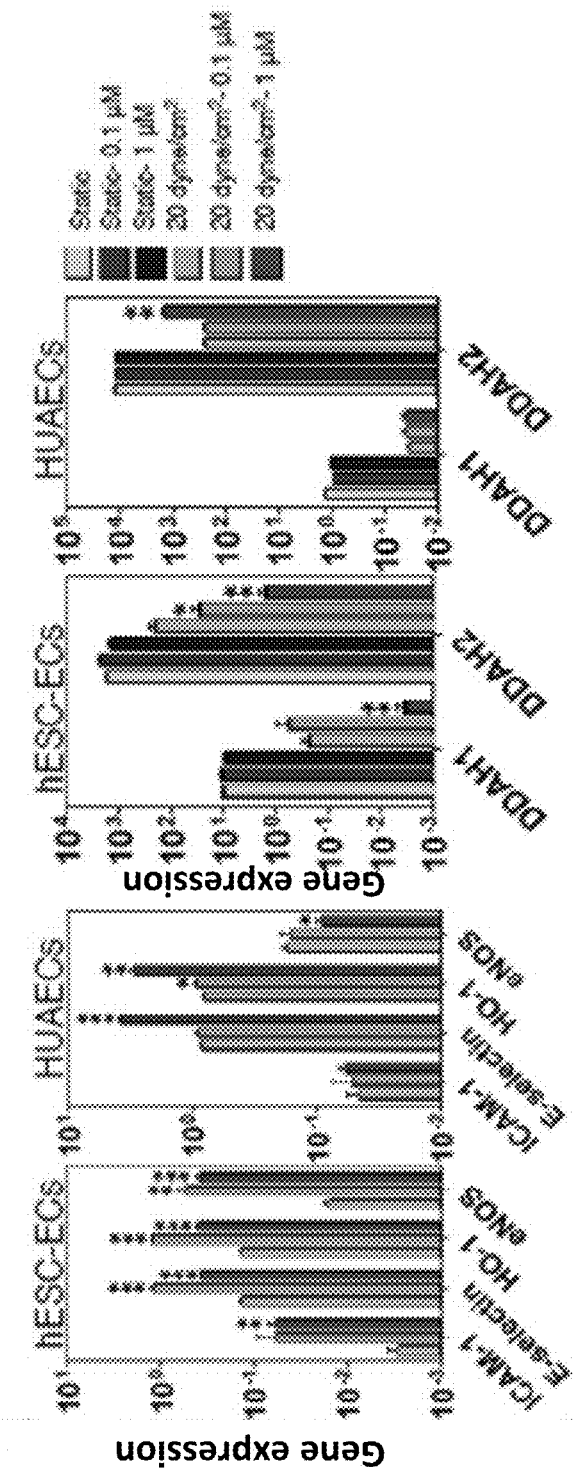

Terbinafine is an antifungal agent (inhibitor of ergosterol synthesis) that inhibits angiogenesis by suppressing endothelial cell proliferation, inhibits DNA synthesis and activates EC apoptosis[34, 35]. Terbinafine is cytotoxic for HUVECs for concentrations above 120 $\mu M$[35]. To determine whether the hESC-derived ECs cultured under flow conditions could be used to assess vascular toxicity, cells were cultured for 7 days at 20 dyne/cm2 after which the culture medium was supplemented or not with terbinafine (0.1 and 1 $\mu M$) and cells cultured under the same flow conditions for one more day. No significant changes in terms of EC morphology and cadherin expression were observed in ECs cultured in the presence or absence of the drug at day 8 (FIG. 3A). Next, was assessed by qRT-PCR the expression of genes involved in inflammation (ICAM-1; E-selectin), oxidative stress sensing (HO-1) and vasculature modulation (eNOS) in hESC-derived cells and control HUAEC after exposition to terbinafine (FIG. 3B). As expected, the expression of these genes increases under fluidic shear stress[36]. Interestingly, the expression of the genes is higher when hESC-derived ECs were cultured in the presence of terbinafine at 0.1 $\mu M$. Upregulation of some genes (HO-1 and E-selectin) was only observed for concentrations of 1 $\mu M$ in HUAECs. These results were complemented by evaluating the expression of two genes related to the expression of dimethylarginine-dimethyl-amino-hydrolases (DDAH), a family of enzymes that metabolizes asymmetric dimethylarginine (ADMA)[37]. ADMA is a naturally occurring amino acid that circulates in plasma and is generated by degradation of methylated proteins. Increase levels of ADMA inhibits nitric oxide (NO) production by competitive inhibition of the physiological substrate L-arginine[38]. Drugs that inhibit NO pathway, upregulate caveolin-1 expression and/or enhance ADMA levels could potentially be associated with drug-induced endothelial dysfunction. Therefore, increased circulating levels of ADMA may serve as predictive marker of EC dysfunction[38]. To date, two isoforms of DDAH (DDAH1 and DDAH2) have been found in mammals. hESC-derived ECs cultured under flow conditions in medium supplemented with terbinafine show a significant decrease in the expression of DDAH1 and DDAH2 ($P<0.05$ or $P<0.01$, n=4). Such effect was not observed for HUAECs cultured under the same conditions. Interestingly, the decrease of DDAH1 and DDAH2 in hESC-derived ECs was only observed when cells were culture under flow conditions. Overall results indicate that cells cultured under physiologic shear stress have higher sensitivity to cytotoxic compounds such as terbinafine than cells cultured in static conditions. In addition, hESC-derived ECs are more sensitive to the effect of terbinafine than HUAECs.

Figure 3C:
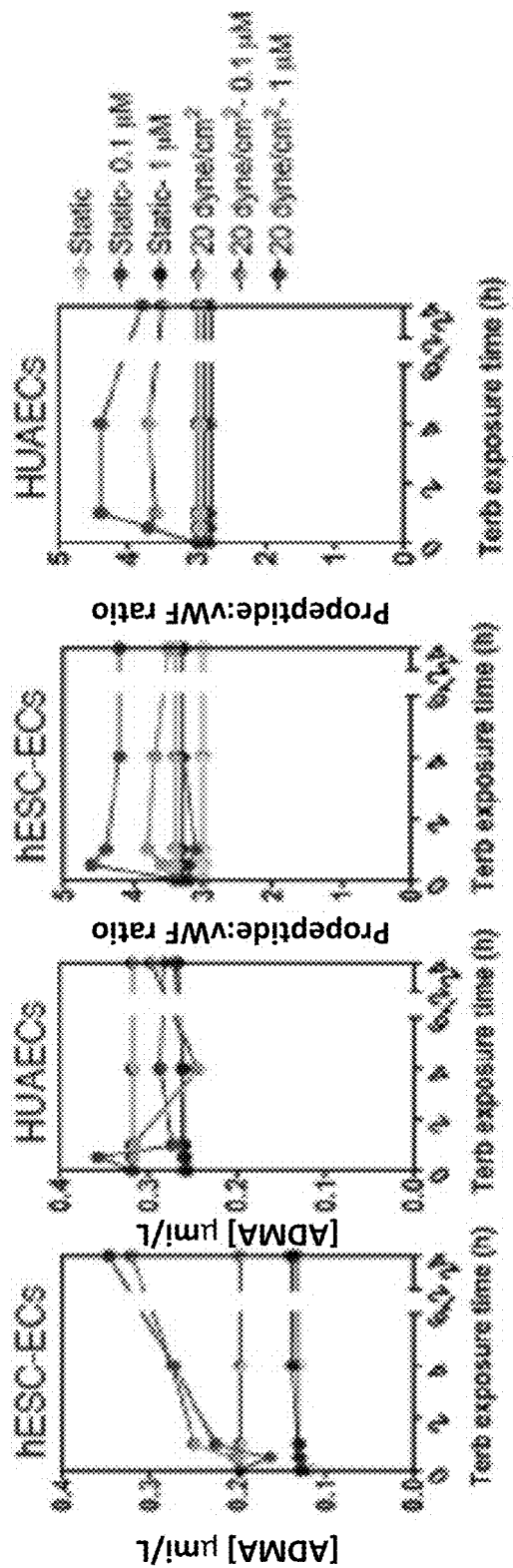

Next, the vascular damage/injury induced by terbinafine was assessed in hESC-derived ECs and control HUAECs, in the same conditions as before, by measuring the levels of ADMA and the ratio von Willebrand factor pro-peptide (vWFpp): von Willebrand factor (vWF) secreted by these cells (FIG. 3C). The last 2 proteins with different biological activity are released in equimolar concentrations in plasma and an increased level of both proteins predicts EC activation/injury. Analysis of vWFpp:vWF ratio may discriminate and/or differentiate acute from chronic and progressive vascular injury39, 40. hESC-derived ECs or HUAECs cultured in static conditions in the presence of the drug have no significant higher secretion of ADMA or vWFpp:vWF than in control conditions (i.e., without the drug). Remarkably, hESC-derived ECs cultured under flow conditions in the presence of terbinafine secrete higher levels of ADMA and vWFpp:vWF than without the drug. Again, the sensitivity of HUAECs to terbinafine was lower than hESC-derived ECs. The concentration of ADMA secreted by hESC-derived cells at 24 h is 3.5 times higher than in basal conditions. Importantly, this shift in concentration is observed in human patients with cardiovascular diseases. Healthy persons have an average of 0.45±0.19 μmol of ADMA per liter of blood and this value increases 2.2 or 2.7 folds when the patient has idiopathic pulmonary arterial hypertension[37]. Furthermore, the secreted concentrations of ADMA correlate with the concentration of terbinafine in the culture medium. The quantification of vWFpp:vWF ratio confirm some of the results obtained by ADMA. Again, no effect of terbinafine was observed in hESC-derived ECs or HUAECs cultured in static conditions. In contrast, both cells cultured in flow conditions and exposed to terbinafine secrete higher levels of vWFpp:vWF, confirming vascular dysfunction.

Identification of Embryonic Arterial Cell Inhibitors by High-Throughput Screening Followed by the Test of the Hits in Flow Cell Culture Conditions.

Figure 4A:
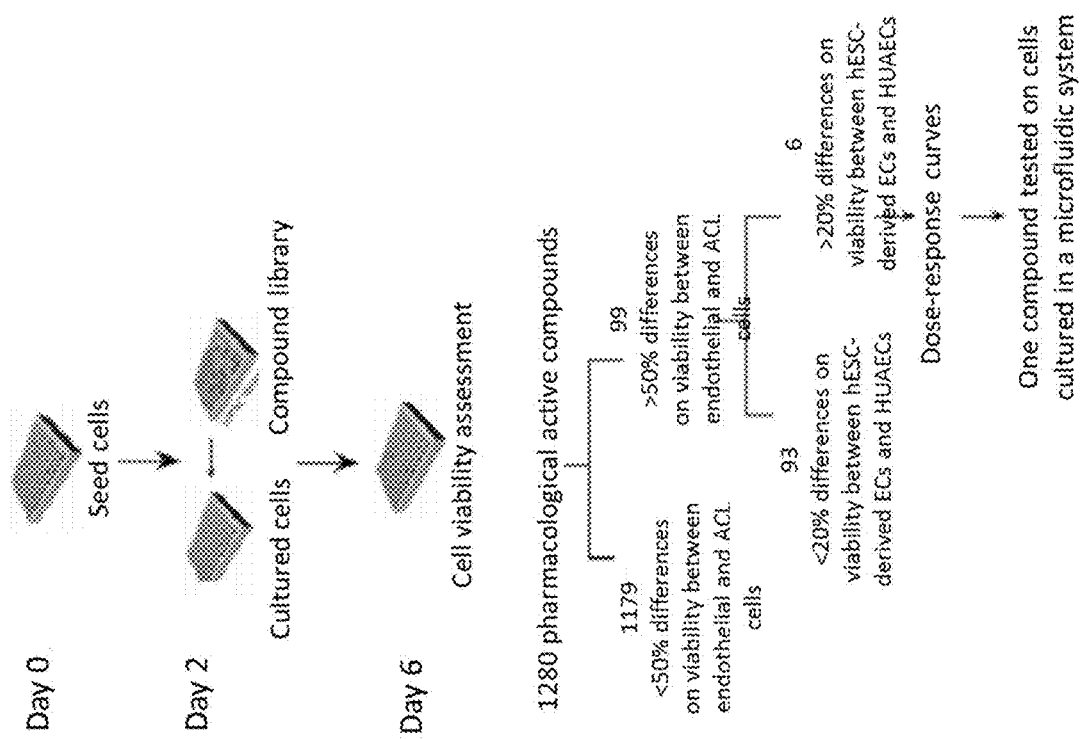
FIGS. 4A-4C: High-throughput screening (HTS) to identify compounds with embryonic vascular toxicity.
Figure 4B:
Figure 4B:
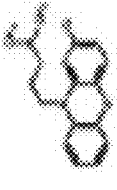
Figure 4B:
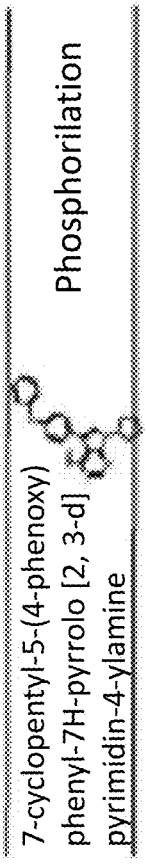
Figure 4B:
Figure 4B:
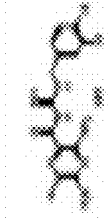
Figure 4B:
Figure 4C:
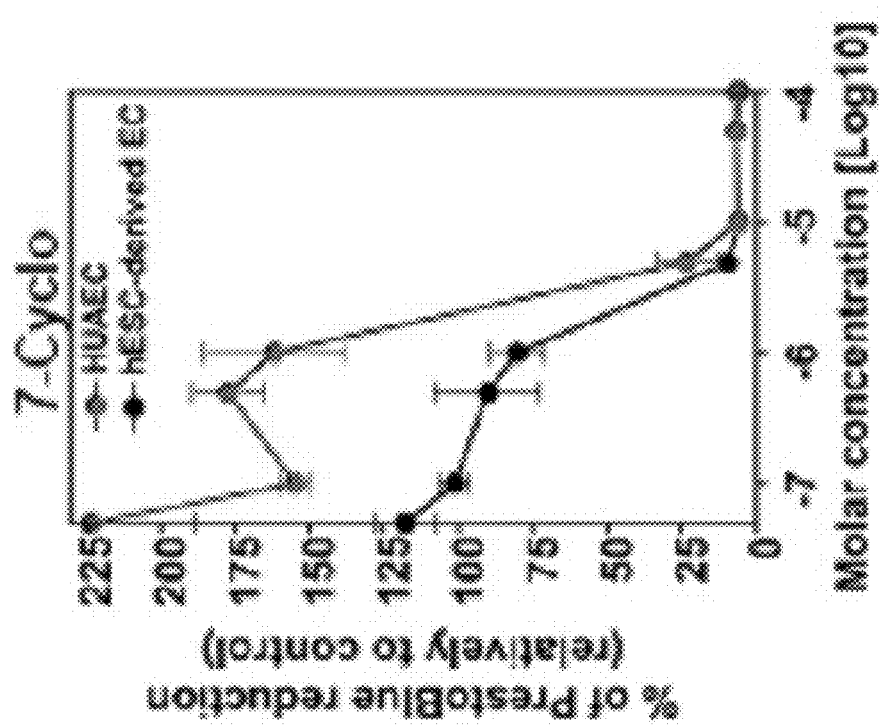
Figure 14:
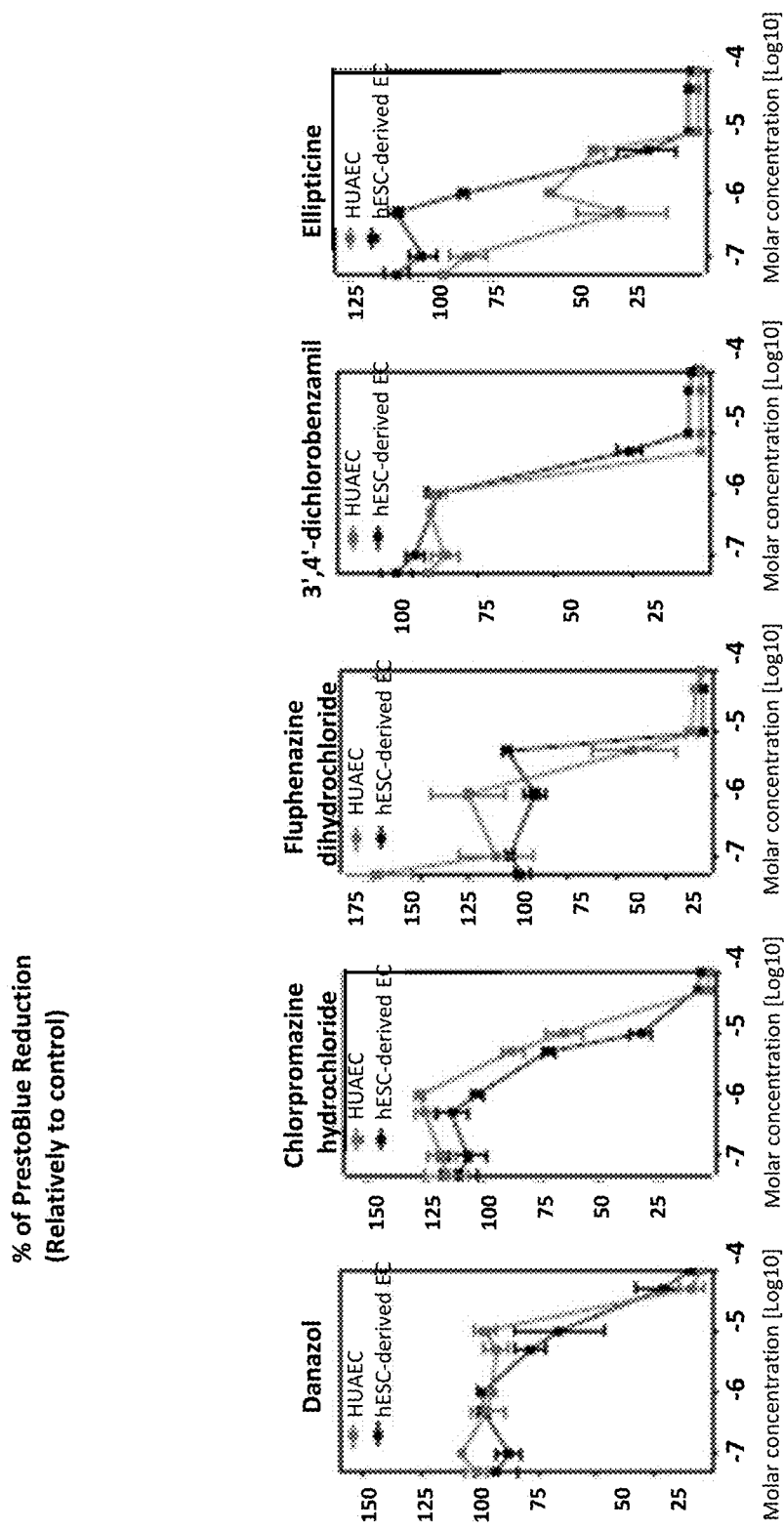
FIG. 14: Hit validation. After being selected from the primary screen, the identified compounds (hits) were subjected to a half-logaritimic dilutions in order confirm the positive hits and to assess the optimal concentration inducing cytotoxicity.

Disruption of vascular development has been directly correlated with prenatal loss, malformations and neurodevelopmental problems[41-44]. To study embryonic vascular toxicity, embryonic arterial ECs were exposed to a Library of Pharmacologically Active Compounds (LOPAC, Sigma-Aldrich) comprising 1280 bioactive compounds, and we assessed cell viability after 4 days by a PrestoBlue assay (resazurin-based solution that is reduced by viable cells) (FIG. 4A). The library was screened at a single dosage of 4.5 μM in a volume of 200 μL per well of EGM-2 medium, containing 0.25% DMSO (v/v). To identify compounds that selectively target endothelial cells, the same library against human anterior cruciate ligament cells (ACL cells) was screened. From the 1280 compounds, 99 compounds induced differences in cell viability (hESC-derived ECs versus ACL cells) above 50% and therefore were further considered for the next step (Table 4). To identify compounds that are selective to embryonic ECs but not fetal ECs were screened the library against HUAECs (FIG. 4A). Six compounds (danazol, chlorpromazine hydrochloride, ellipticine, 3',4'-dichlorobenzamil, fluphenazine dihydrochloride and 7-cyclopentyl-5-(4-phenoxy)phenyl-7H-pyrrolo[2,3-d] pyrimidin-4-ylamine) affected cell viability in both cells by a difference of 20% (FIG. 4B). The six compounds belong to different classes: cell cycle, ion pumps, dopamine pathway, phosphorylation and hormone signaling. The compounds selected from the primary screen were then tested against hESC-derived ECs and HUAECs at eight different concentrations to obtain a dose-response curve (FIG. 4C and FIG. 14). The compound 7-cyclopentyl-5-(4-phenoxy)phenyl-7H-pyrrolo[2,3-d]pyrimidin-4-ylamine (belonging to the phosphorylation class of the library and abbreviated from now on as 7-Cyclo) was chosen for further testing due to the significant effects observed between hESC-derived ECs and HUAECs.

Figure 15A:
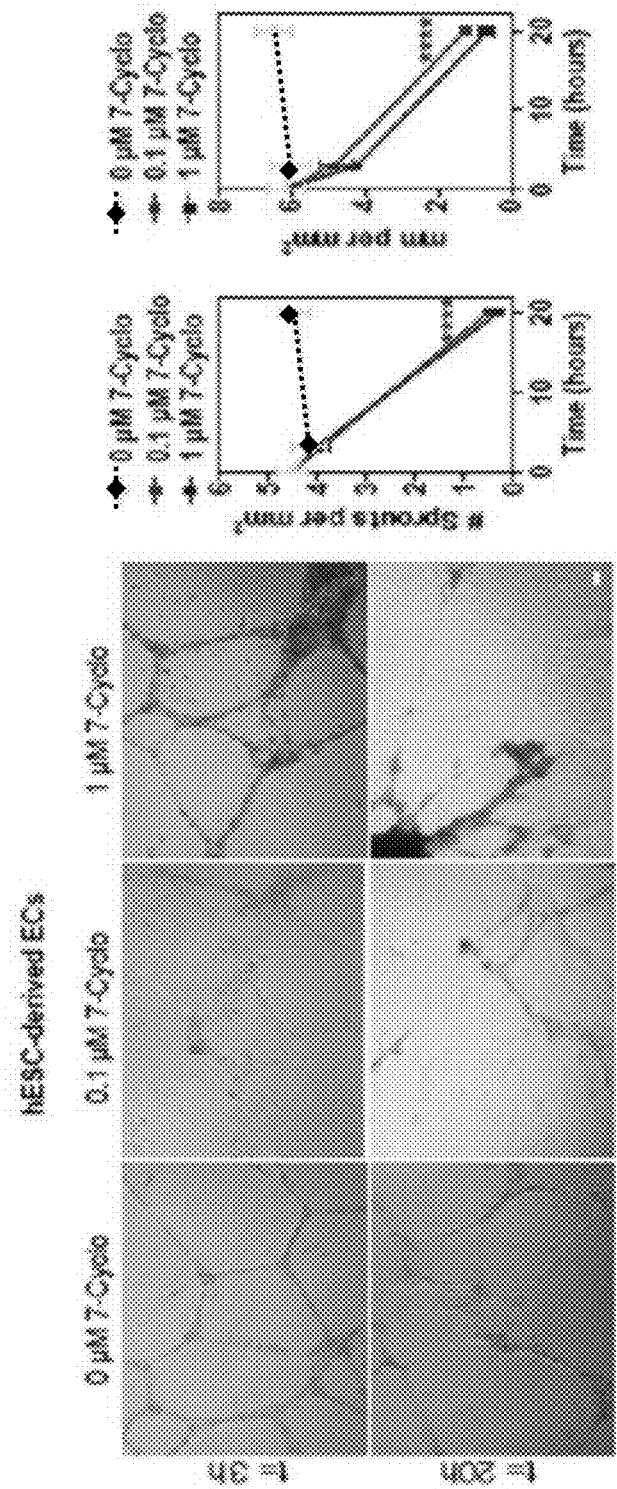
FIGS. 15A-15C: Quantification of sprouts and length of cord-like structures in hESC-derived ECs (FIG. 15A), HUAECs (FIG. 15B), and HUVECs (FIG. 15C) cultivated on top of Matrigel after 0, 3 and 20 h, with or without 7-Cyclo. Results are mean±SEM (n=8). *$P<0.01$, ****$P<0.0001$. Bar corresponds to 50 μm.
Figure 15B:
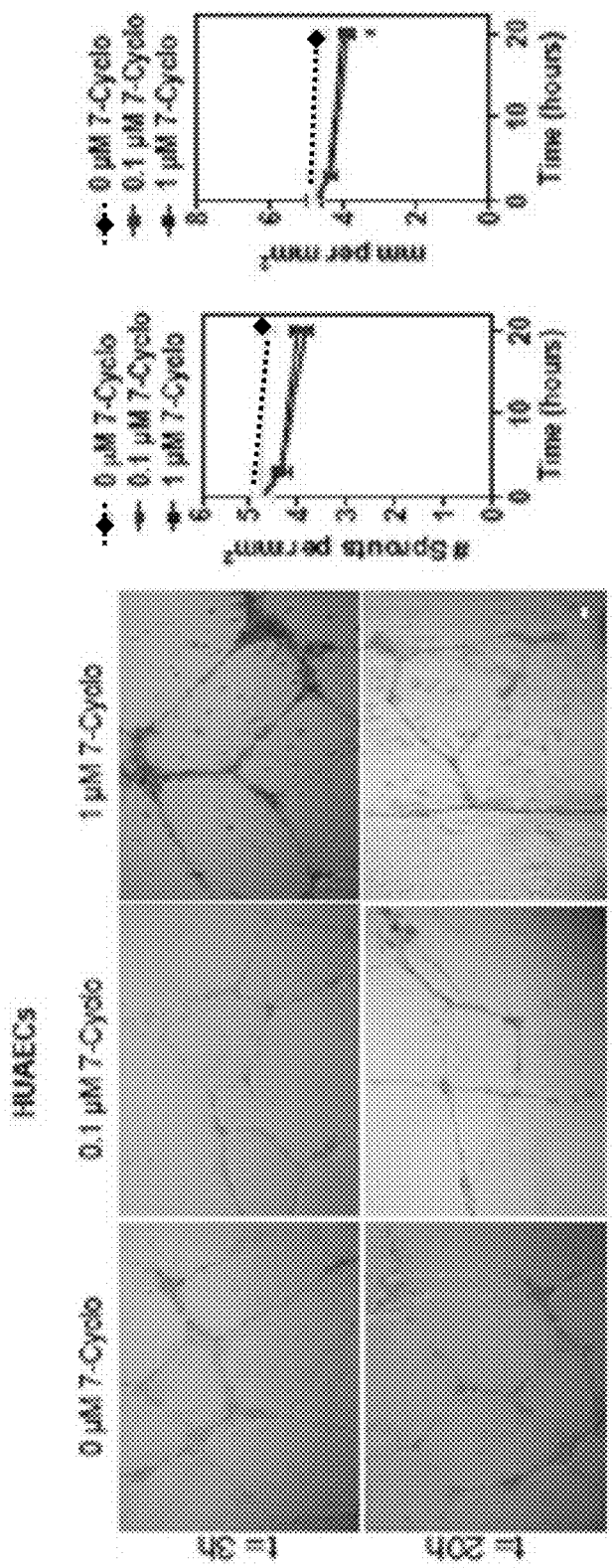
Figure 15C:
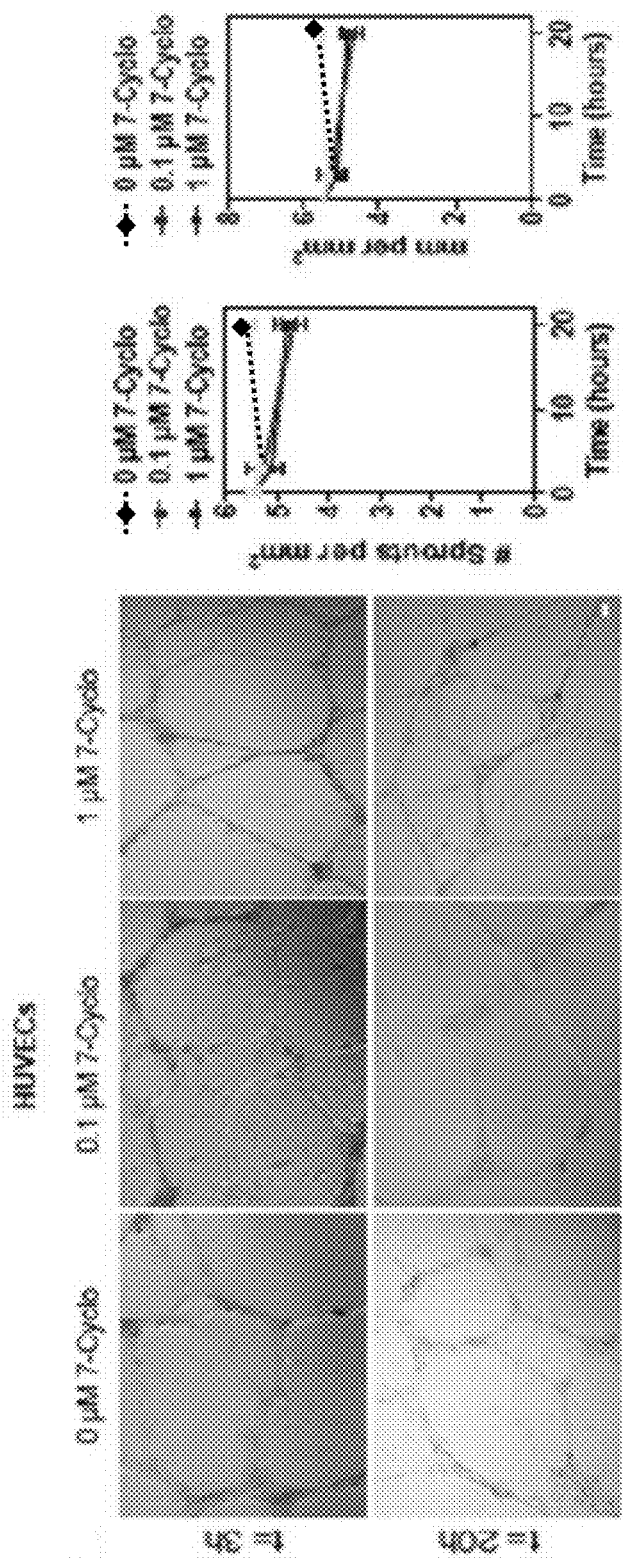

To test the 7-Cyclo properties in the disruption of vascular networks, microvessels of hESC-derived ECs, HUAECs and HAECs were formed on top of Matrigel and then exposed to the drug for 20 h. Results show that there is a statistically significant reduction in the network length and number of sprouts in microvessels formed by hESC-derived ECs after incubation with 1 μM of 7-Cyclo (FIG. 15) while negligible effect was observed in microvessels formed by HUAECs and HAECs.

Figures 5A, 5B:
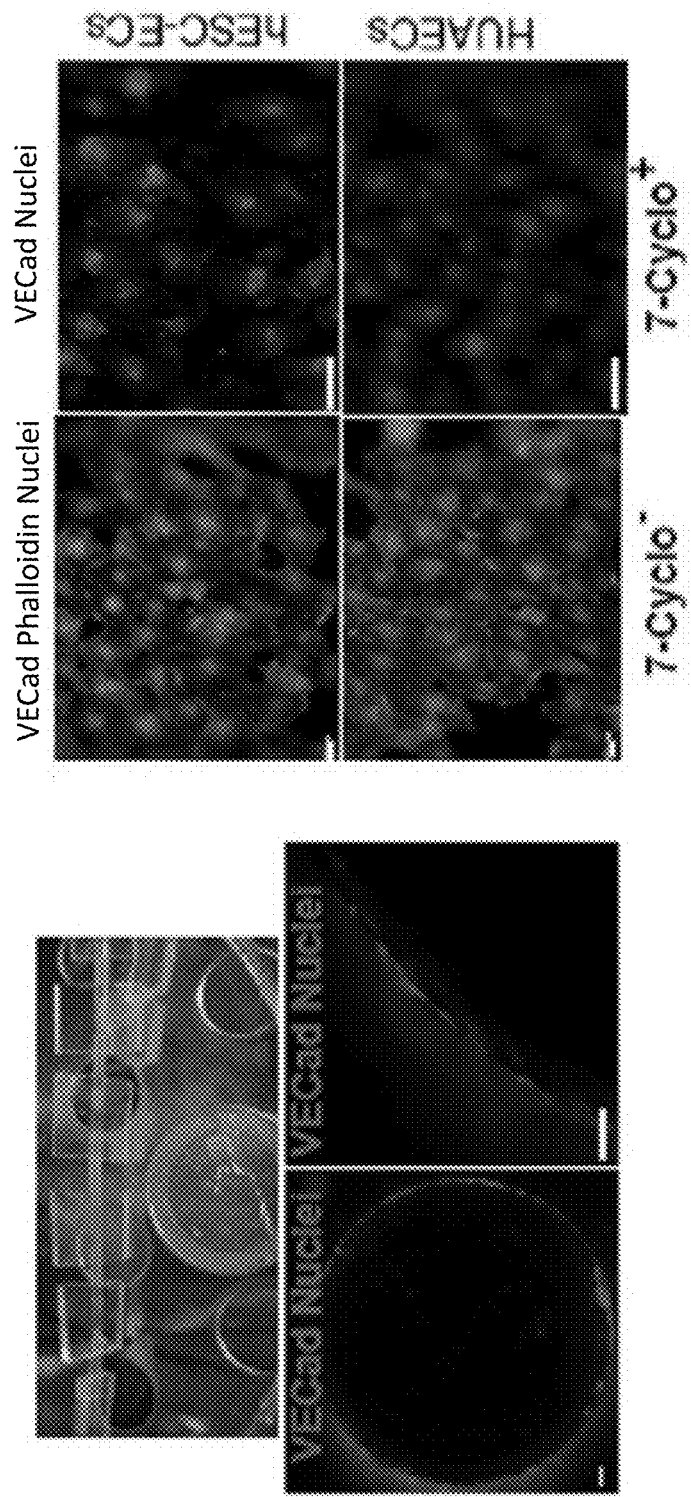
FIGS. 5A-5D: Validation of the hit 7-Cyclo in static and flow conditions.
Figure 5C:
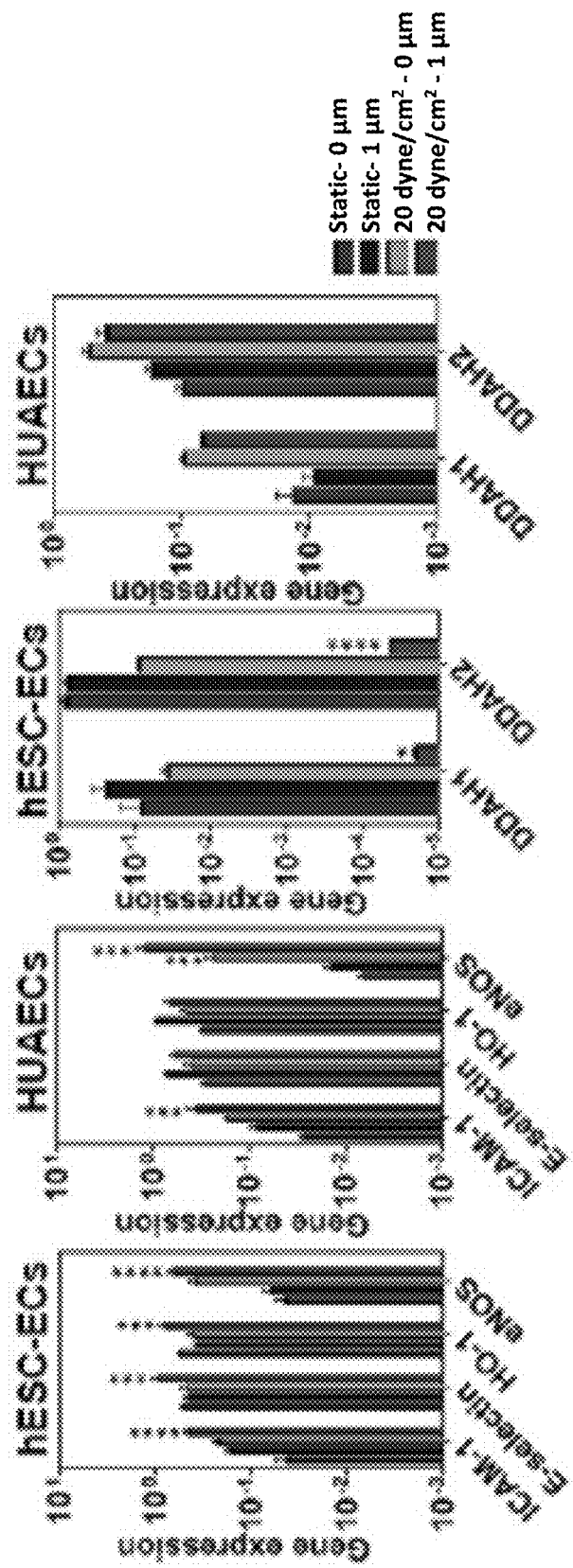
Figure 5D:
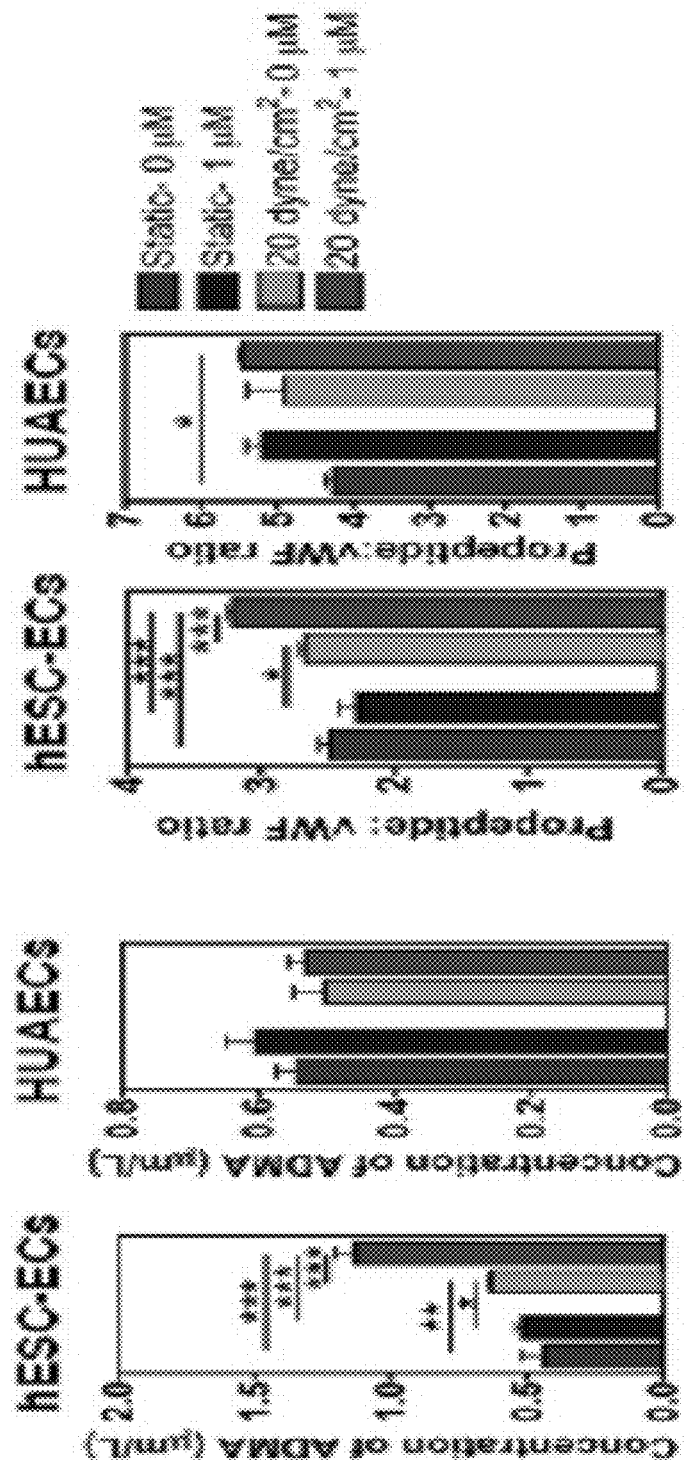

To evaluate the effects of 7-Cyclo in flow conditions, hESC-derived ECs were cultured in a poly(dimethylsiloxane) (PDMS) microfluidic system with cylindrical channels for 7 days at 20 dyne/cm2 (FIG. 5A). ECs were able to form a confluent monolayer in the entire inner surface of the channel after 48 h. At day 7, cells were exposed to EGM-2 medium supplemented with 1 μM of 7-Cyclo for 24 h, and finally analyzed at morphological, genetic and secretion levels. Results show that hESC-derived ECs show significant alterations in cell morphology in contrast to HUAECs cultured under the same conditions (FIG. 5B). In addition, hESC-derived ECs exposed to 7-Cyclo express statistically higher levels of inflammatory genes, such as ICAM-1, E-selectin, HO-1 and eNOS (P<0.0001, n=4), and express statistically lower levels of DDAH1 and DDAH2 (P<0.05 or P<0.0001, n=4), enzymes that metabolize ADMA, than cells cultured under static conditions (FIG. 5C). In case of HUAECs cultured under the same conditions, the effect was less pronounced and only ICAM-1 and eNOS genes were up-regulated. No down-regulation of DDAH-1 and DDAH-2 was observed. These gene analyses were complemented by analyses of ADMA and the ratio vWFpp: von vWF secreted by these cells (FIG. 5D). hESC-derived ECs or HUAECs cultured in static conditions in the presence of the drug have similar secretion of ADMA or vWFpp:vWF as in control conditions (i.e., without the drug). Importantly, hESC-derived ECs cultured under flow conditions in the presence of 7-Cyclo secrete higher levels of ADMA (2.5 fold) and vWFpp:vWF (1.6 fold) than without the drug, and significant higher levels of ADMA than HUAECs. Overall, results indicate that hESC-derived ECs are more sensitive to the effect of 7-Cyclo than HUAECs showing high levels of vascular dysfunction.

Figure 6A:
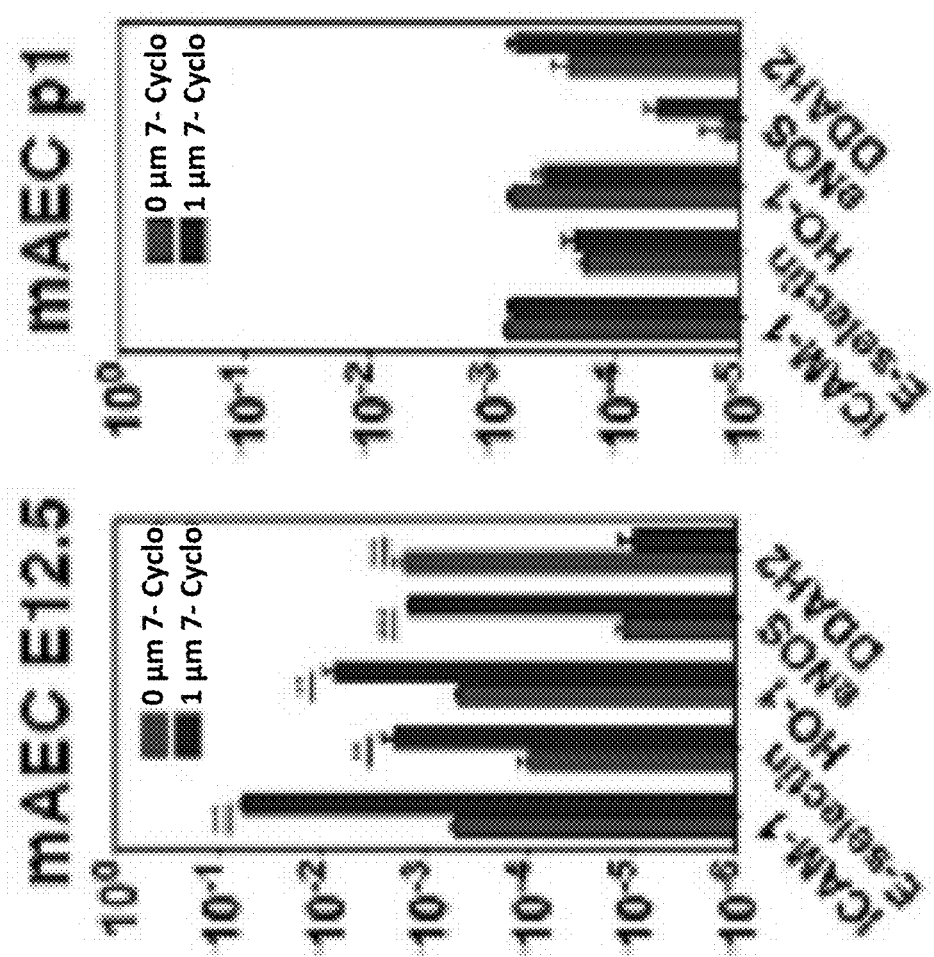
FIGS. 6A-6D: Mechanism of 7-Cyclo.

To further validate the effects of 7-Cyclo at the embryonic vasculature, mouse embryonic ECs were incubated at day 12.5 (mAEC E12.5) and postnatal day 1 (p1) with 7-Cyclo (1 μM) for 24 h. Inflammation, oxidative stress sensing, vascular modulation and vascular injury sensing genes are statistically up-regulated in mouse aortic endothelial cells (mAEC) at E12.5 as compared to cells without treatment (FIG. 6A). In contrast, 7-Cyclo has no effect in p1 ECs. The degree of action of 7-Cyclo in mAEC E12.5 is similar to the one identified in hESC-derived ECs (FIG. 5C).

Mechanism of 7-Cyclo in Embryonic ECs

Figure 6B:
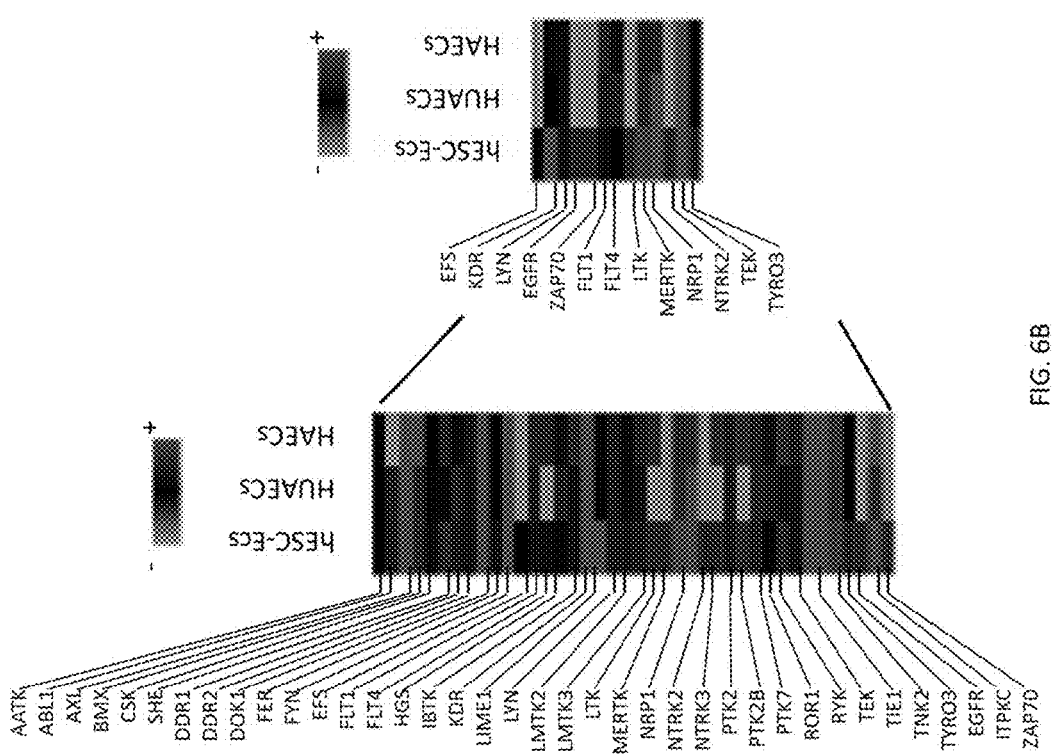
Figure 6C:
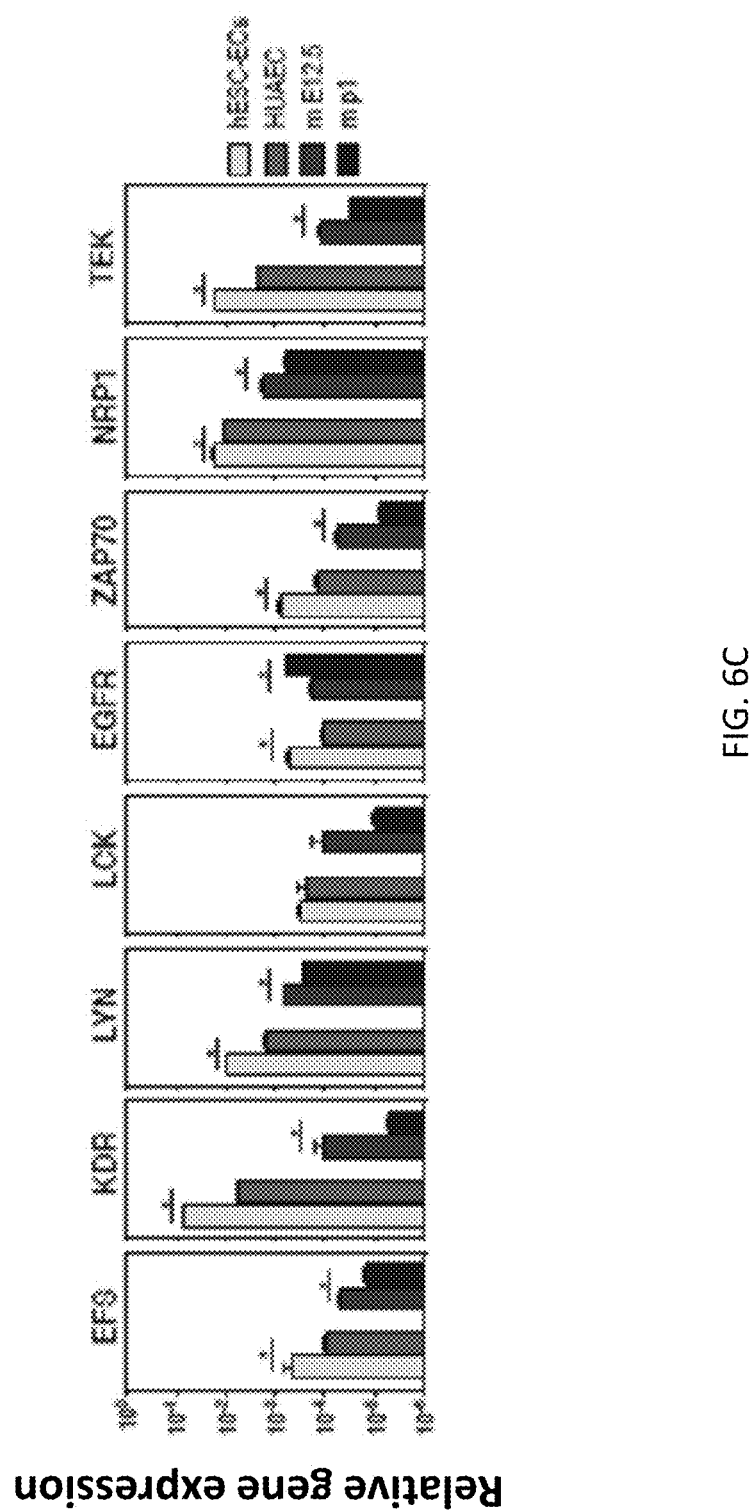

7-Cyclo is a cell-permeable pyrrolopyrimidine that acts as a potent inhibitor of tyrosine kinases such as SRC, KDR, TIE-2, BLK, FYN, LYN, CSK, EGFR, PKC, CDC2/B and ZAP-7045. To understand the distinctive effect of 7-Cyclo in embryonic versus fetal/adult ECs gene microarray data was analyzed and compared the expression of tyrosine kinases. From a group of 38 tyrosine kinases (FIG. 6B and Table 4), which includes some of the most (EFS, KDR, LYN, LKC)

and less affected (EGFR, ZAP70) tyrosine kinases by 7-Cyclo in human cells (FIG. 6B, left panel), 8 of them (KDR, LYN, FLT1, FLT4, MERTK, NRP1, TEK, TYRO3) were higher expressed in hESC-derived ECs than in HUAECs or HEACs. In fact, some tyrosine kinases were only expressed in hESC-derived EC (EFS, EGFR, ZAP70, LTK, NTRK2). The expression of the most significant genes (EFS, KDR, LYN, LCK, EGFR, ZAP70, NRP1 and TEK) was further characterized and confirmed by qRT-PCR (FIG. 6C). The qRT-PCR included the analysis of mouse embryonic and postnatal ECs, to validate the results obtained for hESC-derived ECs. The same trend was observed, i.e, tyrosine kinases were found to be more expressed in embryonic ECs (both in human and mouse) than in fetal/adult tissues (exception for EGFR in mouse).

Figure 6D:
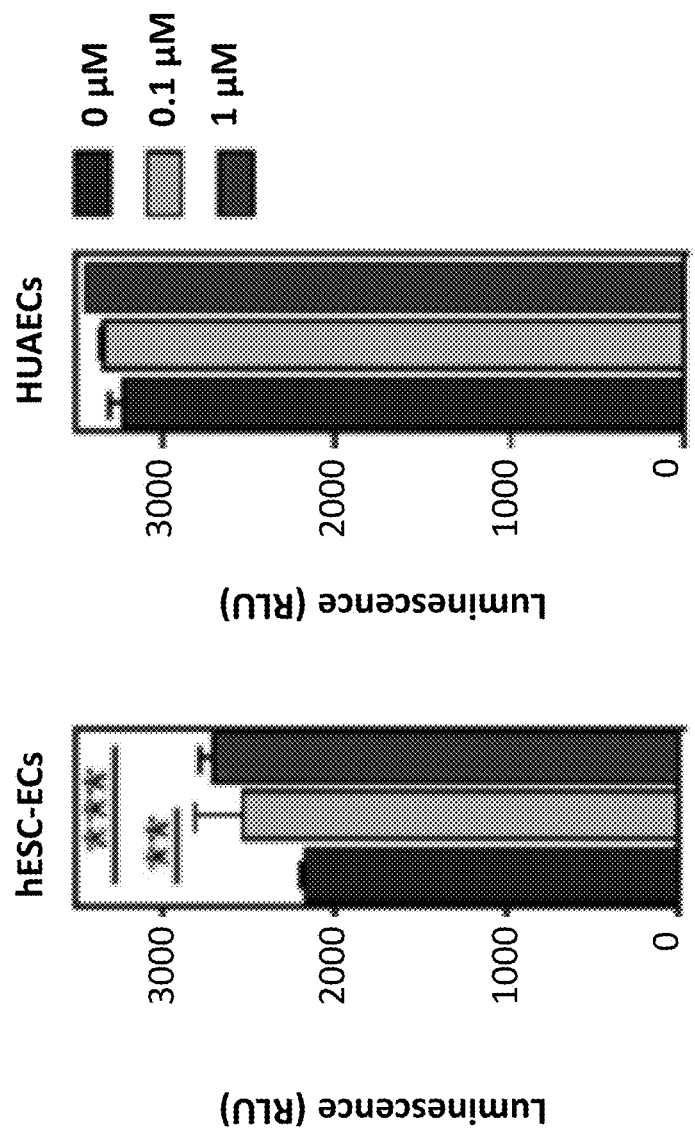

Interestingly the expression of LCK, one of the targets of 7-Cyclo 46, was expressed at similar magnitude in hESC-derived ECs and HUAECs, as assessed by qRT-PCR, and thus the differences observed between embryonic and fetal/adult ECs are likely mediated by other tyrosine kinases described above. The kinase activity of the hESC-derived ECs and HUAECs was assessed by luminescence (signal is inversely correlated with the level of kinase activity) in the absence or presence of the compound 7-Cyclo (FIG. 6D). After 24 h incubation with 7-Cyclo (0.1 or 1 µM) the kinase activity of hESC-derived ECs decreased significantly from time zero (P<0.01), while no significant decrease was observed in HUAECs. Overall results indicate that 7-Cyclo affects hESC-derived ECs likely inhibiting tyrosine kinases highly expressed in the embryonic state such as KDR, LYN, FLT1, FLT4, MERTK, NRP1, TEK or TYRO3.

Expanded Materials and Methods:

hESC Culture and Differentiation.

Undifferentiated hESCs (passages 33-36; H9, WiCell, Wisconsin) or hiPSCs K2 (passages 32-35; cord blood derived iPSCs kindly donated by Ulrich Martin) were grown on an inactivated mouse embryonic fibroblast (MEF) feeder layer, as previously described 1, 2. To induce the formation of EBs, the undifferentiated hESCs were treated with 2 mg/mL type IV collagenase (Invitrogen) for 2 h and then transferred (2:1) to low attachment plates (Corning) containing 10 mL of differentiation medium [80% KO-DMEM, 20% fetal bovine serum (FBS, Invitrogen), 0.5% L-glutamine, 0.2% β-mercaptoethanol, 1% nonessential amino acids]. The differentiation medium was supplemented with VEGF165 (50 ng/mL, Prepotech), Tβ4 (100 ng/mL, Caslo) and SB431542 (10 µM, Tocris) according to different timelines (see below). After 4 days in suspension, EBs were plated onto 1% gelatin-coated dishes and grown for 14 additional days. Medium was changed every 2-3 days. The experimental conditions tested were: (i) EB medium only (Prot1), (ii) EB medium supplemented with (ii) (VEGF165) days0-18 (Prot2), or (iii) [(VEGF165)days0-18+ (SB431542, 10 µM)days7-18] (Prot3), or (iv) (VEGF165+ Tβ4)days0-18 (Prot4), or (v) [(VEGF165)days0-18+(Tβ4) days4-18] (Prot5), or (vi) [(VEGF165+Tβ4)days0-18+ (SB431542)days7-18] (Prot6), or (vii) [(VEGF165)days0-18+(Tβ4)days4-18+(SB431542)days7-18] (Prot7) (FIG. 7A). Protocol 7 gave the best results in terms of differentiation of hESCs into CD31+ cells.

Human and Mouse Primary Cells.

HUAEC (human umbilical arterial endothelial cells) and HUVEC (human umbilical venous endothelial cells) were bought from Lonza (http://www.lonza.com/). Total RNA of human Aortic Endothelial cells, mouse aortic endothelial cells (E 12.5 and p1) were bought from ScienceCell (http://www.sciencellonline.com/).

Flow Cytometry Analysis.

Cells were tripsinized, aliquoted ($1.25$-$2.5 \times 10^5$ cells per condition), washed in PBS, centrifuged at 1200 g and then resuspended in PBS containing 5% FBS. Cells were labeled with human CD31 monoclonal antibody (eBioscience, clone: WM59; 1.25:100), CD34 (Miltenyi Biotec, clone: AC136; 5:100), vwF (Dako; clone F8/86; 1:50), Flk-1/KDR (R&D, clone: 89106; 5:100), VeCad (R&D, clone: 123413; 5:100) or EphB2 (R&D, clone: 512012; 5:100). Cells were characterized on a FACS Calibur (BD) and the data analyzed by Cell Quest software. Twenty thousand events were collected in each run.

Quantitative Reverse Transcription-Polymerase Chain Reaction (qRT-PCR) Analysis.

Total RNA from experimental groups was isolated using a protocol with TRIzol (Invitrogen) and RNeasy Minikit (Qiagen, Valencia). cDNA was prepared from 1 µg total RNA using Taqman Reverse transcription reagents (Applied Biosystems, CA). Quantitative PCR (qPCR) was performed using Power SYBR Green PCR Master Mix and the detection using an ABI PRISM 7500 Fast System (Applied Biosystems). Quantification of target genes was performed relative to the reference GAPDH gene: relative expression=$2^{[-(Ct_{sample} - Ct_{GADPH})]}$. The mean minimal cycle threshold values (Ct) were calculated from 4 reactions. In some cases, gene expression in each experimental group was normalized to the relative gene expression found in HUVECs, HUAECs or undifferentiated hESCs. Primer sequences are published in Table 7 of expanded materials and methods.

Matrigel Assay.

A 24-well plate was coated with Matrigel (0.4 mL, BD Biosciences) per well and incubated at 37° C. for 30 min. Cells were seeded on top of the polymerized Matrigel at a concentration of $1 \times 10^5$ cells per 300 µL of EGM-2 medium. After 1 h of incubation at 37° C., an extra 1 mL of EGM-2 was added. After 12 h, medium supplemented with 7-Cyclo (0, 0.1 or 1 µM) was added. Cord formation was evaluated by phase contrast microscopy (Carl Zeiss International, Germany), at time 0, 3 h and 20 h after 7-Cyclo addition.

Intracellular $Ca^{2+}$ Variation Measurements.

HUVECs, HUAECs or hESC-derived ECs were loaded with Fura-2 calcium fluorescent indicator by incubation with 5 µM of the membrane permeable acetoxymethyl (AM) derivative FURA-2/AM (1 mM in DMSO, Molecular Probes, http://www.invitrogen.com) and 0.06% (w/v) Pluronic F-127 (Sigma, http://www.sigmaaldrich.com), using basal medium (M199, Sigma) as vehicle (35 µl/well, not supplemented with serum nor antibiotics), for 1 h at 37° C. in 5% $CO_2$ and 90% humidity. The medium was then replaced by the respective basal medium and cells were incubated in the same conditions for 30 min to allow hydrolysis of the acetoxymethyl (AM) esters by cellular esterases, resulting in intracellular capture of the membrane impermeant Fura-2. Afterwards cells were washed twice with 100 µL sodium salt solution (140 mM NaCl, 5 mM KCl, 1 mM $CaCl_2$, 1 mM $MgCl_2$, 10 mM Glucose, 10 mM HEPES-$Na^+$ pH 7.4). The buffer was replaced again (100 µl/well) immediately prior to incubating or not with test compounds.

Cells located in wells on a plate row were incubated at 25° C. (inside the microplate reader, during basal reading). Cells were then stimulated with 100 µM Histamine[53,54] (Sigma), 100 ng $VEGF_{165}$ (Prepotech, www.peprotech.com)[55,56], 10 µM Prostaglandin U46619 (Cayman, http://www.cayman-chem.com)[57,58], 50 mM KCl[53,54] (Merck, http://www.merck.com) or 2U Thrombin (Sigma)[59] by adding 1 µl of a stock solution. Fluorescence was measured at emission 510 nm using two alternating excitation wavelengths (340 nm and 380 nm)[60] using a microplate fluorescence reader (Spectramax Gemini EM, Molecular Devices, with SoftMax® Pro software). The microplate reader was set to "top-read kinetics"; PMT was "high"; temperature was 25° C.; each fluorescence time point was an average of 18 reads; and during basal/inhibitors incubation periods and KCl/Histamine stimulation, each well was read every 3 sec. Fluorescence intensity values (in relative fluorescence units—RFU) measured at 340 nm and 380 nm were taken from the stabilized signal obtained at basal conditions and after incubation or not with the inhibitors. Following stimulation with Histamine/KCl, the fluorescence values were taken from the time point at the peak of the response. Typically, each experiment consisted of three or four wells plus three or four wells containing cells incubated with inhibitors and all cells were stimulated and read simultaneously. The dose-response curves for the effect of stimuli on the intracellular $Ca^{2+}$ variation were determined using the software GraphPad Prism™.

Kinase Activity Quantification.

The kinase activity of cells was measured by a Kinase-Glo® Luminescence Kinase Assay (Promega). Cells incubated with 7-Cyclo for 24 h were treated with the kinase reagent from the kit and luminescence acquired using a Spectra Max Gemini luminometer. The luminescence signal is correlated with the amount of ATP present and its inversely correlated with the amount of kinase activity.

Shear Stress Calculations.

Using the Poiseuille's Law equation for laminar flow $TS=(4 \mu Q)/(\pi R^3)$, where TS is hemodynamic shear stress, $\mu$ is fluid viscosity, Q is flow and R radius; a laminar flow of 29 mL/min was used to apply 20 dyne/cm² shear stress on a 0.45 mm radius channel seeded with cells as described before.

Microarray Procedure and Data Analysis.

RNA isolation and sample labeling. hESC-derived EC, HUAEC or AEC (adult aortic endothelial cells) were homogenized in Trizol reagent (Invitrogen) and total RNA was extracted by using the RNeasy Mini Kit (Qiagen, Valencia, USA), according to manufacturer's instructions. The quality of the RNA was assessed in the Agilent 2100 Bioanalyser (G2943CA) using the RNA 6000 Pico Kit (5067-1513). Before labeling, a mixture of ten in vitro synthesized RNAs were added to total RNA to allow for hybridization quality control and normalization of the microarrays. The RNA was amplified and labeled according to the One-Color Microarray-Based Gene Expression Analysis (Agilent). The efficiency of cRNA synthesis and dye incorporation was measured using NanoDrop ND-1000 UV-VIS spectrophotometer and samples with neither a yield below 1.65 µg nor a specific activity (pmol Cy3 per ug cRNA) below 6 were not considered for hybridization.

Microarray Hybridization.

Labeled cRNA was hybridized to the Whole Human Genome (4×44K) Microarray (G4112F from Agilent Technologies). From each sample, 1.65 µg cyanine 3-labeled cRNA was adjusted to 41.8 µl with DNAse-free Water, mixed with 11 µl Agilent 10× blocking Agent and 2.2 µl Fragmentation Buffer and incubated at 60° C. for exactly 30 minutes to fragment RNA. To stop de fragmentation reaction 55 µl of 2× GEx Hybridization Buffer was added. After a short spin-down, the labelled cRNA mixture was applied to a microarray slide, assembled in a SureHyb Hybridization Chamber fitted with a gasket slide (Agilent), and incubated for 18H at 65° C. in a hybridization oven (G2545A, SHEL LAB—Agilent), with 10 rpm rotation speed. Slides were washed as described in the Agilent One-Color Microarray-Based Gene Expression Analysis protocol. Afterwards, the microarray and gasket slide were briefly disassembled inside a staining dish containing 250 ml of GE Wash Buffer 1 and the slides (up to 4 slides) were washed in fresh 250 ml of GE Wash Buffer 1 solution at room temperature, during 1 minute, with gentle agitation from a magnetic stirrer. A second wash step was carried out by immersing the slides in GE Wash Buffer 2 solution, previously warmed to 37° C., during 1 minute, also with gentle magnetic stirring. Finally, slides were dried by centrifugation at 800 rpm for 3 minutes.

Image Acquisition and Data Processing.

Microarrays were scanned in the Agilent B Scanner (G2565BA) using specific scanning protocols for gene expression microarrays and the format 4×44K. Agilent Feature Extraction Image Analysis Software (Version 10.7.3.1) was used to obtain fluorescence intensities from raw microarray image files.

Normalization and Analysis of DNA Microarray Data.

Analysis of raw data was performed using BRB-ArrayTools v3.4.0 developed by Dr. Richard Simon and BRB-ArrayTools Development Team[54]. BRB-Array Tools incorporates the Bioconductor R functions and the R programming language required for raw data normalization within arrays[55]. Each gene's measured intensity was median normalized to correct for differences in the labelling efficiency between samples. This analyzes provided a median normalized dataset that was subjected to statistical analysis and clustering using MeV software[56]. Here, genes were identified as differentially expressed using the following criteria: (i) Test-design: between subjects (test vs control); (ii) Variance assumption: Welch approximation; (iii) P-value parameters: p-values based on t-distribution; alpha critical p-value=0.001; (iv) False discovery corrections: just alpha Gene Expression Regulation Analysis.

The previous step provided a differentially expressed genes (DEGs) list for each strain that was used to calculate the M-value and Fold-change variation. It was considered as differentially expressed a variation equal or higher than 2× between conditions. Only genes with significance level below an alpha corrected p-value of $10^{-3}$ were considered as differentially expressed. The down- and up-regulated genes were analyzed using DAVID 6.7 (Database for Annotation, Visualization and Integrated Discovery, http://david.abcc.ncifcrf.gov/) web-accessible program to identify the altered cellular processes and functions. The microarray data has been deposited in NCBI's Gene Expression Omnibus database and is accessible through the GEO series accession number GSE51642.

TABLE 1

Primers used for Real Time PCR[1]

| | | Sense | | Antisense |
|---|---|---|---|---|
| GAPDH [1] | SEQ ID NO: 1 | AGCCACATCGCTCAGACACC | SEQ ID NO: 60 | GTACTCAGCGCCAGCATCG |

TABLE 1-continued

Primers used for Real Time PCR[1]

| | Sense | | | Antisense | |
|---|---|---|---|---|---|
| PCAM [1] | SEQ ID NO: 2 | GCTGTTGGTGGAAGGAGTGC | SEQ ID NO: 61 | GAAGTTGGCTGGAGGTGCTC | |
| CD34 [1] | SEQ ID NO: 3 | TGAAGCCTAGCCTGTCACCT | SEQ ID NO: 62 | CGCACAGCTGGAGGTCTTAT | |
| VECad [1] | SEQ ID NO: 4 | ACGGGATGACCAAGTACAGC | SEQ ID NO: 63 | ACACACTTTGGGCTGGTAGG | |
| vWF [1] | SEQ ID NO: 5 | ATGTTGTGGGAGATGTTTGC | SEQ ID NO: 64 | GCAGATAAGAGCTCAGCCTT | |
| Flk-1 [1] | SEQ ID NO: 6 | CTGGCATGGTCTTCTGTGAAGCA | SEQ ID NO: 65 | AATACCAGTGGATGTGATGGCGG | |
| Oct-4 [11] | SEQ ID NO: 7 | GTGGAGGAAGCTGACAACAA | SEQ ID NO: 66 | CTCCAGGTTGCCTCTCACTC | |
| EphB4 | SEQ ID NO: 8 | CTCAGTTCGGATCCTACC | SEQ ID NO: 67 | AATGTCACCCACTTCAGAT | |
| Lefty-1 | SEQ ID NO: 9 | CTGACAAGTTACCTCACCTA | SEQ ID NO: 68 | GACACATTGGGCTTTCTG | |
| Lefty-2 | SEQ ID NO: 10 | GAACTGAATTGCTGTGTTATATG | SEQ ID NO: 69 | AACCAGAATCCAGGTATCC | |
| Notch1 | SEQ ID NO: 11 | ATCTGAAATAGGAAACAAGTGAA | SEQ ID NO: 70 | ATAACCAACGAACAACTACATAA | |
| Notch2 | SEQ ID NO: 12 | AACATCTCATCCATGCTTTG | SEQ ID NO: 71 | ACAGTGGTACAGGTACTTC | |
| Notch3 | SEQ ID NO: 13 | CGCTCGTCAGTTCTTAGA | SEQ ID NO: 72 | AAGGAAGGAAGAGACAGAG | |
| Notch4 | SEQ ID NO: 14 | ATTGACACCCAGCTTCTT | SEQ ID NO: 73 | GAGGACAAGGGTCTTCAA | |
| DLL3 | SEQ ID NO: 15 | TGTCCGTGAAATGAATTGG | SEQ ID NO: 74 | AAGAGAAGATGGCAGGTAG | |
| DLL4 | SEQ ID NO: 16 | GGAGGTATAAGGCAGGAG | SEQ ID NO: 75 | AGGTGTGGAAGGGTATTG | |
| JAG1 | SEQ ID NO: 17 | GTCTCAAAGAAGCGATCAG | SEQ ID NO: 76 | ATATACTCCGCCGATTGG | |
| JAG2 | SEQ ID NO: 18 | ACAATGGAGTATTCTCGGATA | SEQ ID NO: 77 | CTGGTAACAAACGCTACG | |
| EFNB1 | SEQ ID NO: 19 | CAACACTGTCAAGATGGC | SEQ ID NO: 78 | CTCTTCTCTTCCTGGTTCA | |
| EFNB2 | SEQ ID NO: 20 | CCACAGATAGGAGACAAATTG | SEQ ID NO: 79 | AGTTGAGGAGAGGGGTAT | |
| ALDH1A1 | SEQ ID NO: 21 | GAGTTTGTTCATCCAATCGTA | SEQ ID NO: 80 | GGTGAGTAGGACAGGTAAG | |
| Hey-2 | SEQ ID NO: 22 | ACAACTTCAGAAGTGCCT | SEQ ID NO: 81 | GACAAGAGAGAGGTGGAG | |
| ICAM-1 | SEQ ID NO: 23 | CAAGGCCTCAGTCAGTGTGA | SEQ ID NO: 82 | CCTCTGGCTTCGTCAGAATC | |
| E-selectin | SEQ ID NO: 24 | AGCTTCCCATGGAACACAAC | SEQ ID NO: 83 | CTGGGCTCCCATTAGTTCAA | |
| eNOS | SEQ ID NO: 25 | GATGCTCCCAACTTGACCTTGACCAT | SEQ ID NO: 84 | TAGGTCTTGGGGTTGTCAGG | |
| HO-1 | SEQ ID NO: 26 | GAAAAGCACATCCAGGCAAT | SEQ ID NO: 85 | GCTGCCACATTAGGGTGTCT | |

TABLE 1-continued

Primers used for Real Time PCR[1]

| | Sense | | Antisense | |
|---|---|---|---|---|
| DDAH1 | SEQ ID NO: 27 | GGACAAATCAACGAGGTGCT | SEQ ID NO: 86 | TAGCGGTGGTCACTCATCTG |
| DDAH2 | SEQ ID NO: 28 | CTGTTGTGGCAGGCAGCAG | SEQ ID NO: 87 | GTCAGGGAGGCATATGGGTG |
| TAL1 | SEQ ID NO: 29 | ATGGAGATTACTGATGGTCC | SEQ ID NO: 88 | AGGATCTCATTCTTGCTGAG |
| PTPRU | SEQ ID NO: 30 | ACATAGATGGTTACCACAGG | SEQ ID NO: 89 | AGAAGTCATAGACCATCTCAG |
| CDH2 | SEQ ID NO: 31 | ACATATGTGATGACCGTAAC | SEQ ID NO: 90 | TTTTTCTCGATCAAGTCCAG |
| ANGP1 | SEQ ID NO: 32 | ATGTTAACAGGAGGATGGTG | SEQ ID NO: 91 | GAAGTAGTGCCACTTTATCC |
| ID1 | SEQ ID NO: 33 | ACTAGTCACCAGAGACTTTAG | SEQ ID NO: 92 | AAATCTGAGAAGCACCAAAC |
| EFS | SEQ ID NO: 34 | ACCTCATCTACAAAATCCCC | SEQ ID NO: 93 | ACATCATAGGGAGCATCATC |
| KDR | SEQ ID NO: 35 | GTACATAGTTGTCGTTGTAGG | SEQ ID NO: 94 | TCAATCCCCACATTTAGTTC |
| LYN | SEQ ID NO: 36 | CAACACCTTAGAAACAGAAGAG | SEQ ID NO: 95 | CTCTAATAAGGAAAGCTCCAG |
| LCK | SEQ ID NO: 37 | ATGGGAGTCTAGTGGATTTTC | SEQ ID NO: 96 | GGTCACGATGAATATAATTCCG |
| EGFR | SEQ ID NO: 38 | TCTTAAAGACCATCCAGGAG | SEQ ID NO: 97 | ATCTGCAGGTTTTCCAAAG |
| ZAP70 | SEQ ID NO: 39 | CTGGATCTACAAGTGGGAG | SEQ ID NO: 98 | CCAGGCTGTAGTAACAGG |
| NRP1 | SEQ ID NO: 40 | AGAAGATTGTGCAAAACCAG | SEQ ID NO: 99 | TAAGGTCTTCAACACATTGC |
| TEK | SEQ ID NO: 41 | GTGATTGACACTGGACATAAC | SEQ ID NO: 100 | ACTTGAATATGTTGCCAAGC |
| mouseICAM-1 | SEQ ID NO: 42 | CAGTCTACAACTTTTCAGCTC | SEQ ID NO: 101 | CACACTTCACAGTTACTTGG |
| mouseE-selectin | SEQ ID NO: 43 | CATGAAATGTCTTCCCAGTG | SEQ ID NO: 102 | ATCACATTTCACAGCTGAAC |
| mouseeNOS | SEQ ID NO: 44 | AAAGCTGCAGGTATTTGATG | SEQ ID NO: 103 | AGATTGCCTCTATTTGTTGC |
| mouseHO-1 | SEQ ID NO: 45 | CATGAAGAACTTTCAGAAGGG | SEQ ID NO: 104 | TAGATATGGTACAAGGAAGCC |
| mouseDDAH2 | SEQ ID NO: 46 | GACTCCCATCTTCATTAACTC | SEQ ID NO: 105 | TTCTCTTGACTTCACTGGTC |
| mouseTAL1 | SEQ ID NO: 47 | AGATGGAGATTTCTGATGGTC | SEQ ID NO: 106 | TTGCTTAGTTTCTTGTCTGG |
| mousePTPRU | SEQ ID NO: 48 | GGACATGATCTTTCTCAAGTG | SEQ ID NO: 107 | TGGTAGCTGATCTCATACTG |
| mouseCDH2 | SEQ ID NO: 49 | GAGTTTACTGCCATGACTTTC | SEQ ID NO: 108 | TCCACCACTGATTCTGTATG |
| mouseANGP1 | SEQ ID NO: 50 | CTGGAAGGAGTATAAAATGGG | SEQ ID NO: 109 | TTCCTATGTGGAATCTGTCG |
| mouseID1 | SEQ ID NO: 51 | ATCTCTGGGAAAGACACTAC | SEQ ID NO: 110 | ATAAACAGAAACACGCGG |

TABLE 1-continued

Primers used for Real Time PCR[1]

| | | Sense | | | Antisense |
|---|---|---|---|---|---|
| mouseEFS | SEQ ID NO: 52 | GGAATATGACTACGTGCATC | SEQ ID NO: 111 | | TAGAAGTGCAGAAGTTGGAG |
| mouseKDR | SEQ ID NO: 53 | GACGGATGATCAAGAGAAATAG | SEQ ID NO: 112 | | GTACCATTTGATATCAGGAGC |
| mouseLYN | SEQ ID NO: 54 | GAAGCCATGGGATAAAGATG | SEQ ID NO: 113 | | TGTTATAGTAACCCATCCAGAC |
| mouseLCK | SEQ ID NO: 55 | GTGAAGAGTCTGAAACAAGG | SEQ ID NO: 114 | | GGGAGTCTTGAGAAAATCTAC |
| mouseEGFR | SEQ ID NO: 56 | CTGTCGCAAAGTTTGTAATG | SEQ ID NO: 115 | | GAATTTCTAGTTCTCGTGGG |
| mouseZAP70 | SEQ ID NO: 57 | CAGAAGCCCTACAAGAAAATG | SEQ ID NO: 116 | | GTCACTCATAAGTGCATACATC |
| mouseNRP1 | SEQ ID NO: 58 | TTATCTTTCAGGGAAACACC | SEQ ID NO: 117 | | TCCAGAGCAAGGATAATCTG |
| mouseTEK | SEQ ID NO: 59 | ATTTCCGTCAAAGTTCTTCC | SEQ ID NO: 118 | | AAGCTTCTTGGATTTGATGG |

[1] PCR conditions: initial denaturation step at 94° C. for 5 min; 40 cycles of denaturation at 94° C. for 30 sec, annealing at 60° C. for 33 sec and extension at 72° C. for 30 sec. At the end was performed a final 7 minutes extension at 72° C. After amplification, melting curves were acquired and used to determine the specificity of PCR products, which were further confirmed using conventional gel electrophoresis.

TABLE 2

Genes represented in heat map FIG. 1-B

| Probe | NM pubmed | Symbol | Complete name |
|---|---|---|---|
| A_23_P210763 | NM_000214 | JAG1 | jagged 1 |
| A_23_P106024 | NM_002226 | JAG2 | jagged 2 |
| A_24_P365807 | NM_004429 | EFNB1 | ephrin-B1 |
| A_23_P428139 | NM_004093 | EFNB2 | ephrin-B2 |
| A_23_P60387 | NM_017617 | NOTCH1 | notch 1 |
| A_23_P200792 | NM_024408 | NOTCH2 | notch 2 |
| A_24_P399606 | NM_000435 | NOTCH3 | notch 3 |
| A_23_P365614 | NM_004557 | NOTCH4 | notch 4 |
| A_23_P167920 | NM_005618 | DLL1 | delta-like 1 (*Drosophila*) |
| A_23_P16438 | NM_016941 | DLL3 | delta-like 3 (*Drosophila*) |
| A_23_P419641 | NM_019074 | DLL4 | delta-like 4 (*Drosophila*) |
| A_23_P83098 | NM_000689 | ALDH1A1 | aldehyde dehydrogenase 1 family, member A1 |
| A_24_P363408 | NM_012259 | HEY2 | hairy/enhancer-of-split related with YRPW motif 2 |
| A_23_P78405 | NM_006033 | LIPG | lipase, endothelial |
| A_23_P24870 | NM_000610 | CD44 | CD44 molecule (Indian blood group) |
| A_23_P331098 | AK096419 | KRT78 | keratin 78 |
| A_23_P110531 | NM_013409 | FST | follistatin |

TABLE 3

Genes represented in heat map FIG. 1-H

| Probe | NM pubmed | Symbol | Complete name |
|---|---|---|---|
| A_23_P63371 | NM_003189 | TAL1 | T-cell acute lymphocytic leukemia 1 |
| A_23_P149064 | NM_005704 | PTPRU | protein tyrosine phosphatase, receptor type, U |
| A_23_P137381 | NM_002167 | ID3 | inhibitor of DNA binding 3, dominant negative helix-loop-helix protein |
| A_23_P252306 | NM_002165 | ID1 | inhibitor of DNA binding 1, dominant negative helix-loop-helix protein |
| A_23_P216023 | NM_001146 | ANGPT1 | angiopoietin 1 |
| A_23_P60079 | NM_001147 | ANGPT2 | angiopoietin 2 |
| A_23_P132378 | NM_014246 | CELSR1 | cadherin, EGF LAG seven-pass G-type receptor 1 (flamingo homolog, *Drosophila*) |
| A_23_P144627 | NM_018933 | PCDHB13 | protocadherin beta 13 |
| A_23_P38732 | NM_001792 | CDH2 | cadherin 2, type 1, N-cadherin (neuronal) |

TABLE 4

List of the 99 that induced differences in cell viability (hESC-Derived ECs versus ACL cells)

| Name | Class | Differences (%) |
|---|---|---|
| S-(p-Azidophenacyl)glutathione | Multi-Drug Resistance | 61.3 |
| AA-861 | Leukotriene | 53.3 |
| 5-azacytidine | DNA Metabolism | 56.1 |
| Brefeldin A from *Penicillium brefeldianum* | Cytoskeleton and ECM | 95.5 |

TABLE 4-continued

List of the 99 that induced differences in cell viability (hESC-Derived ECs versus ACL cells

| Name | Class | Differences (%) |
|---|---|---|
| Chlorprothixene hydrochloride | Dopamine | 58.1 |
| (±)-Butaclamol hydrochloride | Dopamine | 53.6 |
| BWB70C | Leukotriene | 55.3 |
| 5-Bromo-2'-deoxyuridine | DNA Metabolism | 53.9 |
| Bromoacetyl alprenolol menthane | Adrenoceptor | 93.4 |
| Cantharidin | Phosphorylation | 94.3 |
| Chlorpromazine hydrochloride | Dopamine | 57.2 |
| Calmidazolium chloride | Intracellular Calcium | 96.1 |
| 7-Chloro-4-hydroxy-2-phenyl-1,8-naphthyridine | Adenosine | 59.1 |
| Colchicine | Cytoskeleton and ECM | 67.4 |
| Calcimycin | Intracellular Calcium | 96.2 |
| Cantharidic Acid | Phosphorylation | 93.8 |
| Dequalinium dichloride | K+ Channel | 60.6 |
| (S)-(+)-Camptothecin | Apoptosis | 96.3 |
| 10-(alpha-Diethylaminopropionyl)-phenothiazine hydrochloride | Biochemistry | 56.8 |
| Dihydroouabain | Ion Pump | 97.0 |
| Diphenyleneiodonium chloride | Nitric Oxide | 69.6 |
| Dequalinium analog, C-14 linker | Phosphorylation | 96.6 |
| 3',4'-Dichlorobenzamil | Ion Pump | 54.2 |
| Etoposide | Apoptosis | 59.6 |
| DCEBIO | K+ Channel | 73.2 |
| Danazol | Hormone | 52.7 |
| 7-Cyclopentyl-5-(4-phenoxy)phenyl-7H-pyrrolo[2,3-d]pyrimidin-4-ylamine | Phosphorylation | 65.4 |
| Emetine dihydrochloride hydrate | Apoptosis | 93.4 |
| rac-2-Ethoxy-3-octadecanamido-1-propylphosphocholine | Phosphorylation | 56.2 |
| R-(−)-Fluoxetine hydrochloride | Serotonin | 54.5 |
| Felodipine | Ca2+ Channel | 58.1 |
| Ergocristine | Dopamine | 52.5 |
| Fluspirilene | Dopamine | 86.7 |
| Felbamate | Glutamate | 50.5 |
| Fiduxosin hydrochloride | Adrenoceptor | 58.2 |
| cis-(Z)-Flupenthixol dihydrochloride | Dopamine | 69.6 |
| Ellipticine | Cell Cycle | 58.5 |
| 5-fluoro-5'-deoxyuridine | DNA Metabolism | 60.8 |
| S-(+)-Fluoxetine hydrochloride | Serotonin | 51.4 |
| Fluphenazine dihydrochloride | Dopamine | 51.4 |
| Idarubicin | DNA Metabolism | 94.0 |
| Indirubin-3'-oxime | Phosphorylation | 85.5 |
| SB 228357 | Serotonin | 62.7 |
| LY-367,265 | Serotonin | 51.1 |
| NNC 55-0396 | Ca2+ Channel | 98.4 |
| Ivermectin | Cholinergic | 78.7 |
| Metergoline | Serotonin | 56.5 |
| Nocodazole | Cytoskeleton and ECM | 76.4 |
| 2-methoxyestradiol | Hormone | 84.3 |
| Mibefradil dihydrochloride | Ca2+ Channel | 62.2 |
| Mevastatin | Antibiotic | 98.0 |
| Mitoxantrone | DNA Metabolism | 94.4 |
| GR 127935 hydrochloride | Serotonin | 66.1 |
| Methiothepin mesylate | Serotonin | 52.4 |
| Niclosamide | Antibiotic | 97.6 |
| 1,3-Dimethyl-8-phenylxanthine | Adenosine | 68.8 |
| Podophyllotoxin | Cytoskeleton and ECM | 75.7 |
| Ouabain | Ion Pump | 94.6 |
| SU 6656 | Phosphorylation | 61.5 |
| Propionylpromazine hydrochloride | Dopamine | 50.3 |
| S(−)-3PPP hydrochloride | Dopamine | 51.8 |
| IC 261 | Phosphorylation | 73.0 |
| Rottlerin | Phosphorylation | 61.6 |
| N-Oleoyldopamine | Neurotransmission | 54.8 |
| Risperidone | Dopamine | 56.9 |
| SCH-202676 hydrobromide | G protein | 53.2 |
| SR 2640 | Leukotriene | 53.0 |
| SKF 96365 | Ca2+ Channel | 69.8 |
| Sanguinarine chloride | Ion Pump | 96.4 |
| Triflupromazine hydrochloride | Dopamine | 53.0 |
| Tyrphostin AG 537 | Phosphorylation | 52.3 |
| N-p-Tosyl-L-phenylalanine chloromethyl ketone | Biochemistry | 63.9 |
| Trequinsin hydrochloride | Cyclic Nucleotides | 50.7 |
| Tyrphostin AG 490 | Phosphorylation | 56.3 |
| SB 224289 hydrochloride | Serotonin | 96.7 |
| Tyrphostin AG 879 | Phosphorylation | 54.4 |

TABLE 4-continued

List of the 99 that induced differences in cell
viability (hESC-Derived ECs versus ACL cells

| Name | Class | Differences (%) |
|---|---|---|
| TTNPB | Transcription | 92.6 |
| Tyrphostin AG 527 | Phosphorylation | 53.4 |
| Taxol | Cytoskeleton and ECM | 78.1 |
| Tomoxetine | Adrenoceptor | 68.7 |
| Tamoxifen citrate | Phosphorylation | 98.3 |
| Telenzepine dihydrochloride | Cholinergic | 68.9 |
| Vincristine sulfate | Cytoskeleton and ECM | 89.2 |
| Terfenadine | Histamine | 98.3 |
| U-74389G maleate | Cell Stress | 51.6 |
| U0126 | Phosphorylation | 68.9 |
| U-83836 dihydrochloride | Cell Stress | 51.3 |
| Vinblastine sulfate salt | Cytoskeleton and ECM | 92.8 |
| Trifluoperazine dihydrochloride | Dopamine | 54.0 |
| R(+)-Terguride | Dopamine | 57.1 |
| (±)-Verapamil hydrochloride | Ca2+ Channel | 85.1 |
| XK469 | Apoptosis | 75.9 |
| S-5-Iodowillardiine | Glutamate | 52.8 |
| Wortmannin from Penicillium funiculosum | Phosphorylation | 57.9 |
| Thioridazine hydrochloride | Dopamine | 51.6 |
| Tyrphostin A9 | Phosphorylation | 69.5 |
| Zardaverine | Cyclic Nucleotides | 84.0 |
| Thapsigargin | Intracellular Calcium | 94.8 |
| (R)-(+)-WIN 55,212-2 mesylate | Cannabinoid | 97.7 |

TABLE 5

Genes represented in heat map FIG. 6-B

| Probe | NM pubmed | Symbol | Complete name |
|---|---|---|---|
| A_23_P10559 | NM_001080395 | AATK | apoptosis-associated tyrosine kinase |
| A_23_P60180 | NM_005157 | ABL1 | c-abl oncogene 1, non-receptor tyrosine kinase |
| A_23_P208389 | NM_021913 | AXL | AXL receptor tyrosine kinase |
| A_23_P253602 | NM_001721 | BMX | BMX non-receptor tyrosine kinase |
| A_23_P152024 | NM_004383 | CSK | c-src tyrosine kinase |
| A_23_P400716 | NM_001010846 | SHE | Src homology 2 domain containing E |
| A_23_P93311 | NM_013993 | DDR1 | discoidin domain receptor tyrosine kinase 1 |
| A_32_P88965 | BX537651 | DDR2 | discoidin domain receptor tyrosine kinase 2 |
| A_23_P5601 | NM_001381 | DOK1 | docking protein 1, 62 kDa (downstream of tyrosine kinase 1) |
| A_23_P124570 | NM_005246 | FER | fer (fps/fes related) tyrosine kinase |
| A_23_P502142 | NM_002037 | FYN | FYN oncogene related to SRC, FGR, YES |
| A_23_P48561 | NM_005864 | EFS | embryonal Fyn-associated substrate |
| A_24_P42755 | NM_002019 | FLT1 | fms-related tyrosine kinase 1 (vascular endothelial growth factor/vascular permeability factor receptor) |
| A_23_P213394 | NM_182925 | FLT4 | fms-related tyrosine kinase 4 |
| A_23_P61230 | NM_004712 | HGS | hepatocyte growth factor-regulated tyrosine kinase substrate |
| A_24_P929724 | NM_015525 | IBTK | inhibitor of Bruton agammaglobulinemia tyrosine kinase |
| A_23_P58419 | NM_002253 | KDR | kinase insert domain receptor (a type III receptor tyrosine kinase) |
| A_23_P376088 | NM_017806 | LIME1 | Lck interacting transmembrane adaptor 1 |
| A_23_P147431 | NM_002350 | LYN | v-yes-1 Yamaguchi sarcoma viral related oncogene homolog |
| A_23_P215275 | NM_014916 | LMTK2 | lemur tyrosine kinase 2 |
| A_23_P164918 | NM_001080434 | LMTK3 | lemur tyrosine kinase 3 |
| A_23_P14853 | NM_002344 | LTK | leukocyte receptor tyrosine kinase |
| A_23_P32955 | ENST00000421804 | MERTK | c-mer proto-oncogene tyrosine kinase |
| A_23_P86390 | NM_003873 | NRP1 | neuropilin 1 |
| A_23_P216779 | NM_001007097 | NTRK2 | neurotrophic tyrosine kinase, receptor, type 2 |
| A_24_P810476 | ENST00000394480 | NTRK3 | neurotrophic tyrosine kinase, receptor, type 3 |
| A_23_P22096 | NM_153831 | PTK2 | PTK2 protein tyrosine kinase 2 |
| A_23_P168836 | NM_173174 | PTK2B | PTK2B protein tyrosine kinase 2 beta |
| A_24_P320545 | NM_002821 | PTK7 | PTK7 protein tyrosine kinase 7 |
| A_23_P12363 | NM_005012 | ROR1 | receptor tyrosine kinase-like orphan receptor 1 |
| A_24_P229377 | NM_001005861 | RYK | RYK receptor-like tyrosine kinase |
| A_23_P374695 | NM_000459 | TEK | TEK tyrosine kinase, endothelial |
| A_23_P126416 | NM_005424 | TIE1 | tyrosine kinase with immunoglobulin-like and EGF-like domains 1 |
| A_23_P61633 | NM_005781 | TNK2 | tyrosine kinase, non-receptor, 2 |

TABLE 5-continued

Genes represented in heat map FIG. 6-B

| Probe | NM pubmed | Symbol | Complete name |
|---|---|---|---|
| A_23_P54517 | NM_006293 | TYRO3 | TYRO3 protein tyrosine kinase |
| A_23_P215790 | NM_005228 | EGFR | epidermal growth factor receptor |
| A_23_P208369 | NM_025194 | ITPKC | inositol-trisphosphate 3-kinase C |
| A_23_P39682 | NM_001079 | ZAP70 | zeta-chain (TCR) associated protein kinase 70 kDa |

The present invention is not, in any way, restricted to the embodiments described herein and a person of ordinary skills in the area can provide many possibilities to modifications thereof without departing from the general idea of the invention, as defined in the claims.

The preferred embodiments described above are obviously combinable. The following claims define further preferred embodiments of the present invention.

REFERENCES

1. Ferreira, L. S. et al. Vascular progenitor cells isolated from human embryonic stem cells give rise to endothelial and smooth muscle like cells and form vascular networks in vivo. Circulation Research 101, 286-294 (2007).
2. Vazao, H., das Neves, R. P., Grãos, M. & Ferreira, L. Towards the maturation and characterization of smooth muscle cells derived from human embryonic stem cells. PLOS one 6, e17771 (2011).
3. Levenberg, S., Golub, J. S., Amit, M., Itskovitz-Eldor, J. & Langer, R. Endothelial cells derived from human embryonic stem cells. Proc Natl Acad Sci USA 99, 4391-4396 (2002).
4. Wang, L. et al. Endothelial and Hematopoietic Cell Fate of Human Embryonic Stem Cells Originates from Primitive Endothelium with Hemangioblastic Properties. Immunity 21, 31-41 (2004).
5. Li, Z. et al. Functional and transcriptional characterization of human embryonic stem cell-derived endothelial cells for treatment of myocardial infarction. PLoS ONE 4, e8443 (2009).
6. Cho, S.-W. et al. Improvement of postnatal neovascularization by human embryonic stem cell derived endothelial-like cell transplantation in a mouse model of hindlimb ischemia. Circulation 116, 2409-2419 (2007).
7. Lu, S.-J. et al. Generation of functional hemangioblasts from human embryonic stem cells. Nat Methods 4, 501-509 (2007).
8. Sone, M. et al. Pathway for differentiation of human embryonic stem cells to vascular cell components and their potential for vascular regeneration. Arteriosclerosis, Thrombosis, and Vascular Biology 27, 2127-2134 (2007).
9. Wang, Z. Z. et al. Endothelial cells derived from human embryonic stem cells form durable blood vessels in vivo. Nat Biotechnol 25, 317-318 (2007).
10. Vodyanik, M. A., Thomson, J. A. & Slukvin, I. I. Leukosialin (CD43) defines hematopoietic progenitors in human embryonic stem cell differentiation cultures. Blood 108, 2095-2105 (2006).
11. Kume, T. Specification of arterial, venous, and lymphatic endothelial cells during embryonic development. Histol Histopathol 25, 637-646 (2010).
12. Swift, M. R. & Weinstein, B. M. Arterial-venous specification during development. Circulation Research 104, 576-588 (2009).
13. Wang, H., Chen, Z. & Anderson, D. Molecular distinction and angiogenic interaction between embryonic arteries and veins revealed by ephrin-B2 and its receptor Eph-B4. Cell 93, 741-753 (1998).
14. Fiddes, L. K. et al. A circular cross-section PDMS microfluidics system for replication of cardiovascular flow conditions. Biomaterials 31, 3459-3464 (2010).
15. Lee, S. H., Kang do, H., Kim, H. N. & Suh, K. Y. Use of directly molded poly(methyl methacrylate) channels for microfluidic applications. Lab Chip 10, 3300-3306 (2010).
16. Tsai, M. et al. In vitro modeling of the microvascular occlusion and thrombosis that occur in hematologic diseases using microfluidic technology. J Clin Invest 122, 408-418 (2012).
17. Nourse, M. B. et al. VEGF Induces Differentiation of Functional Endothelium From Human Embryonic Stem Cells: Implications for Tissue Engineering. Arterioscler Thromb Vasc Biol 30, 80-89 (2010).
18. Kraehenbuehl, T. P. et al. Human embryonic stem cell-derived microvascular grafts for cardiac tissue preservation after myocardial infarction. Biomaterials 32, 1102-1109 (2011).
19. Smart, N. et al. Thymosin beta4 induces adult epicardial progenitor mobilization and neovascularization. Nature 445, 177-182 (2007).
20. James, D. et al. Expansion and maintenance of human embryonic stem cell-derived endothelial cells by TGFbeta inhibition is Id1 dependent. Nat Biotechnol 28, 161-166 (2010).
21. Breiteneder-Geleff, S. et al. Angiosarcomas express mixed endothelial phenotypes of blood and lymphatic capillaries: podoplanin as a specific marker for lymphatic endothelium. Am J Pathol 154, 385-394 (1999).
22. Chi, J.-T. et al. Endothelial cell diversity revealed by global expression profiling. Proc Natl Acad Sci USA 100, 10623-10628 (2003).
23. Haase, A. et al. Generation of induced pluripotent stem cells from human cord blood. Cell Stem Cell 5, 434-441 (2009).
24. Koop, E. A. et al. Receptor protein tyrosine phosphatase mu expression as a marker for endothelial cell heterogeneity; analysis of RPTPmu gene expression using LacZ knock-in mice. Int J Dev Biol 47, 345-354 (2003).
25. Kubo, H. & Alitalo, K. The bloody fate of endothelial stem cells. Genes Dev 17, 322-329 (2003).
26. Gentile, C., Muise-Helmericks, R. C. & Drake, C. J. VEGF-mediated phosphorylation of eNOS regulates angioblast and embryonic endothelial cell proliferation. Developmental Biology 373, 163-175 (2013).
27. Levine, E., Lee, C. H., Kintner, C. & Gumbiner, B. M. Selective disruption of E-cadherin function in early Xenopus embryos by a dominant negative mutant. Development 120, 901-909 (1994).

28. Kadokawa Yuzo, Fuketa Izumi, Nose Akinao, Takeichi Masatoshi & Nakatsuji, N. Expression Pattern of E- and P-Cadherin in Mouse Embryos and Uteri during the Periimplantation Period. Develop. Growth & Differ. 31 23-30 (1989).
29. Malek, A. M., Alper, S. L. & Izumo, S. Hemodynamic shear stress and its role in atherosclerosis. JAMA 282, 2035-2042 (1999).
30. Tzima, E. et al. A mechanosensory complex that mediates the endothelial cell response to fluid shear stress. Nature 437, 426-431 (2005).
31. Florian, J. A. et al. Heparan sulfate proteoglycan is a mechanosensor on endothelial cells. Circulation Research 93, e136-142 (2003).
32. Thi, M. M., Tarbell, J. M., Weinbaum, S. & Spray, D. C. The role of the glycocalyx in reorganization of the actin cytoskeleton under fluid shear stress: a "bumper-car" model. Proc Natl Acad Sci USA 101, 16483-16488 (2004).
33. Potter, D. R. & Damiano, E. R. The hydrodynamically relevant endothelial cell glycocalyx observed in vivo is absent in vitro. Circulation Research 102, 770-776 (2008).
34. Ho, P., Zhong, W. & Lee, W. Terbinafine inhibits endothelial cell migration through suppression of the Rho-mediated pathway. Molecular cancer therapeutics 12, 3130-3138 (2006).
35. Ho, P. Y., Liang, Y. C., Ho, Y. S., Chen, C. T. & Lee, W. S. Inhibition of human vascular endothelial cells proliferation by terbinafine. Int J Cancer 111, 51-59 (2004).
36. Gaucher, C. et al. In vitro impact of physiological shear stress on endothelial cells gene expression profile. Clin Hemorheol Microcirc 37, 99-107 (2007).
37. Pullamsetti, S. et al. Increased levels and reduced catabolism of asymmetric and symmetric dimethylarginines in pulmonary hypertension. FASEB J 19, 1175-1177 (2005).
38. Boger, R. H., Cooke, J. P. & Vallance, P. ADMA: an emerging cardiovascular risk factor. Vasc Med 10 Suppl 1, S1-2 (2005).
39. Louden, C. et al. Biomarkers and mechanisms of drug-induced vascular injury in non-rodents. Toxicologic Pathology 34, 19-26 (2006).
40. Tesfamariam, B. & DeFelice, A. F. Endothelial injury in the initiation and progression of vascular disorders. Vascul Pharmacol 46, 229-237 (2007).
41. D'Amato, R. J., Loughnan, M. S., Flynn, E. & Folkman, J. Thalidomide is an inhibitor of angiogenesis. Proc Natl Acad Sci USA 91, 4082-4085 (1994).
42. Kleinstreuer, N. C. et al. Environmental impact on vascular development predicted by high-throughput screening. Environ Health Perspect 119, 1596-1603 (2011).
43. Tideman, E., Marsal, K. & Ley, D. Cognitive function in young adults following intrauterine growth restriction with abnormal fetal aortic blood flow. Ultrasound Obstet Gynecol 29, 614-618 (2007).
44. Hoyme, H. E. et al. Prenatal cocaine exposure and fetal vascular disruption. Pediatrics 85, 743-747 (1990).
45. Hirst, G. et al. Kinase inhibitors as therapeutic agents. U.S. Pat. No. 7,071,199B1. (2006).
46. Arnold, L. D. et al. Pyrrolo[2,3-d]pyrimidines containing an extended 5-substituent as potent and selective inhibitors of Ick I. Bioorg Med Chem Lett 10, 2167-2170 (2000).
47. Aranguren, X. L. et al. In vitro and in vivo arterial differentiation of human multipotent adult progenitor cells. Blood 109, 2634-2642 (2007).
48. Lamont, R. E. & Childs, S. MAPping out arteries and veins. Science's STKE 2006, pe39 (2006).
49. Nikmanesh, M., Shi, Z. D. & Tarbell, J. M. Heparan sulfate proteoglycan mediates shear stress-induced endothelial gene expression in mouse embryonic stem cell-derived endothelial cells. Biotechnol Bioeng 109, 583-594 (2012).
50. Lee, W.-S. et al. In vitro and in vivo studies of the anticancer action of terbinafine in human cancer cell lines: G0/G1 p53-associated cell cycle arrest. Int J Cancer 106, 125-137 (2003).
51. Kalin, R. E., Banziger-Tobler, N. E., Detmar, M. & Brandli, A. W. An in vivo chemical library screen in Xenopus tadpoles reveals novel pathways involved in angiogenesis and lymphangiogenesis. Blood 114, 1110-1122 (2009).
52. Schulz, M. M. P. et al. Phenotype-based high-content chemical library screening identifies statins as inhibitors of in vivo lymphangiogenesis. Proc Natl Acad Sci USA 109, E2665-2674 (2012).
53. Agasse, F. et al. Neuropeptide Y promotes neurogenesis in murine subventricular zone. Stem Cells 26, 1636-1645 (2008).
54. Bernardino, L. et al. Tumor necrosis factor-alpha modulates survival, proliferation, and neuronal differentiation in neonatal subventricular zone cell cultures. Stem Cells 26, 2361-2371 (2008).
55. Olsson, A.-K., Dimberg, A., Kreuger, J. & Claesson-Welsh, L. VEGF receptor signalling—in control of vascular function. Nat Rev Mol Cell Biol 7, 359-371 (2006).
56. Maia, J. et al. VEGF-Functionalized Dextran Has Longer Intracellular Bioactivity than VEGF in Endothelial Cells. Biomacromolecules 13, 2906-2916 (2012).
57. Persson, B. et al. Endotoxin Induces Differentiated Contractile Responses in Porcine Pulmonary Arteries and Veins. Journal of Vascular Research 48, 206-211 (2010).
58. Gao, Y., Zhou, H., Ibe, B. O. & Raj, J. U. Prostaglandins E2 and I2 cause greater relaxations in pulmonary veins than in arteries of newborn lambs. J Appl Physiol 81, 2534-2539 (1996).
59. Furchgott, R. Endothelium-derived relaxing factor: discovery, early studies, and identification as nitric oxide. Bioscience reports (1999).
60. Grynkiewicz, G., Poenie, M. & Tsien, R. Y. A new generation of Ca2+ indicators with greatly improved fluorescence properties. J Biol Chem 260, 3440-3450 (1985).
61. O'connor, M. D. et al. Alkaline phosphatase-positive colony formation is a sensitive, specific, and quantitative indicator of undifferentiated human embryonic stem cells. Stem Cells 26, 1109-1116 (2008).

The invention claimed is:

1. A method for screening compounds that interfere with embryonic vascular development or has fetal cytotoxic effect, said method comprising:
providing a channel having a millimeter or micrometer dimension;
populating the channel with differentiated endothelial cells derived from human pluripotent stem cells, wherein a portion of the differentiated endothelial cells express ephrin B2;
culturing the differentiated endothelial cells under physiologic shear stress to produce a quantity of differentiated endothelial cells sufficient for screening compounds for interference with embryonic vascular development or fetal cytotoxic effect;
culturing human umbilical arterial endothelial cells (HUAECs) under static conditions;
exposing the differentiated endothelial cells and the HUAECs to a selected compound, wherein the differentiated endothelial cells and the HUAECs were exposed to the selected compound via a medium supplemented with the compound;
analyzing levels of inflammatory genes in the differentiated endothelial cells and the HUAECs after exposure to the selected compound; and
comparing the levels of inflammatory genes of the differentiated endothelial cells with those of the HUAECs,
wherein the inflammatory genes comprise ICAM-1, E-selectin, HO-1 and eNOS, and
wherein if the differentiated endothelial cells exposed to the selected compound express statistically significantly higher levels of the inflammatory genes relative to the HUAECs, then that is a first indication that the selected compound interferes with embryonic vascular development or has fetal cytotoxic effect.

2. The method of claim 1, wherein at least 20% of the differentiated endothelial cells express ephrin B2.

3. The method of claim 1, wherein 50% to 75% of the differentiated endothelial cells express ephrin B2.

4. The method of claim 1, wherein the differentiated endothelial cells further express acetylated-low density lipoprotein (Ac-LDL).

5. The method of claim 1, wherein the differentiated endothelial cells further express at least one of the following genes: Von Willebrand factor (vWF), CD31, CD34, vascular endothelial cadherin, and Flk-1/KDR.

6. The method of claim 1, wherein the differentiated endothelial cells express at least one the following genes: jagged 1, jagged 2, ephrin B1, and Hey-2.

7. The method of claim 1, wherein the differentiated endothelial cells express at least one of the following genes: receptor protein tyrosine phosphatase, T-cell acute lymphocyte leukemia, N-cadherin, angiopoietin 1, and DNA-binding protein inhibitor ID-1.

8. The method of claim 1, wherein the differentiated endothelial cells cultured under physiologic shear stress are cells seeded and exposed to a media flow.

9. The method of claim 1, wherein the differentiated endothelial cells produce glycocalyx.

10. The method of claim 4, wherein the channel comprises poly (dimethylsiloxane).

11. The method of claim 1, wherein the channel is coated with gelatin, collagen, fibronectin, fibrin, matrigel or combination thereof.

12. The method of claim 1, wherein the selected compound is selected from the group consisting of: danazol, chlorpromazine hydrochloride, ellipticine, 3'4'-dichlorobenzamil, fluphenzine dihydrochloride, and 7-cyclopentyl-5-(4-phenoxy) phenyl-7H-pyrrolo[2,3-d]pyrimidin-4-ylamine.

13. The method of claim 1, wherein culturing under physiologic shear stress comprises culturing cells for 7 days in an arterial flow at 20 dyne/cm$^2$.

14. The method of claim 1, wherein the differentiated endothelial cells and the HUAECs were exposed to 1 μm of the selected compound in the medium for 24 hours.

15. The method of claim 1, further comprising:
analyzing levels of DDAH1 and DDAH2 in the differentiated endothelial cells and the HUAECs after exposure to the selected compound; and
comparing the levels of DDAH1 and DDAH2 in the differentiated endothelial cells with those of the HUAECs, where if the differentiated endothelial cells exposed to the selected compound express statistically significantly lower levels of the DDAH1 and DDAH2 relative to the HUAECs, that is a second indication that the selected compound interferes with embryonic vascular development or has fetal cytotoxic effect.

16. The method of claim 1, wherein at least a portion of the differentiated endothelial cells express the following genes: DLL1, LYN, TEK, DNA-binding protein inhibitor ID-1, FLT1.

* * * * *

SEQUENCE LISTING

<160> NUMBER OF SEQ ID NOS: 118

<210> SEQ ID NO 1

```
<211> LENGTH: 20
<212> TYPE: DNA
<213> ORGANISM: Homo sapiens

<400> SEQUENCE: 1
agccacatcg ctcagacacc                                                  20

<210> SEQ ID NO 2
<211> LENGTH: 20
<212> TYPE: DNA
<213> ORGANISM: Homo sapiens

<400> SEQUENCE: 2
gctgttggtg gaaggagtgc                                                  20

<210> SEQ ID NO 3
<211> LENGTH: 20
<212> TYPE: DNA
<213> ORGANISM: Homo sapiens

<400> SEQUENCE: 3
tgaagcctag cctgtcacct                                                  20

<210> SEQ ID NO 4
<211> LENGTH: 20
<212> TYPE: DNA
<213> ORGANISM: Homo sapiens

<400> SEQUENCE: 4
acgggatgac caagtacagc                                                  20

<210> SEQ ID NO 5
<211> LENGTH: 20
<212> TYPE: DNA
<213> ORGANISM: Homo sapiens

<400> SEQUENCE: 5
atgttgtggg agatgtttgc                                                  20

<210> SEQ ID NO 6
<211> LENGTH: 23
<212> TYPE: DNA
<213> ORGANISM: Homo sapiens

<400> SEQUENCE: 6
ctggcatggt cttctgtgaa gca                                              23

<210> SEQ ID NO 7
<211> LENGTH: 20
<212> TYPE: DNA
<213> ORGANISM: Homo sapiens

<400> SEQUENCE: 7
gtggaggaag ctgacaacaa                                                  20

<210> SEQ ID NO 8
<211> LENGTH: 18
<212> TYPE: DNA
<213> ORGANISM: Homo sapiens

<400> SEQUENCE: 8
ctcagttcgg atcctacc                                                    18
```

<210> SEQ ID NO 9
<211> LENGTH: 20
<212> TYPE: DNA
<213> ORGANISM: Homo sapiens

<400> SEQUENCE: 9
ctgacaagtt acctcaccta                                              20

<210> SEQ ID NO 10
<211> LENGTH: 23
<212> TYPE: DNA
<213> ORGANISM: Homo sapiens

<400> SEQUENCE: 10
gaactgaatt gctgtgttat atg                                          23

<210> SEQ ID NO 11
<211> LENGTH: 23
<212> TYPE: DNA
<213> ORGANISM: Homo sapiens

<400> SEQUENCE: 11
atctgaaata ggaaacaagt gaa                                          23

<210> SEQ ID NO 12
<211> LENGTH: 20
<212> TYPE: DNA
<213> ORGANISM: Homo sapiens

<400> SEQUENCE: 12
aacatctcat ccatgctttg                                              20

<210> SEQ ID NO 13
<211> LENGTH: 18
<212> TYPE: DNA
<213> ORGANISM: Homo sapiens

<400> SEQUENCE: 13
cgctcgtcag ttcttaga                                                18

<210> SEQ ID NO 14
<211> LENGTH: 18
<212> TYPE: DNA
<213> ORGANISM: Homo sapiens

<400> SEQUENCE: 14
attgacaccc agcttctt                                                18

<210> SEQ ID NO 15
<211> LENGTH: 19
<212> TYPE: DNA
<213> ORGANISM: Homo sapiens

<400> SEQUENCE: 15
tgtccgtgaa atgaattgg                                               19

<210> SEQ ID NO 16
<211> LENGTH: 18
<212> TYPE: DNA
<213> ORGANISM: Homo sapiens

<400> SEQUENCE: 16
ggaggtataa ggcaggag                                                18

-continued

```
<210> SEQ ID NO 17
<211> LENGTH: 19
<212> TYPE: DNA
<213> ORGANISM: Homo sapiens

<400> SEQUENCE: 17
gtctcaaaga agcgatcag                                              19

<210> SEQ ID NO 18
<211> LENGTH: 21
<212> TYPE: DNA
<213> ORGANISM: Homo sapiens

<400> SEQUENCE: 18
acaatggagt attctcggat a                                           21

<210> SEQ ID NO 19
<211> LENGTH: 18
<212> TYPE: DNA
<213> ORGANISM: Homo sapiens

<400> SEQUENCE: 19
caacactgtc aagatggc                                               18

<210> SEQ ID NO 20
<211> LENGTH: 21
<212> TYPE: DNA
<213> ORGANISM: Homo sapiens

<400> SEQUENCE: 20
ccacagatag gagacaaatt g                                           21

<210> SEQ ID NO 21
<211> LENGTH: 21
<212> TYPE: DNA
<213> ORGANISM: Homo sapiens

<400> SEQUENCE: 21
gagtttgttc atccaatcgt a                                           21

<210> SEQ ID NO 22
<211> LENGTH: 18
<212> TYPE: DNA
<213> ORGANISM: Homo sapiens

<400> SEQUENCE: 22
acaacttcag aagtgcct                                               18

<210> SEQ ID NO 23
<211> LENGTH: 20
<212> TYPE: DNA
<213> ORGANISM: Homo sapiens

<400> SEQUENCE: 23
caaggcctca gtcagtgtga                                             20

<210> SEQ ID NO 24
<211> LENGTH: 20
<212> TYPE: DNA
<213> ORGANISM: Homo sapiens

<400> SEQUENCE: 24
agcttcccat ggaacacaac                                             20
```

<210> SEQ ID NO 25
<211> LENGTH: 26
<212> TYPE: DNA
<213> ORGANISM: Homo sapiens

<400> SEQUENCE: 25
gatgctccca acttgacctt gaccat                                26

<210> SEQ ID NO 26
<211> LENGTH: 20
<212> TYPE: DNA
<213> ORGANISM: Homo sapiens

<400> SEQUENCE: 26
gaaaagcaca tccaggcaat                                       20

<210> SEQ ID NO 27
<211> LENGTH: 20
<212> TYPE: DNA
<213> ORGANISM: Homo sapiens

<400> SEQUENCE: 27
ggacaaatca acgaggtgct                                       20

<210> SEQ ID NO 28
<211> LENGTH: 19
<212> TYPE: DNA
<213> ORGANISM: Homo sapiens

<400> SEQUENCE: 28
ctgttgtggc aggcagcag                                        19

<210> SEQ ID NO 29
<211> LENGTH: 20
<212> TYPE: DNA
<213> ORGANISM: Homo sapiens

<400> SEQUENCE: 29
atggagatta ctgatggtcc                                       20

<210> SEQ ID NO 30
<211> LENGTH: 20
<212> TYPE: DNA
<213> ORGANISM: Homo sapiens

<400> SEQUENCE: 30
acatagatgg ttaccacagg                                       20

<210> SEQ ID NO 31
<211> LENGTH: 20
<212> TYPE: DNA
<213> ORGANISM: Homo sapiens

<400> SEQUENCE: 31
acatatgtga tgaccgtaac                                       20

<210> SEQ ID NO 32
<211> LENGTH: 20
<212> TYPE: DNA
<213> ORGANISM: Homo sapiens

<400> SEQUENCE: 32
atgttaacag gaggatggtg                                          20

<210> SEQ ID NO 33
<211> LENGTH: 21
<212> TYPE: DNA
<213> ORGANISM: Homo sapiens

<400> SEQUENCE: 33
actagtcacc agagacttta g                                        21

<210> SEQ ID NO 34
<211> LENGTH: 20
<212> TYPE: DNA
<213> ORGANISM: Homo sapiens

<400> SEQUENCE: 34
acctcatcta caaaatcccc                                          20

<210> SEQ ID NO 35
<211> LENGTH: 21
<212> TYPE: DNA
<213> ORGANISM: Homo sapiens

<400> SEQUENCE: 35
gtacatagtt gtcgttgtag g                                        21

<210> SEQ ID NO 36
<211> LENGTH: 22
<212> TYPE: DNA
<213> ORGANISM: Homo sapiens

<400> SEQUENCE: 36
caacacctta gaaacagaag ag                                       22

<210> SEQ ID NO 37
<211> LENGTH: 21
<212> TYPE: DNA
<213> ORGANISM: Homo sapiens

<400> SEQUENCE: 37
atgggagtct agtggatttt c                                        21

<210> SEQ ID NO 38
<211> LENGTH: 20
<212> TYPE: DNA
<213> ORGANISM: Homo sapiens

<400> SEQUENCE: 38
tcttaaagac catccaggag                                          20

<210> SEQ ID NO 39
<211> LENGTH: 19
<212> TYPE: DNA
<213> ORGANISM: Homo sapiens

<400> SEQUENCE: 39
ctggatctac aagtgggag                                           19

<210> SEQ ID NO 40
<211> LENGTH: 20
<212> TYPE: DNA
<213> ORGANISM: Homo sapiens

<400> SEQUENCE: 40
agaagattgt gcaaaaccag    20

<210> SEQ ID NO 41
<211> LENGTH: 21
<212> TYPE: DNA
<213> ORGANISM: Homo sapiens

<400> SEQUENCE: 41
gtgattgaca ctggacataa c    21

<210> SEQ ID NO 42
<211> LENGTH: 21
<212> TYPE: DNA
<213> ORGANISM: Homo sapiens

<400> SEQUENCE: 42
cagtctacaa cttttcagct c    21

<210> SEQ ID NO 43
<211> LENGTH: 20
<212> TYPE: DNA
<213> ORGANISM: Homo sapiens

<400> SEQUENCE: 43
catgaaatgt cttcccagtg    20

<210> SEQ ID NO 44
<211> LENGTH: 20
<212> TYPE: DNA
<213> ORGANISM: Homo sapiens

<400> SEQUENCE: 44
aaagctgcag gtatttgatg    20

<210> SEQ ID NO 45
<211> LENGTH: 21
<212> TYPE: DNA
<213> ORGANISM: Homo sapiens

<400> SEQUENCE: 45
catgaagaac tttcagaagg g    21

<210> SEQ ID NO 46
<211> LENGTH: 21
<212> TYPE: DNA
<213> ORGANISM: Homo sapiens

<400> SEQUENCE: 46
gactcccatc ttcattaact c    21

<210> SEQ ID NO 47
<211> LENGTH: 21
<212> TYPE: DNA
<213> ORGANISM: Homo sapiens

<400> SEQUENCE: 47
agatggagat ttctgatggt c    21

<210> SEQ ID NO 48
<211> LENGTH: 21
<212> TYPE: DNA
<213> ORGANISM: Homo sapiens

```
<400> SEQUENCE: 48
ggacatgatc tttctcaagt g                                              21

<210> SEQ ID NO 49
<211> LENGTH: 21
<212> TYPE: DNA
<213> ORGANISM: Homo sapiens

<400> SEQUENCE: 49
gagtttactg ccatgacttt c                                              21

<210> SEQ ID NO 50
<211> LENGTH: 21
<212> TYPE: DNA
<213> ORGANISM: Homo sapiens

<400> SEQUENCE: 50
ctggaaggag tataaaatgg g                                              21

<210> SEQ ID NO 51
<211> LENGTH: 20
<212> TYPE: DNA
<213> ORGANISM: Homo sapiens

<400> SEQUENCE: 51
atctctggga aagacactac                                                20

<210> SEQ ID NO 52
<211> LENGTH: 20
<212> TYPE: DNA
<213> ORGANISM: Homo sapiens

<400> SEQUENCE: 52
ggaatatgac tacgtgcatc                                                20

<210> SEQ ID NO 53
<211> LENGTH: 22
<212> TYPE: DNA
<213> ORGANISM: Homo sapiens

<400> SEQUENCE: 53
gacggatgat caagagaaat ag                                             22

<210> SEQ ID NO 54
<211> LENGTH: 20
<212> TYPE: DNA
<213> ORGANISM: Homo sapiens

<400> SEQUENCE: 54
gaagccatgg gataaagatg                                                20

<210> SEQ ID NO 55
<211> LENGTH: 20
<212> TYPE: DNA
<213> ORGANISM: Homo sapiens

<400> SEQUENCE: 55
gtgaagagtc tgaaacaagg                                                20

<210> SEQ ID NO 56
<211> LENGTH: 20
<212> TYPE: DNA
<213> ORGANISM: Homo sapiens
```

```
<400> SEQUENCE: 56
ctgtcgcaaa gtttgtaatg                                              20

<210> SEQ ID NO 57
<211> LENGTH: 21
<212> TYPE: DNA
<213> ORGANISM: Homo sapiens

<400> SEQUENCE: 57
cagaagccct acaagaaaat g                                            21

<210> SEQ ID NO 58
<211> LENGTH: 20
<212> TYPE: DNA
<213> ORGANISM: Homo sapiens

<400> SEQUENCE: 58
ttatctttca gggaaacacc                                              20

<210> SEQ ID NO 59
<211> LENGTH: 20
<212> TYPE: DNA
<213> ORGANISM: Homo sapiens

<400> SEQUENCE: 59
atttccgtca aagttcttcc                                              20

<210> SEQ ID NO 60
<211> LENGTH: 19
<212> TYPE: DNA
<213> ORGANISM: Homo sapiens

<400> SEQUENCE: 60
gtactcagcg ccagcatcg                                               19

<210> SEQ ID NO 61
<211> LENGTH: 20
<212> TYPE: DNA
<213> ORGANISM: Homo sapiens

<400> SEQUENCE: 61
gaagttggct ggaggtgctc                                              20

<210> SEQ ID NO 62
<211> LENGTH: 20
<212> TYPE: DNA
<213> ORGANISM: Homo sapiens

<400> SEQUENCE: 62
cgcacagctg gaggtcttat                                              20

<210> SEQ ID NO 63
<211> LENGTH: 20
<212> TYPE: DNA
<213> ORGANISM: Homo sapiens

<400> SEQUENCE: 63
acacactttg ggctggtagg                                              20

<210> SEQ ID NO 64
<211> LENGTH: 20
<212> TYPE: DNA
```

<213> ORGANISM: Homo sapiens

<400> SEQUENCE: 64
gcagataaga gctcagcctt                                           20

<210> SEQ ID NO 65
<211> LENGTH: 23
<212> TYPE: DNA
<213> ORGANISM: Homo sapiens

<400> SEQUENCE: 65
aataccagtg gatgtgatgg cgg                                       23

<210> SEQ ID NO 66
<211> LENGTH: 20
<212> TYPE: DNA
<213> ORGANISM: Homo sapiens

<400> SEQUENCE: 66
ctccaggttg cctctcactc                                           20

<210> SEQ ID NO 67
<211> LENGTH: 19
<212> TYPE: DNA
<213> ORGANISM: Homo sapiens

<400> SEQUENCE: 67
aatgtcaccc acttcagat                                            19

<210> SEQ ID NO 68
<211> LENGTH: 18
<212> TYPE: DNA
<213> ORGANISM: Homo sapiens

<400> SEQUENCE: 68
gacacattgg gctttctg                                             18

<210> SEQ ID NO 69
<211> LENGTH: 19
<212> TYPE: DNA
<213> ORGANISM: Homo sapiens

<400> SEQUENCE: 69
aaccagaatc caggtatcc                                            19

<210> SEQ ID NO 70
<211> LENGTH: 23
<212> TYPE: DNA
<213> ORGANISM: Homo sapiens

<400> SEQUENCE: 70
ataaccaacg aacaactaca taa                                       23

<210> SEQ ID NO 71
<211> LENGTH: 19
<212> TYPE: DNA
<213> ORGANISM: Homo sapiens

<400> SEQUENCE: 71
acagtggtac aggtacttc                                            19

<210> SEQ ID NO 72
<211> LENGTH: 19

<212> TYPE: DNA
<213> ORGANISM: Homo sapiens

<400> SEQUENCE: 72
aaggaaggaa gagacagag                                                19

<210> SEQ ID NO 73
<211> LENGTH: 18
<212> TYPE: DNA
<213> ORGANISM: Homo sapiens

<400> SEQUENCE: 73
gaggacaagg gtcttcaa                                                 18

<210> SEQ ID NO 74
<211> LENGTH: 19
<212> TYPE: DNA
<213> ORGANISM: Homo sapiens

<400> SEQUENCE: 74
aagagaagat ggcaggtag                                                19

<210> SEQ ID NO 75
<211> LENGTH: 18
<212> TYPE: DNA
<213> ORGANISM: Homo sapiens

<400> SEQUENCE: 75
aggtgtggaa gggtattg                                                 18

<210> SEQ ID NO 76
<211> LENGTH: 18
<212> TYPE: DNA
<213> ORGANISM: Homo sapiens

<400> SEQUENCE: 76
atatactccg ccgattgg                                                 18

<210> SEQ ID NO 77
<211> LENGTH: 18
<212> TYPE: DNA
<213> ORGANISM: Homo sapiens

<400> SEQUENCE: 77
ctggtaacaa acgctacg                                                 18

<210> SEQ ID NO 78
<211> LENGTH: 19
<212> TYPE: DNA
<213> ORGANISM: Homo sapiens

<400> SEQUENCE: 78
ctcttctctt cctggttca                                                19

<210> SEQ ID NO 79
<211> LENGTH: 18
<212> TYPE: DNA
<213> ORGANISM: Homo sapiens

<400> SEQUENCE: 79
agttgaggag agggtat                                                  18

<210> SEQ ID NO 80

```
<211> LENGTH: 19
<212> TYPE: DNA
<213> ORGANISM: Homo sapiens

<400> SEQUENCE: 80
ggtgagtagg acaggtaag                                                19

<210> SEQ ID NO 81
<211> LENGTH: 18
<212> TYPE: DNA
<213> ORGANISM: Homo sapiens

<400> SEQUENCE: 81
gacaagagag aggtggag                                                 18

<210> SEQ ID NO 82
<211> LENGTH: 20
<212> TYPE: DNA
<213> ORGANISM: Homo sapiens

<400> SEQUENCE: 82
cctctggctt cgtcagaatc                                               20

<210> SEQ ID NO 83
<211> LENGTH: 20
<212> TYPE: DNA
<213> ORGANISM: Homo sapiens

<400> SEQUENCE: 83
ctgggctccc attagttcaa                                               20

<210> SEQ ID NO 84
<211> LENGTH: 20
<212> TYPE: DNA
<213> ORGANISM: Homo sapiens

<400> SEQUENCE: 84
taggtcttgg ggttgtcagg                                               20

<210> SEQ ID NO 85
<211> LENGTH: 20
<212> TYPE: DNA
<213> ORGANISM: Homo sapiens

<400> SEQUENCE: 85
gctgccacat tagggtgtct                                               20

<210> SEQ ID NO 86
<211> LENGTH: 20
<212> TYPE: DNA
<213> ORGANISM: Homo sapiens

<400> SEQUENCE: 86
tagcggtggt cactcatctg                                               20

<210> SEQ ID NO 87
<211> LENGTH: 20
<212> TYPE: DNA
<213> ORGANISM: Homo sapiens

<400> SEQUENCE: 87
gtcagggagg catatgggtg                                               20
```

```
<210> SEQ ID NO 88
<211> LENGTH: 20
<212> TYPE: DNA
<213> ORGANISM: Homo sapiens

<400> SEQUENCE: 88
aggatctcat tcttgctgag                                               20

<210> SEQ ID NO 89
<211> LENGTH: 21
<212> TYPE: DNA
<213> ORGANISM: Homo sapiens

<400> SEQUENCE: 89
agaagtcata gaccatctca g                                             21

<210> SEQ ID NO 90
<211> LENGTH: 20
<212> TYPE: DNA
<213> ORGANISM: Homo sapiens

<400> SEQUENCE: 90
tttttctcga tcaagtccag                                               20

<210> SEQ ID NO 91
<211> LENGTH: 20
<212> TYPE: DNA
<213> ORGANISM: Homo sapiens

<400> SEQUENCE: 91
gaagtagtgc cactttatcc                                               20

<210> SEQ ID NO 92
<211> LENGTH: 20
<212> TYPE: DNA
<213> ORGANISM: Homo sapiens

<400> SEQUENCE: 92
aaatctgaga agcaccaaac                                               20

<210> SEQ ID NO 93
<211> LENGTH: 20
<212> TYPE: DNA
<213> ORGANISM: Homo sapiens

<400> SEQUENCE: 93
acatcatagg gagcatcatc                                               20

<210> SEQ ID NO 94
<211> LENGTH: 20
<212> TYPE: DNA
<213> ORGANISM: Homo sapiens

<400> SEQUENCE: 94
tcaatcccca catttagttc                                               20

<210> SEQ ID NO 95
<211> LENGTH: 21
<212> TYPE: DNA
<213> ORGANISM: Homo sapiens

<400> SEQUENCE: 95
ctctaataag gaaagctcca g                                             21
```

```
<210> SEQ ID NO 96
<211> LENGTH: 22
<212> TYPE: DNA
<213> ORGANISM: Homo sapiens

<400> SEQUENCE: 96
ggtcacgatg aatataattc cg                                              22

<210> SEQ ID NO 97
<211> LENGTH: 19
<212> TYPE: DNA
<213> ORGANISM: Homo sapiens

<400> SEQUENCE: 97
atctgcaggt tttccaaag                                                  19

<210> SEQ ID NO 98
<211> LENGTH: 18
<212> TYPE: DNA
<213> ORGANISM: Homo sapiens

<400> SEQUENCE: 98
ccaggctgta gtaacagg                                                   18

<210> SEQ ID NO 99
<211> LENGTH: 20
<212> TYPE: DNA
<213> ORGANISM: Homo sapiens

<400> SEQUENCE: 99
taaggtcttc aacacattgc                                                 20

<210> SEQ ID NO 100
<211> LENGTH: 20
<212> TYPE: DNA
<213> ORGANISM: Homo sapiens

<400> SEQUENCE: 100
acttgaatat gttgccaagc                                                 20

<210> SEQ ID NO 101
<211> LENGTH: 20
<212> TYPE: DNA
<213> ORGANISM: Homo sapiens

<400> SEQUENCE: 101
cacacttcac agttacttgg                                                 20

<210> SEQ ID NO 102
<211> LENGTH: 20
<212> TYPE: DNA
<213> ORGANISM: Homo sapiens

<400> SEQUENCE: 102
atcacatttc acagctgaac                                                 20

<210> SEQ ID NO 103
<211> LENGTH: 20
<212> TYPE: DNA
<213> ORGANISM: Homo sapiens

<400> SEQUENCE: 103
agattgcctc tatttgttgc                                                 20
```

```
<210> SEQ ID NO 104
<211> LENGTH: 21
<212> TYPE: DNA
<213> ORGANISM: Homo sapiens

<400> SEQUENCE: 104
tagatatggt acaaggaagc c                                          21

<210> SEQ ID NO 105
<211> LENGTH: 20
<212> TYPE: DNA
<213> ORGANISM: Homo sapiens

<400> SEQUENCE: 105
ttctcttgac ttcactggtc                                            20

<210> SEQ ID NO 106
<211> LENGTH: 20
<212> TYPE: DNA
<213> ORGANISM: Homo sapiens

<400> SEQUENCE: 106
ttgcttagtt tcttgtctgg                                            20

<210> SEQ ID NO 107
<211> LENGTH: 20
<212> TYPE: DNA
<213> ORGANISM: Homo sapiens

<400> SEQUENCE: 107
tggtagctga tctcatactg                                            20

<210> SEQ ID NO 108
<211> LENGTH: 20
<212> TYPE: DNA
<213> ORGANISM: Homo sapiens

<400> SEQUENCE: 108
tccaccactg attctgtatg                                            20

<210> SEQ ID NO 109
<211> LENGTH: 20
<212> TYPE: DNA
<213> ORGANISM: Homo sapiens

<400> SEQUENCE: 109
ttcctatgtg gaatctgtcg                                            20

<210> SEQ ID NO 110
<211> LENGTH: 19
<212> TYPE: DNA
<213> ORGANISM: Homo sapiens

<400> SEQUENCE: 110
ataaaacaga aacacgcgg                                             19

<210> SEQ ID NO 111
<211> LENGTH: 20
<212> TYPE: DNA
<213> ORGANISM: Homo sapiens

<400> SEQUENCE: 111
```
tagaagtgca gaagttggag                                                   20

<210> SEQ ID NO 112
<211> LENGTH: 21
<212> TYPE: DNA
<213> ORGANISM: Homo sapiens

<400> SEQUENCE: 112
gtaccatttg atatcaggag c                                                 21

<210> SEQ ID NO 113
<211> LENGTH: 22
<212> TYPE: DNA
<213> ORGANISM: Homo sapiens

<400> SEQUENCE: 113
tgttatagta acccatccag ac                                                22

<210> SEQ ID NO 114
<211> LENGTH: 21
<212> TYPE: DNA
<213> ORGANISM: Homo sapiens

<400> SEQUENCE: 114
gggagtcttg agaaaatcta c                                                 21

<210> SEQ ID NO 115
<211> LENGTH: 20
<212> TYPE: DNA
<213> ORGANISM: Homo sapiens

<400> SEQUENCE: 115
gaatttctag ttctcgtggg                                                   20

<210> SEQ ID NO 116
<211> LENGTH: 22
<212> TYPE: DNA
<213> ORGANISM: Homo sapiens

<400> SEQUENCE: 116
gtcactcata agtgcataca tc                                                22

<210> SEQ ID NO 117
<211> LENGTH: 20
<212> TYPE: DNA
<213> ORGANISM: Homo sapiens

<400> SEQUENCE: 117
tccagagcaa ggataatctg                                                   20

<210> SEQ ID NO 118
<211> LENGTH: 20
<212> TYPE: DNA
<213> ORGANISM: Homo sapiens

<400> SEQUENCE: 118
aagcttcttg gatttgatgg                                                   20